United States Patent
Gross et al.

(10) Patent No.: US 7,473,541 B2
(45) Date of Patent: Jan. 6, 2009

(54) IDENTIFICATION, CLONING, EXPRESSION, AND PURIFICATION OF THREE NOVEL HUMAN CALCIUM-INDEPENDENT PHOSPHOLIPASE $A_2$ FAMILY MEMBERS POSSESSING TRIACYLGLYCEROL LIPASE AND ACYLGLYCEROL TRANSACYLASE ACTIVITIES

(76) Inventors: Richard W. Gross, 307 Chesterfield Oaks, Chesterfield, MO (US) 63005; Christopher Jenkins, 1004 Blendon Pl., Apartment 2-South, Richmond Heights, MO (US) 63117

( * ) Notice: Subject to any disclaimer, the term of this patent is extended or adjusted under 35 U.S.C. 154(b) by 247 days.

(21) Appl. No.: 11/179,363

(22) Filed: Jul. 11, 2005

(65) Prior Publication Data

US 2006/0051841 A1    Mar. 9, 2006

Related U.S. Application Data

(60) Provisional application No. 60/586,913, filed on Jul. 9, 2004.

(51) Int. Cl.
*C12N 9/20* (2006.01)

(52) U.S. Cl. .................... 435/198; 536/23.2
(58) Field of Classification Search ........... 435/198; 536/23.2
See application file for complete search history.

(56) References Cited

U.S. PATENT DOCUMENTS 7,407,786 B2 *    8/2008    Giver et al. .................. 435/198

* cited by examiner

*Primary Examiner*—Tekchand Saidha
(74) *Attorney, Agent, or Firm*—Armstrong Teasdale LLP

(57) ABSTRACT

Isolated novel and purified and characterized phospholipase $A_2$, referred to herein as calcium-independent phospholipase $A_2$zeta (iPLA$_2$zeta) having SEQ. ID. NO: 2 (See FIG. 1), and nucleic acid sequence (SEQ. ID. NO: 4), and calcium-independent phospholipase $A_2$eta (iPLA$_2$eta) having SEQ. ID. NO: 3 (See FIG. 1), and nucleic acid sequences (SEQ. ID. NO: 5). For the first time herein, these novel enzymes have been isolated and characterized and are involved in the catalysis, synthesis and hydrolysis of lipids in a living mammalian cell. Moreover, these enzymes iPLA$_2$zeta and iPLA$_2$eta through the process of transesterification can catalyze the net anabolic synthesis of triglycerides through a variety of metabolic precursors (e.g. monoacylglycerol, diacylglycerol and acyl CoA).

11 Claims, 13 Drawing Sheets

|  |  | 1 |  |  |  | 50 |
|---|---|---|---|---|---|---|
| SEQ. ID. NO. 1 | iPLA₂ | MYDAERGWSL | SFA GCGFLG F | YHVGATRCLS | EHAPHLLRDA | RMLF GASAG A |
| SEQ. ID. NO. 2 | iPLA₂ | MFPREKTWNI | SFA GCGFLG V | YYVGVASCLR | EHAPFLVANA | THIY GASAG A |
| SEQ. ID. NO. 3 | iPLA₂ | ....MKHINL | SFA ACGFLG I | YHLGAASALC | RHGKKLVKDV | KAFA GASAG F |
|  |  |  | Nucleotide |  |  | Lipase |

|  | 51 |  |  |  | 100 |
|---|---|---|---|---|---|
| iPLA₂ | LHCVG...VL | SGIPLEQTLQ | VLSDLVRKAR | SRNIGIFHPS | FNLSKFLRQG |
| iPLA₂ | LTATA...LV | TGVCLGEAGA | KFIEVSKEAR | KRFLGPLHPS | FNLVKIIRSF |
| iPLA₂ | TSLVASVLLT | APEKIEECNQ | FTYKFAEEIR | RQSFGAVTPG | YDFMARLRSG |

|  | 101 |  |  |  | 150 |
|---|---|---|---|---|---|
| iPLA₂ | LCKCLPANVH | ..QLISGKIG | ISLTRVSDGE | NVLVSDFRSK | DEVVDALVCS |
| iPLA₂ | LLKVLPADSH | ..EHASGRLG | ISLTRVSDGE | NVIISHFNSK | DELIQANVCS |
| iPLA₂ | MESILPPSAH | FTELAQNRLH | VSITNAKTRE | NHLVSTFSSR | EDLIKVLLAS |

|  | 151 |  |  |  | 200 |
|---|---|---|---|---|---|
| iPLA₂ | CFIPFYSGLI | PPSFRGVRYV | D..GGVSDNV | PFIDAKTTIT | VSPFYGEYDI |
| iPLA₂ | GFIPVYCGLI | PPSLQGVRYV | D..GGISDNL | PLYELKNTIT | VSPFSGESDI |
| iPLA₂ | SFVPIYAGLK | LVEYKGQKWV | DFTGGLTNAL | PILPVGRTVT | ISPFSGRLDI |

|  | 201 |  |  |  | 250 |
|---|---|---|---|---|---|
| iPLA₂ | CPKVKSTNFL | HVDITKLSLR | LCTGNLYLLS | RAF..VPPDL | KVLGEICLRG |
| iPLA₂ | CPQDSSTNIH | ELRVTNTSIQ | FNLRNLYRLS | KAL..FPPEP | LVLREMCKQG |
| iPLA₂ | SPQDKGQLDL | YVNIAKQDIM | LSLANLVRLN | QAFTLFPPSK | RKMESLYQCG |

|  | 251 |  |  |  | 300 |
|---|---|---|---|---|---|
| iPLA₂ | YLDAFRFLEE | KGICNRPQPG | LKSSSEGMDP | EVAMPSWANM | SLDSSPESAA |
| iPLA₂ | YRDGLRFLQR | NGLLNRPNPL | L......... | ..ALPP.... | ARPHGPEDKD |
| iPLA₂ | FDDTVKFLLK | ENWFEHₓ... | .......... | .......... | .......... |

|  | 301 |  |  |  | 350 |
|---|---|---|---|---|---|
| iPLA₂ | LAVRLEGDEL | LDHLRLSILP | WDESILDTLS | PRLATALSEE | MKDKGGYMSK |
| iPLA₂ | QAV..ESAQA | EDY...SQLP | GEDHILEHLP | ARLNEALLEA | CVEPTDLLTT |

|  | 351 |  |  |  | 400 |
|---|---|---|---|---|---|
| iPLA₂ | ICNLLPIRIM | SYVMLPCTLP | VESAIAIVQR | LVTWLPDMPD | DVLWLQWVTS |
| iPLA₂ | LSNMLPVRLA | TAMMVPYTLP | LESALSFTIR | LLEWLPDVPE | DIRWMKEQTG |

|  | 401 |  |  |  | 450 |
|---|---|---|---|---|---|
| iPLA₂ | QVFTRVLMCL | .......LPA | SR.SQMPVSS | QQASPCTP.. | ....EQDWPC |
| iPLA₂ | SICQYLVMRA | KRKLGRHLPS | RLPEQVELRR | VQSLPSVPLS | CAAYREALPG |

|  | 451 |  |  |  | 500 |
|---|---|---|---|---|---|
| iPLA₂ | WTPCSPEGCP | AETKAEATPR | SILRSSLNFF | LGNKVPAGAE | GLSTFPSFSL |
| iPLA₂ | WMRNNLSLGD | ALAKWEECQR | QLLLGLFCTN | VAFPPEALRM | RAPADPAPAP |

|  | 501 |  | 533 |
|---|---|---|---|
| iPLA₂ | EKSLHₓ.... | .......... | ... |
| iPLA₂ | ADPASPQHQP | AGPAPLLSTP | APEARPVIGA | LGLHₓ |

Fig. 1

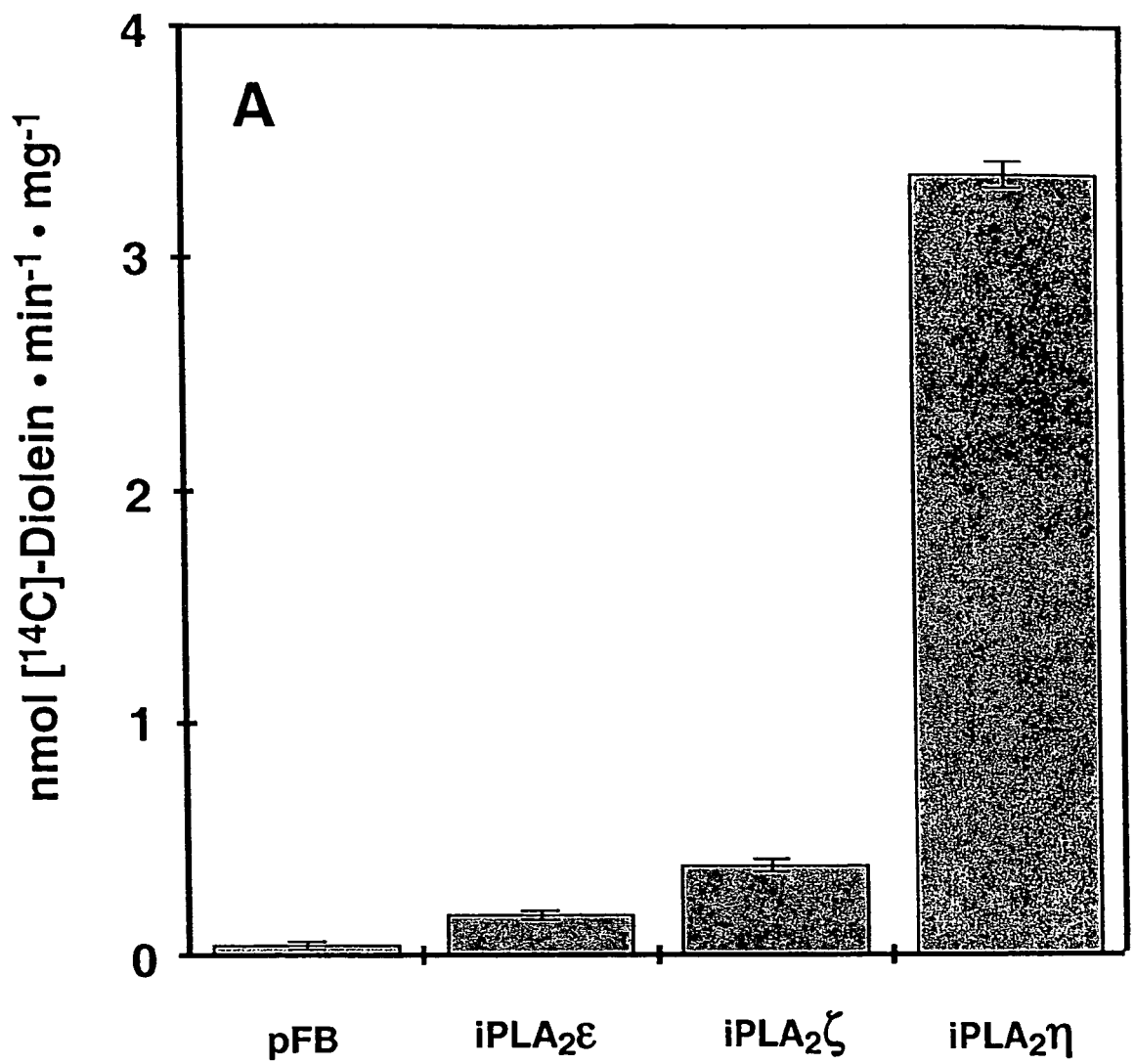
*Fig. 4*<sub>a</sub> iPLA$_2\zeta$ (zeta) (SEQ ID NO: 4)

```
atgtttccccgcgagaagacgtggaacatctcgttcgcgggctgcggcttcctcggcgtc
 M  F  P  R  E  K  T  W  N  I  S  F  A  G  C  G  F  L  G  V
tactacgtcggcgtggcctcctgcctccgcgagcacgcccttcctggtggccaacgcc
 Y  Y  V  G  V  A  S  C  L  R  E  H  A  P  F  L  V  A  N  A
acgcacatctacggcgcctcggccggggcgctcacggccacggcgctggtcaccggggtc
 T  H  I  Y  G  A  S  A  G  A  L  T  A  T  A  L  V  T  G  V
tgcctgggtgaggctggtgccaagttcattgaggtatctaaagaggcccggaagcggttc
 C  L  G  E  A  G  A  K  F  I  E  V  S  K  E  A  R  K  R  F
ctgggccccctgcacccctccttcaacctggtaaagatcatccgcagtttcctgctgaag
 L  G  P  L  H  P  S  F  N  L  V  K  I  I  R  S  F  L  L  K
gtcctgcctgctgatagccatgagcatgccagtgggcgcctgggcatctccctgacccgc
 V  L  P  A  D  S  H  E  H  A  S  G  R  L  G  I  S  L  T  R
gtgtcagacggcgagaatgtcattatatcccacttcaactccaaggacgagctcatccag
 V  S  D  G  E  N  V  I  I  S  H  F  N  S  K  D  E  L  I  Q
gccaatgtctgcagcggtttcatccccgtgtactgtgggctcatccctccctcccag
 A  N  V  C  S  G  F  I  P  V  Y  C  G  L  I  P  P  S  L  Q
ggggtgcgctacgtggatggtggcatttcagacaacctgccactctatgagcttaagaac
 G  V  R  Y  V  D  G  G  I  S  D  N  L  P  L  Y  E  L  K  N
accatcacagtgtccccttctcgggcgagagtgacatctgtccgcaggacagctccacc
 T  I  T  V  S  P  F  S  G  E  S  D  I  C  P  Q  D  S  S  T
aacatccacgagctgcgggtcaccaacaccagcatccagttcaacctgcgcaacctctac
 N  I  H  E  L  R  V  T  N  T  S  I  Q  F  N  L  R  N  L  Y
cgcctctccaaggccctcttcccgccggagcccctggtgctgcgagagatgtgcaagcag
 R  L  S  K  A  L  F  P  P  E  P  L  V  L  R  E  M  C  K  Q
ggataccgggatggcctgcgctttctgcagcggaacggcctcctgaaccggcccaacccc
 G  Y  R  D  G  L  R  F  L  Q  R  N  G  L  L  N  R  P  N  P
ttgctggcgttgccccccgcccgcccccacggcccagaggacaaggaccaggcagtggag
 L  L  A  L  P  P  A  R  P  H  G  P  E  D  K  D  Q  A  V  E
agcgcccaagcggaggattactcgcagctgcccggagaagatcacatcctggagcacctg
 S  A  Q  A  E  D  Y  S  Q  L  P  G  E  D  H  I  L  E  H  L
cccgcccggctcaatgaggccctgctggaggcctgcgtggagcccacggacctgctgacc
 P  A  R  L  N  E  A  L  L  E  A  C  V  E  P  T  D  L  L  T
accctctccaacatgctgcctgtgcgtctggccacggccatgatggtgccctacacgctg
 T  L  S  N  M  L  P  V  R  L  A  T  A  M  M  V  P  Y  T  L
ccgctggagagcgctctgtccttcaccatccgcttgctggagtggctgcccgacgttccc
 P  L  E  S  A  L  S  F  T  I  R  L  L  E  W  L  P  D  V  P
gaggacatccggtggatgaaggagcagacgggcagcatctgccagtacctggtgatgcgc
 E  D  I  R  W  M  K  E  Q  T  G  S  I  C  Q  Y  L  V  M  R
gccaagaggaagctgggcaggcacctgccctccaggctgccggagcaggtggagctgcgc
 A  K  R  K  L  G  R  H  L  P  S  R  L  P  E  Q  V  E  L  R
cgcgtccagtcgctgccgtccgtgccgctgtcctgcgccgcctacagagaggcactgccc
 R  V  Q  S  L  P  S  V  P  L  S  C  A  A  Y  R  E  A  L  P
ggctggatgcgcaacaacctctcgctgggggacgcgctggccaagtgggaggagtgccag
 G  W  M  R  N  N  L  S  L  G  D  A  L  A  K  W  E  E  C  Q
cgccagctgctgctcggcctcttctgcaccaacgtggccttcccgcccgaagctctcgc
 R  Q  L  L  L  G  L  F  C  T  N  V  A  F  P  P  E  A  L  R
atgcgcgcacccgccgacccggctcccgcccccgcggaccagcatccccgcagcaccag
 M  R  A  P  A  D  P  A  P  A  P  A  D  P  A  S  P  Q  H  Q
ccggccgggcctgccccttgctgagcaccctgctcccgaggccggcccgtgatcggg
 P  A  G  P  A  P  L  L  S  T  P  A  P  E  A  R  P  V  I  G
gccctggggctgtga
 A  L  G  L  -
```

*Fig. 7* iPLA₂η (eta) (SEQ ID NO: 5)

```
atgaagcacatcaacctatcatttgcagcgtgtggatttctgggcatttaccacttgggg
 M   K   H   I   N   L   S   F   A   A   C   G   F   L   G   I   Y   H   L   G
gcagcatctgcactttgcagacatggcaaaaaacttgtgaaggatgtcaaagccttcgct
 A   A   S   A   L   C   R   H   G   K   K   L   V   K   D   V   K   A   F   A
ggggcgtctgcgggatcgttggttgcttctgttctgctaacagcaccagaaaaaatagag
 G   A   S   A   G   S   L   V   A   S   V   L   L   T   A   P   E   K   I   E
gaatgtaaccaatttacctacaagtttgccgaagaaatcagaaggcagtctttcggggca
 E   C   N   Q   F   T   Y   K   F   A   E   E   I   R   R   Q   S   F   G   A
gtaacgcccggttatgacttcatggcccgactaagaagtgggatggagtcgattcttcct
 V   T   P   G   Y   D   F   M   A   R   L   R   S   G   M   E   S   I   L   P
cccagcgctcacgagctggcccagaaccgactgcacgtatccatcaccaacgccaaaacc
 P   S   A   H   E   L   A   Q   N   R   L   H   V   S   I   T   N   A   K   T
agagaaaatcacttagtctccacttttcctccagggaggacctcattaaggtcctccta
 R   E   N   H   L   V   S   T   F   S   S   R   E   D   L   I   K   V   L   L
gccagcagttttgtgcccatttatgcaggactgaagctagtggaatacaaagggcagaag
 A   S   S   F   V   P   I   Y   A   G   L   K   L   V   E   Y   K   G   Q   K
tgggtggacggaggcctcaccaacgctcttccatcctgcccgtcggccggacagtaacc
 W   V   D   G   G   L   T   N   A   L   P   I   L   P   V   G   R   T   V   T
atctccccttcagtggacgactggacatctccccgcaggacaaagggcagctagatctg
 I   S   P   F   S   G   R   L   D   I   S   P   Q   D   K   G   Q   L   D   L
tatgttaatatcgccaagcaggatatcatgttgtccctggcaaacctggtgagactcaac
 Y   V   N   I   A   K   Q   D   I   M   L   S   L   A   N   L   V   R   L   N
caagcccttttccccaagcaagaggaaaatggaatctttgtatcagtgtggttttgat
 Q   A   L   F   P   P   S   K   R   K   M   E   S   L   Y   Q   C   G   F   D
gacactgttaagttttacttaaagaaaattggtttgaataa
 D   T   V   K   F   L   L   K   E   N   W   F   -
```

*Fig. 8*

Human Adiponutrin (iPLA₂ε)
Sequence ID= AK025665 (nucleotide); reference SNP ID = rs2294918(g)

```
SEQ ID 3: atgtacgacgcagagcgcggctggagcttgtccttcgcgggctgcggcttcctgggcttc
SEQ ID 1: M  Y  D  A  E  R  G  W  S  L  S  F  A  G  C  G  F  L  G  F
          taccacgtcggggcgacccgctgcctgagcgagcacgccccgcacctcctccgcgacgcg
          Y  H  V  G  A  T  R  C  L  S  E  H  A  P  H  L  L  R  D  A
          cgcatgttgttcggcgcttcggccggggcgttgcactgcgtcggcgtcctctccggtatc
          R  M  L  F  G  A  S  A  G  A  L  H  C  V  G  V  L  S  G  I
                          ─────────
                              |
                            O - R
          ccgctggagcagactctgcaggtcctctcagatcttgtgcggaaggccaggagtcggaac
          P  L  E  Q  T  L  Q  V  L  S  D  L  V  R  K  A  R  S  R  N
          attggcatcttccatccatccttcaacttaagcaagttcctccgacagggtctctgcaaa
          I  G  I  F  H  P  S  F  N  L  S  K  F  L  R  Q  G  L  C  K
          tgcctcccggccaatgtccaccagctcatctccggcaaaataggcatctctcttaccaga
          C  L  P  A  N  V  H  Q  L  I  S  G  K  I  G  I  S  L  T  R
          gtgtctgatggggaaaacgttctggtgtctgactttcggtccaaagacgaagtcgtggat
          V  S  D  G  E  N  V  L  V  S  D  F  R  S  K  D  E  V  V  D
          gccttggtatgttcctgcttcatccccttctacagtggcctta tccctccttccttcaga
          A  L  V  C  S  C  F  I  P  F  Y  S  G  L  I  P  P  S  F  R
          ggcgtgcgatatgtggatggaggagtgagtgacaacgtacccttcattgatgccaaaaca
          G  V  R  Y  V  D  G  G  V  S  D  N  V  P  F  I  D  A  K  T
          accatcaccgtgtccccc ttctatggggagtacgacatctgccctaaagtcaagtccacg
          T  I  T  V  S  P  F  Y  G  E  Y  D  I  C  P  K  V  K  S  T
          aactttcttcatgtggacatcaccaagctcagtctacgcctctgcacagggaacctctac
          N  F  L  H  V  D  I  T  K  L  S  L  R  L  C  T  G  N  L  Y
          cttctctcgagagcttttgtccccccggatctcaaggtgctgggagagatatgccttcga
          L  L  S  R  A  F  V  P  P  D  L  K  V  L  G  E  I  C  L  R
          ggatatttggatgcattcaggttcttggaagagaagggcatctgcaacaggccccagcca
          G  Y  L  D  A  F  R  F  L  E  E  K  G  I  C  N  R  P  Q  P
          ggcctgaagtcatcctcagaagggatggatcctgaggtcgccatgcccagctgggcaaac
          G  L  K  S  S  E  G  M  D  P  E  V  A  M  P  S  W  A  N
          atgagtctggattcttccccggagtcggctgccttggctgtgaggctggagggagatgag
          M  S  L  D  S  S  P  E  S  A  A  L  A  V  R  L  E  G  D  E
          ctgctagaccacctgcgtctcagcatcctgccctgggatgagagcatcctggacaccctc
          L  L  D  H  L  R  L  S  I  L  P  W  D  E  S  I  L  D  T  L
          tcgcccaggctcgctacagcactgagtgaagaaatgaaagacaaaggtggatacatgagc
          S  P  R  L  A  T  A  L  S  E  E  M  K  D  K  G  G  Y  M  S
          aagatttgcaacttgctacccattaggataatgtcttatgtaatgctgccctgtaccctg
          K  I  C  N  L  L  P  I  R  I  M  S  Y  V  M  L  P  C  T  L
          cctgtggaatctgccattgcgattgtccagagactggtgacatggcttccagatatgccc
          P  V  E  S  A  I  A  I  V  Q  R  L  V  T  W  L  P  D  M  P
          gacgatgtcctgtggttgcagtgggtgacctcacaggtgttcactcgagtgctgatgtgt
          D  D  V  L  W  L  Q  W  V  T  S  Q  V  F  T  R  V  L  M  C
          ctgctccccgcctccaggtcccaaatgccagtgagcagccaacaggcctccccatgcaca
          L  L  P  A  S  R  S  Q  M  P  V  S  Q  Q  A  S  P  C  T
          cctgagcaggactggccctgctggactccctgctccccgagggctgtccagcagagacc
          P  E  Q  D  W  P  C  W  T  P  C  S  P [E] G  C  P  A  E  T
          aaagcagaggccaccccgcggtccatcctcaggtccagcctgaacttcttcttgggcaat
          K  A  E  A  T  P  R  S  I  L  R  S  S  L  N  F  F  L  G  N
          aaagtacctgctggtgctgaggggctctccacctttcccagttttttcactagagaagagt
          K  V  P  A  G  A  E  G  L  S  T  F  P  S  F  S  L  E  K  S
          ctgtga
          L   -
```

Fig. 10

Human Adiponutrin (iPLA₂ε)
Sequence ID= AL138578.2 (nucleotide); NP_079501 (protein);
reference SNP ID = rs2294918(a)

```
SEQ ID 4: atgtacgacgcagagcgcggctggagcttgtccttcgcgggctgcggcttcctgggcttc
SEQ ID 2:  M  Y  D  A  E  R  G  W  S  L  S  F  A  G  C  G  F  L  G  F
           taccacgtcggggcgacccgctgcctgagcgagcacgccccgcacctcctccgcgacgcg
            Y  H  V  G  A  T  R  C  L  S  E  H  A  P  H  L  L  R  D  A
           cgcatgttgttcggcgcttcggccggggcgttgcactgcgtcggcgtcctctccggtatc
            R  M  L  F  G  A  S  A  G  A  L  H  C  V  G  V  L  S  G  I
                          ─────────
                              |
                            O - R
           ccgctggagcagactctgcaggtcctctcagatcttgtgcggaaggccaggagtcggaac
            P  L  E  Q  T  L  Q  V  L  S  D  L  V  R  K  A  R  S  R  N
           attggcatcttccatccatccttcaacttaagcaagttcctccgacagggtctctgcaaa
            I  G  I  F  H  P  S  F  N  L  S  K  F  L  R  Q  G  L  C  K
           tgcctcccggccaatgtccaccagctcatctccggcaaaataggcatctctcttaccaga
            C  L  P  A  N  V  H  Q  L  I  S  G  K  I  G  I  S  L  T  R
           gtgtctgatggggaaaacgttctggtgtctgactttcggtccaaagacgaagtcgtggat
            V  S  D  G  E  N  V  L  V  S  D  F  R  S  K  D  E  V  V  D
           gccttggtatgttcctgcttcatccccttctacagtggccttatccctccttccttcaga
            A  L  V  C  S  F  I  P  F  Y  S  G  L  I  P  P  S  F  R
           ggcgtgcgatatgtggatggaggagtgagtgacaacgtacccttcattgatgccaaaaca
            G  V  R  Y  V  D  G  G  V  S  D  N  V  P  F  I  D  A  K  T
           accatcaccgtgtccccttctatggggagtacgacatctgccctaaagtcaagtccacg
            T  I  T  V  S  P  F  Y  G  E  Y  D  I  C  P  K  V  K  S  T
           aactttcttcatgtggacatcaccaagctcagtctacgcctctgcacagggaacctctac
            N  F  L  H  V  D  I  T  K  L  S  L  R  L  C  T  G  N  L  Y
           cttctctcgagagcttttgtccccccggatctcaaggtgctgggagagatatgccttcga
            L  L  S  R  A  F  V  P  P  D  L  K  V  L  G  E  I  C  L  R
           ggatatttggatgcattcaggttcttggaagagaaagggcatctgcaacaggccccagcca
            G  Y  L  D  A  F  R  F  L  E  E  K  G  I  C  N  R  P  Q  P
           ggcctgaagtcatcctcagaagggatggatcctgaggtcgccatgcccagctgggcaaac
            G  L  K  S  S  E  G  M  D  P  E  V  A  M  P  S  W  A  N
           atgagtctggattcttccccggagtcggctgccttggctgtgaggctggagggagatgag
            M  S  L  D  S  S  P  E  S  A  A  L  A  V  R  L  E  G  D  E
           ctgctagaccacctgcgtctcagcatcctgccctgggatgagagcatcctggacaccctc
            L  L  D  H  L  R  L  S  I  L  P  W  D  E  S  I  L  D  T  L
           tcgcccaggctcgctacagcactgagtgaagaaatgaaagacaaaggtggatacatgagc
            S  P  R  L  A  T  A  L  S  E  E  M  K  D  K  G  G  Y  M  S
           aagatttgcaacttgctacccattaggataatgtcttatgtaatgctgccctgtaccctg
            K  I  C  N  L  L  P  I  R  I  M  S  Y  V  M  L  P  C  T  L
           cctgtggaatctgccattgcgattgtccagagactggtgacatggcttccagatatgccc
            P  V  E  S  A  I  A  I  V  Q  R  L  V  T  W  L  P  D  M  P
           gacgatgtcctgtggttgcagtgggtgacctcacaggtgttcactcgagtgctgatgtgt
            D  D  V  L  W  L  Q  W  V  T  S  Q  V  F  T  R  V  L  M  C
           ctgctccccgcctccaggtcccaaatgccagtgagcagccaacaggcctccccatgcaca
            L  L  P  A  S  R  S  Q  M  P  V  S  Q  Q  A  S  P  C  T
           cctgagcaggactggccctgctggactccctgctcccccaagggctgtccagcagagacc
            P  E  Q  D  W  P  C  W  T  P  C  S  P [K] G  C  P  A  E  T
           aaagcagaggccaccccgcggtccatcctcaggtccagcctgaacttcttcttgggcaat
            K  A  E  A  T  P  R  S  I  L  R  S  S  L  N  F  F  L  G  N
           aaagtacctgctggtgctgaggggctctccacctttcccagtttttcactagagaagagt
            K  V  P  A  G  A  E  G  L  S  T  F  P  S  F  S  L  E  K  S
           ctgtga
            L  -
```

Fig. 11

IDENTIFICATION, CLONING, EXPRESSION, AND PURIFICATION OF THREE NOVEL HUMAN CALCIUM-INDEPENDENT PHOSPHOLIPASE A$_2$ FAMILY MEMBERS POSSESSING TRIACYLGLYCEROL LIPASE AND ACYLGLYCEROL TRANSACYLASE ACTIVITIES

This application claims the benefit of U.S. Ser. No. 60/586,913 filed Jul. 9, 2004 which is incorporated herein in its entirety. This application also claims the benefit of U.S. Ser. No. 11/010,558, filed Dec. 13, 2004 which is incorporated here in its entirety.

STATEMENT REGARDING FEDERALLY SPONSORED RESEARCH AND DEVELOPMENT

This research was supported jointly by National Institutes of Health grants 2PO1HL57278-06A1 and 2RO1HL41250-10. The government has certain rights in the invention.

FIELD OF THE INVENTION

This invention relates to lipases and more particularly to human calcium independent lipases A$_2$, nucleic acids capably expressing such lipases, to use of such lipases as pharmacological targets in screening to identify potentially useful anti-obesity drugs and drugs for other sequelae of the metabolic syndrome including at least one of atherosclerosis, diabetes and hypertension in humans and to a functional animal model useful for such screening.

BACKGROUND OF THE INVENTION

In many industrialized countries, the incidence of human obesity is ever increasing. Moreover, human obesity is a common and costly nutritional problem in the United States, Obesity is characterized clinically by the accumulation of fat tissue (at times this is referred to as body fat content).

In humans, obesity is usually defined as a body fat content greater than about 25% of the total weight for males, or greater than 30% of the total weight for females. Regardless of the cause of obesity, obesity is an ever present problem for Americans. But a fat content >18% for males and >22% for females can have untold consequences secondary to several mechanisms and disorders of metabolic function. For example, obesity can have a significant adverse impact on health care costs and provoke a higher risk of numerous illnesses, including heart attacks, strokes and diabetes.

Without being bound by theory, it is believed that obesity in humans results from an abnormal increase in white adipose tissue mass that occurs due to an increased number of adipocytes (hyperplasia) or from increased lipid mass (stored as triglycerides) accumulating in existing adipocytes. Obesity and the associated type 2 metabolic syndrome along with its clinical sequelae are among the major and the most rapidly increasing medical problems in America. However, to date, a lack of suitable adipocyte specific protein targets has unfortunately hampered progress in the development of effective therapeutic agents to combat the clinical sequelae of obesity.

Despite existing knowledge of the critical role of phospholipases and triglyceride lipases in adipocyte signaling, enhanced clinical methodology and research tools and research methods are highly needed for identifying useful drugs to treat obesity and over-weightness. It is highly desired to have technology based on the specific types of phospholipases and triglyceride lipases present in the adipocyte or their mechanisms of regulation and determine their natural substrates and roles in anabolic lipid metabolism, catabolic lipid metabolism or both (e.g. triglyceride cycling).

Additionally, a screening method and research tool is needed to identify useful drugs which can be used to reduce the fat level of a living mammal and/or to maintain the fat level at a predetermined level.

BRIEF DESCRIPTION OF THE INVENTION

This invention relates to phospholipases and more particularly to human calcium independent phospholipase A$_2$, hereinafter referred to as and denoted iPLA$_2$, to nucleic acids expressing iPLA$_2$, to use of iPLA$_2$ as a pharmacological target in screening to identify potentially useful anti-obesity drugs and drugs for other sequelae of the metabolic syndrome including at least one of atherosclerosis, diabetes and hypertension and to a functional animal model useful for such screening. This discovery has utility.

In an aspect, the invention provides for the first time isolated, novel, purified, functional, characterized and useful phospholipases A$_2$ referred to herein as calcium-independent lipase A$_2$zeta (iPLA$_2$zeta) having SEQ. ID. NO: 2 (See FIG. 1) and nucleic acid sequence SEQ. ID. NO: 4 (See FIG. 7), and calcium-independent lipase A$_2$eta (iPLA$_2$eta) having SEQ. ID. NO: 3 (See FIG. 1) and nucleic acid sequence SEQ. ID. NO: 5 (See FIG. 8). For the first time herein, these novel enzymes have been isolated and characterized and have been discovered to be involved in the catalysis, synthesis and hydrolysis of lipids in a living mammalian cell. Moreover, these enzymes iPLA$_2$zeta and iPLA$_2$eta through the process of transesterification can each independently catalyze the net anabolic synthesis of triglycerides through a variety of metabolic precursors (e.g. monoacylglycerol, diacylglycerol and acyl CoA).

In one embodiment, the invention is directed to an isolated and characterized nucleic acid molecule comprising a set of iPLA$_2$zeta polynucleotides. In an aspect of this embodiment, the iPLA$_2$zeta polynucleotides (SEQ. ID. NO: 4) encode (and express) an iPLA$_2$zeta polypeptide (SEQ. ID. NO. 2).

In one embodiment, the invention is directed to an isolated characterized nucleic acid molecule comprising a set of iPLA$_2$eta polynucleotides. In an aspect of this embodiment, the iPLA$_2$eta polynucleotides (SEQ. ID. NO: 5) encode (and express) an iPLA$_2$eta polypeptide (SEQ. ID. NO: 3).

In one aspect, an isolated and characterized human gene (iPLA$_2$zeta) comprises a characterized polynucleotide having a sequence shown in SEQ. ID. NO: 4 (See FIG. 7).

In one aspect, an isolated and characterized human gene (iPLA$_2$eta) comprises a polynucleotide having a sequence shown in SEQ. ID. NO: 5 (See FIG. 8).

In an aspect, an isolated and characterized human protein (iPLA$_2$zeta) comprises a polypeptide having a sequence shown in SEQ. ID. NO: 2 (See FIG. 1).

In an aspect, an isolated and characterized human protein (iPLA$_2$zeta) comprises a polypeptide having a sequence shown in SEQ. ID. NO: 2 (See FIG. 1) with a histidine tag (4-12 histidine residues).

In an aspect, an isolated and characterized human protein (iPLA$_2$eta) comprises a polypeptide having a sequence shown in SEQ. ID. NO: 3 (See FIG. 1).

In an aspect, an isolated and characterized human protein (iPLA$_2$eta) comprises a polypeptide having a sequence shown in SEQ. ID. NO: 3 (See FIG. 1) with a histidine tag (4-12 histidine residues).

In an aspect, the invention comprises a set of enzymes whose activities can be effectively modulated, alone or in concert, to have salutary effects on the sequelae of lipotoxicity by altering the amount and molecular species composition of triglycerides and/or phospholipids. These beneficial effects can be realized in multiple living mammalian cell types, including but not limited to myocardium, pancreatic beta cells, and macrophages during atheromatous plaque formation.

In an aspect, a method to improve the insulin sensitivity of the organism by effectively modulating the amounts of fatty acids, fatty acyl-CoAs, and other lipid species in pancreatic beta cells, muscle, or liver which contribute to insulin resistance in Type 2 diabetes.

In an aspect, a method to attenuate the development and progression of atherosclerosis and vascular disease by altering the lipid composition of plasma and modifying the lipid metabolism of critical cells that promote atherogenesis (e.g. macrophages, smooth muscle cells, and platelets), In an aspect, a method of protecting against or modifying the deleterious sequelae of heart attacks or strokes by altering the lipid composition of heart or brain cells to withstand episodes of ischemia, attack by free radicals, or effects due to dysfunctional lipid metabolism.

In an aspect, this discovery comprises a method to measure the types and amounts (assay) of different lipase activities in fat cells and their inhibition by BEL or other suitable pharmacologic agents.

In an aspect, a method of treating a living mammal to reduce obesity, which comprises administering an effective amount of iPLA$_2$zeta and/or iPLA$_2$eta inhibitor thereto or by administering an agent which changes the lipase to transacylase activity ratio.

In an aspect, a genetically engineered expression vector comprises a gene or part of the sequence of a human gene (iPLA$_2$zeta) comprising an isolated and characterized polynucleotide having a sequence shown in SEQ ID NO: 4. In an aspect, the gene encodes a protein, iPLA$_2$zeta, comprising a polypeptide having a sequence shown in SEQ ID NO: 2 (FIG. 1). In an aspect, the gene is operatively linked to a capable viable promoter element.

In an aspect, a genetically engineered expression vector comprises a gene or part of the sequence of a human gene (iPLA$_2$eta) comprising a polynucleotide having a sequence shown in SEQ ID NO: 5. In an aspect, the gene encodes a protein (iPLA$_2$eta) comprising a polypeptide having a sequence shown in SEQ ID NO: 3 (FIG. 1). In an aspect, the gene is operatively linked to a capable viable promoter element.

In another aspect, a method of medically treating a mammal comprises administering an anti-obesity (drug or pharmaceutical) to the mammal in therapeutically effective amounts as an inhibitor.

In another aspect, a method of medically treating a living mammal comprises administering a therapeutically effective amount of a moiety such as a compound (drug or pharmaceutical) which inhibits iPLA$_2$zeta and/or iPLA$_2$eta expression to the mammal which results in a different isoform expression or different enzymatic activity or post-translational modification.

In another aspect, a method of treating obesity, which comprises administering an agent selected from the group consisting of iPLA$_2$epsilon (adiponutrin), iPLA$_2$zeta (TTS-2.2), and iPLA$_2$eta (GS2) which changes the transacylase to lipase ratio of any or a combination of these three enzymes in a metabolic setting. In an aspect, the metabolic setting is a living animal or animal model.

In an aspect, a pharmaceutical composition is provided comprising a compound which effectively inhibits or counteracts iPLA$_2$epsilon (adiponutrin), iPLA$_2$zeta (TTS-2.2), and iPLA$_2$eta (GS2) expression, activity, phospholipase A$_2$ activity, hydrolysis or transesterification activity or transesterification in a living mammal.

In an aspect, a pharmaceutical kit comprises a container housing a compound which inhibits at least one of iPLA$_2$epsilon (adiponutrin), iPLA$_2$zeta (TTS-2.2), and iPLA$_2$eta (GS2) expression hydrolytic activity, phospholipase A$_2$ activity, or transesterification activity and optionally a carrier.

In another embodiment, the present invention is directed to a method of modulating fatty acid utilization in a patient. In an aspect, the patient is a living human patient. In this aspect, the method comprises increasing or decreasing iPLA$_2$zeta and/or iPLA$_2$eta activity in the patient. Patients in need of such treatment include those patients suffering from one of diabetes and/or obesity. Preferably, this method comprises administering to the patient a substance (compound) in an effective amount which blocks or inhibits expression of iPLA$_2$zeta and/or iPLA$_2$eta mass or activity.

In an aspect a method of identifying an agent which changes the ratio of transacylase to lipase activity in a living mammal by administering a compound to a mammal and determining if the transacylase to lipase ratio was changed by lipid analysis and if the ratio was changed then determining that the drug is an anti-obesity drug.

In an aspect, the invention comprises a method for ameliorating at least one symptom of a symptomatology comprising obesity and clinical manifestation of the type 2 metabolic syndrome in a living human which comprises treating a living human cell expressing iPLA$_2$zeta and/or iPLA$_2$eta in a pharmacologically effective manner with a pharmacologically effective amount of a drug which alters (increases or decreases) iPLA$_2$zeta and/or iPLA$_2$eta expression or activates or inhibits iPLA$_2$zeta and/or iPLA$_2$eta enzymatic activity.

A method of treating at least one of an overweight and obese disorders in a living animal or animal model, the method comprises administering to a subject (in need of such treatment) a therapeutically effective amount of a composition comprising an inhibitor of human iPLA$_2$zeta and/or iPLA$_2$eta.

A method of treating at least one of an overweight and obese disorders in a living animal or animal model, the method comprises administering to a subject (in need of such treatment) a therapeutically effective amount of a composition comprising an activator of human iPLA$_2$zeta and/or iPLA$_2$eta.

A screening and/or research tool useful to identify drugs useful to treat obesity. In a further aspect, a method (and/or screening or research tool) of identifying and/or for an anti-obesity drug comprises administering a drug to an animal and determining if there has been any change in iPLA$_2$zeta and/or iPLA$_2$eta expression, hydrolysis activity, phospholipase A$_2$ activity, or transesterification activity, or metabolic futile cycling and if so determining that the drug is an anti-obesity drug.

A method of practicing medicine which comprises administering a therapeutic amount of a drug to a patient at risk for obesity or being obese, the drug being an inhibitor of human iPLA$_2$zeta and/or iPLA$_2$eta.

A method of practicing medicine which comprises administering a therapeutic amount of a drug to a patient at risk for obesity or being obese, the drug being an activator of human iPLA$_2$zeta and/or iPLA$_2$eta.

A method of providing therapy to a patient in need thereof which comprises administering a drug to a patient at risk for obesity, the drug being an inhibitor of the expressing of human iPLA$_2$eta and/or iPLA$_2$eta.

A method of providing therapy to a patient in need thereof which comprises administering a drug to a patient at risk for obesity, the drug being an activator of the expressing of human iPLA$_2$zeta and/or iPLA$_2$eta.

A method for treating a diabetic patient which comprises administering a drug in an effective amount to modulate iPLA$_2$zeta and/or iPLA$_2$eta expression whereby the insulin requirement of the patient is decreased A method of treating diabetes which comprises administering a drug in an effective amount to modulate iPLA$_2$zeta and/or iPLA$_2$eta expression whereby the insulin requirement of the patient being treated for diabetes is decreased.

In an aspect, the present discovery encompasses genetically engineered cells capable of identifying substances which modulate iPLA$_2$zeta or iPLA$_2$eta expression in a living cell. In an aspect, such cells comprise a promoter operably linked to the iPLA$_2$zeta gene or the iPLA$_2$eta gene and a reporter gene. This reporter gene preferably encodes an enzyme capable of being detected by at least one of a suitable radiometric, fluorometric or lurninometric assay such as, for example, a reporter sequence encoding a luciferase. In an aspect, the promoter sequence is a baculovirus promoter sequence and the cells are Sf9 cells.

In an aspect, the invention comprises a method for prioritizing the therapeutic capability of drugs of putative efficacy against obesity, comprising administering drugs to a living animal system which is actively expressing iPLA$_2$epsilon, iPLA$_2$zeta, and/or iPLA$_2$eta, measuring any modulation of the iPLA$_2$epsilon, iPLA$_2$zeta, and/or iPLA$_2$eta expression by a TAG or free fatty acid/glycerol analysis of an effect and determining if the modulation was an increase or a decrease or no change in iPLA$_2$epsilon, iPLA$_2$zeta, and/or iPLA$_2$eta expression level. If the modulation is determined to be a decrease then determining that the drug was effective in inhibiting iPLA$_2$epsilon, iPLA$_2$zeta, and/or iPLA$_2$eta expression, a value is assigned to that modulation and is thereafter compared to the modulation of other drugs. In an aspect, a prioritization can be set up by comprising the magnitudes of the various respective modulations and a hierarchy of drugs can be established. From this, it is possible to establish a priority of work on the drugs.

In an aspect, the invention comprises a method for prioritizing the therapeutic capability of drugs of putative efficacy against obesity, comprising administering drugs to a living animal system which is actively expressing iPLA$_2$epsilon, iPLA$_2$zeta, and/or iPLA$_2$eta, measuring any modulation of the iPLA$_2$epsilon, iPLA$_2$zeta, and/or iPLA$_2$eta expression by a TAG or free fatty acid/glycerol analysis of an effect and determining if the modulation was an increase or a decrease or no change in iPLA$_2$epsilon, iPLA$_2$zeta, and/or iPLA$_2$eta expression level. If the modulation is determined to be a decrease then determining that the drug was effective in promoting iPLA$_2$epsilon, iPLA$_2$zeta, and/or iPLA$_2$eta expression, a value is assigned to that modulation and is thereafter compared to the modulation of other drugs. In an aspect, a prioritization can be set up by comprising the magnitudes of the various respective modulations and a hierarchy of drugs can be established. From this, it is possible to establish a priority of work on the drugs.

The present discovery includes a method and research tool for identifying substances which modulate iPLA$_2$zeta expression. In an aspect, the screening method and research tool comprises a screening method contacting a candidate substance with cells capably expressing iPLA$_2$zeta or a fragment thereof, and measuring the expression of iPLA$_2$zeta or a fragment thereof by the cells by an analysis of an effluent for the TAG content.

The present discovery includes a method and research tool for identifying substances which modulate iPLA$_2$eta expression. In an aspect, the screening method and research tool comprises a screening method contacting a candidate substance with cells capably expressing iPLA$_2$eta or a fragment thereof, and measuring the expression of iPLA$_2$eta or a fragment thereof by the cells by an analysis of an effluent for the TAG content.

BRIEF DESCRIPTION OF THE DRAWINGS

FIG. 1 depicts Amino Acid Sequence Alignment of Human iPLA$_2$epsilon (Adiponutrim; SEQ ID NO: 1), iPLA$_2$zeta (TTS-2.2; SEQ ID NO: 2), and iPLA$_2$eta (GS2; SEQ ID NO: 3). H$_x$ (SEQ ID NO: 30) denotes the position of the histidine tag where x=0 (no histidine tag) or an integer ranging from 4 to 12. For human iPLA$_2$epsilon(His)$_6$ (6xHis tag disclosed as SEQ ID NO: 29), iPLA$_2$zeta(His)$_6$ (6xHis tag disclosed as SEQ ID NO: 29), and iPLA$_2$eta(His)$_6$ (6xHis tag disclosed as SEQ ID NO: 29), x=6.

FIG. 7 depicts the Nucleotide Sequence (SEQ ID NO: 4) (and translated polypeptide sequence; SEQ ID NO: 6) of Human iPLA$_2$zeta (ITS-2.2).

FIG. 8 depicts the Nucleotide Sequence (SEQ ID NO: 5) (and translated polypeptide sequence; SEQ ID NO: 7) of Human iPLA$_2$eta (GS2).

FIG. 10 and FIG. 11 provide Nutleotide and Deduced Amino Acid Sequences of Our Newly Discovery Human Adiponutrin (iPLA$_2$epsilon) and variants thereof. A. Glu434 Variant (refSNP ID=2294918(g); Sequence ID+AK025665 (nucleotide)) B. Lys434 Variant (refSNP ID=2294918(a); Sequence ID=AL138578.2 (nucleotide): NP_079501 (protein)). The depicted nucleotide coding sequences (lower case letters) of human adiponutrin (1446 bp) encode for polypeptides of 481 amino acids (upper case letters). The amino acid encoded for each adiponutrin (iPLA$_2$epsilon) allelic variant is boxed. The conserved nucleotide binding (GCGFLG; SEQ ID NO: 12) and lipase (GASAG; SEQ ID NO: 13) consensus sequences are indicated with dashed and solid lines, respectively. The catalytic serine (Ser-47) is depicted to illustrate the native (where R=H) or acylated enzyme (where R=any fatty acyl moiety).

FIG. 10 and FIG. 11 show our novel nucleic acids and our novel enzymes herein as iPLA$_2$epsilon SEQ ID#'s are at the top of FIG. 10 and 11. SEQ ID NO. 9 is FIG. 10 (listed protein sequence); SEQ ID NO. 11 is FIG. 11 (listed protein sequence); SEQ ID NO. 8 is FIG. 10 (listed nucleotide sequence); and SEQ ID NO. 10 is FIG. 11 (listed nucleotide sequence) such variants are included herein as iPLA$_2$epsilon.

DETAILED DESCRIPTION OF THE INVENTION

Figure 2:
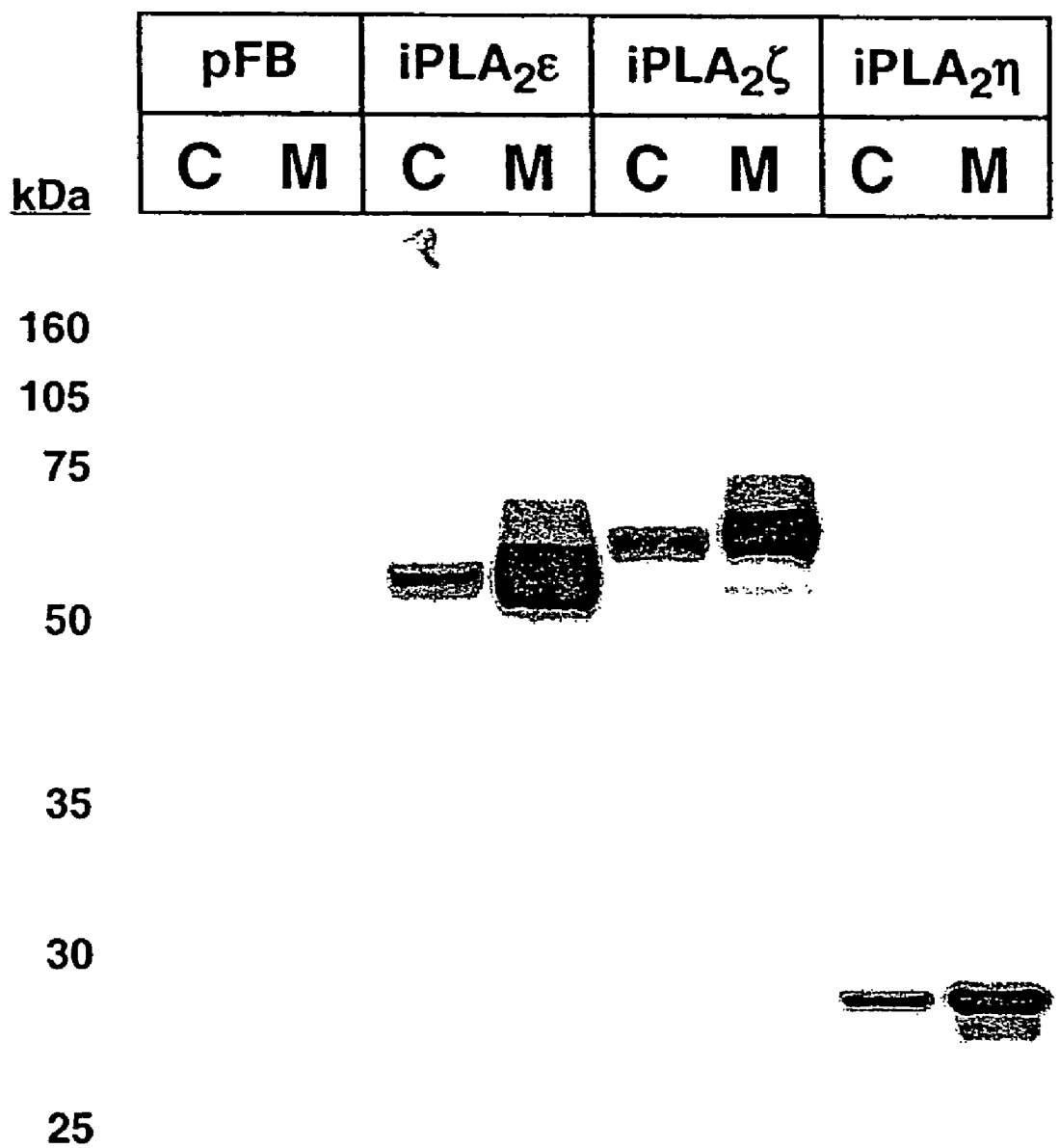
FIG. 2 depicts Western Analysis of the Expression and Subcellular Localization of Recombinant Human iPLA$_2$epsilon(His)$_6$ (6xHis tag disclosed as SEQ ID NO: 29, iPLA$_2$zeta(His)$_6$ (6xHis tag disclosed as SEQ ID NO: 29), and iPLA$_2$eta(His)$_6$ (6xHis tag disclosed as SEQ ID NO: 29) in Sf9 Cells.

This invention relates generally to the identification of phospholipases A$_2$/nonhormone sensitive lipases (HSL) in triacylglycerol lipase activities and transacylase activities.

Sequence database searches for proteins containing calcium-independent phospholipase A$_2$ (iPLA$_2$) nucleotide (G/AxGxxG) and lipase (GxSxG) consensus motifs identified a novel subfamily of three putative iPLA$_2$ family members designated iPLA$_2$epsilon, iPLA$_2$zeta, and iPLA$_2$eta (adiponutrin, TTS-2.2, and GS2, respectively) of previously unknown catalytic function. Herein, we describe the cloning, heterologous expression, and affinity purification of the three human isoforms of this iPLA$_2$ subfamily in Sf9 cells and demonstrate that each possesses abundant TAG lipase activity. Moreover, iPLA$_2$epsilon, iPLA$_2$zeta, and iPLA$_2$eta also possesses acylglycerol transacylase activity utilizing mono-olein as an acyl donor which, in the presence of mono-olein or diolein acceptors, results in the synthesis of diolein and tri-olein, respectively. (E)-6-(bromomethylene)-3-(1-naphthale-nyl)-2H tetrahydro-pyran-2-one (BEL), a mechanism-based suicide substrate inhibitor of all known iPLA$_2$s, inhibits the triglyceride lipase activity of each of the three isofoms similarly (IC$_{50}$=0.1-0.5 microM). Quantitative PCR revealed dramatically increased expression of iPLA$_2$zeta and iPLA$_2$eta transcripts in differentiating 3T3-L1 adipocytes and identified the presence of all three iPLA$_2$ isoforms in human SW872 liposarcoma cells. Collectively, these results identify three novel TAG lipases/acylglycerol transacylases that likely participate in TAG hydrolysis and the acyl-CoA independent transacylation of acylglycerols, thereby facilitating energy mobilization and storage in adipocytes.

In an aspect, the invention provides for the first time isolated novel and purified and characterized phospholipases A$_2$, referred to herein as calcium-independent lipases A$_2$zeta (iPLA$_2$zeta) having SEQ ID NO: 2 (See FIG. 1) and nucleic acid sequence SEQ ID NO: 4 (See FIG. 7), and calcium-independent lipases A$_2$eta (iPLA$_2$eta) having SEQ ID NO: 3 (See FIG. 1) and nucleic acid sequence SEQ ID NO: 5 (See FIG. 8). For the first time herein, these novel enzymes has been isolated and characterized and is involved in the catalysis (hydrolysis) and synthesis (transesterification) of lipids in a living mammalian cell. Moreover, these enzymes, iPLA$_2$zeta, and iPLA$_2$eta, through the process of transesterification can catalyze the net anabolic synthesis of triglycerides through a variety of metabolic precursor's (e.g. monoacylglycerol, diacylglycerol and acyl CoA).

Further, the inventors have discovered a medical treatment for combating obesity and over-weightness in humans which comprises effectively administering an inhibiting amount of a compound which promotes (increases) or blocks (inhibits) human iPLA$_2$epsilon, iPLA$_2$zeta, and/or iPLA$_2$eta expression or enzymatic activity in a living cell.

The inventors have discovered a screening method and research tool for identifying drugs which are useful to successfully hold weight in a living mammal or if desired to reduce weight gain.

As used herein the term "putative" means deemed to be, supposed, reputed to be an inhibitor (repressor) of the expression of iPLA$_2$zeta in iPLA$_2$zeta expressible tissue such as in adipose tissue of a transgenic mouse or a sample tissue thereof or a sample adequately representative thereof.

As used herein the term "putative" means deemed to be, supposed, reputed to be an inhibitor (repressor) of the expression of iPLA$_2$eta in iPLA$_2$eta expressible tissue such as in adipose tissue or sample tissue thereof or a sample adequately representative thereof.

As used herein, the term "compound" includes cell(s), compounds, irons/anions, cations and salts.

As used herein, the term "tissue" includes tissue, cells and collections of a multiplicity of homogenous or nearly homogenous cell lines or a sample thereof or a representative sample thereof. In an aspect the tissue is a living mammalian tissue such as in a tissue culture or living mammal or in a living transgenic mouse.

As used herein, the term "peptide" is any of a group of compounds comprising two or more amino acids linked by chemical bonding between their respective carboxyl and amino groups. The term "peptide" includes peptides and proteins that are of sufficient length and composition to affect a biological response, e.g. antibody production or cytokine activity whether or not the peptide is a hapten. The term "peptide" includes modified amino acids, such modifications including, but not limited to, phosphorylation, glycosylation, acylation, prenylation, lipidation and methylation.

As used herein, the term "polypeptide" is any of a group of natural or synthetic polymers made up of amino acids chemically linked together such as peptides linked together. The term "polypeptide" includes peptide, translated nucleic acid and fragments thereof.

As used herein, the term "polynucleotide" includes nucleotide sequences and partial sequences, DNA, cDNA, RNA variant isoforms, splice variants, allelic variants and fragments thereof.

As used herein, the terms "protein", "polypeptide" and "peptide" are used interchangeably herein when referring to a translated nucleic acid (e.g. a gene product). The term "polypeptide" includes proteins. The term "protein" includes the native (or wild-type) protein as well as a histidine-tagged protein. The term "protein" includes histidine-tagged proteins in which the number of histidine residues ranges from 4 to 12.

As used herein, the term "isolated polypeptide" includes a polypeptide essentially and substantially free from contaminating cellular components.

As used herein, the term "isolated protein" includes a protein that is essentially free from contamination cellular components normally associated with the protein in nature.

As used herein, the term "nucleic acid" refers to oligonucleotides or polynucleotides such as deoxyribonucleic acid (DNA) and ribonucleic acid (RNA) as well as analogs of either RNA or DNA, for example made from nucleotide analogs any of which are in single or double stranded form.

As used herein, the term "patient" and subject" are synonymous and are used interchangeably herein.

As used herein, the term "expression" includes the biosynthesis of a product as an expression product from a gene such as the transcription of a structural gene into mRNA and the translation of mRNA into at least one peptide or at least one polypeptide.

As used herein, the term "mammal" includes living animals including humans and non-human animals such as murine, porcine, canine and feline.

As used herein, the term "sample" means a viable sample of biological tissue or fluid and is not limited to adipose tissue. Biological samples may include representative sections of tissues.

As used herein, the term "target protein" includes an amino acid sequence expressed in a target cell such as in an adipocyte. In an aspect, the target protein is a protein having a sequence shown in SEQ. ID. NO: 1, SEQ. ID. NO: 2 or SEQ. ID. NO: 3.

As used herein, the term "antisense" means a strand of RNA whose sequence of bases is complementary to messenger RNA.

As used herein, the term "siRNA" means short interfering RNA.

The phrase "a sequence encoding a gene product" refers to a nucleic acid that contains sequence information, e.g., for a structural RNA such as rRNA, a tRNA, the primary amino acid sequence of a specific protein or peptide, a binding site for a transacting regulatory agent, an antisense RNA or a ribozyme. This phrase specifically encompasses degenerate codons (i.e., different codons which encode a single amino acid) of the native sequence or sequences which may be introduced to conform with codon preference in a specific host cell.

By "host cell" is meant a cell which contains an expression vector and supports the replication or expression of the expression vector. Host cells may be prokaryotic cells such as E. coli, or eukaryotic cells such as yeast, insect, amphibian, (e.g. Xenopus), or mammalian cells such as HEK293, CHO, HeLa and the like.

As used herein a "therapeutic amount" is an amount of a moiety such as a drug or compound which produces a desired or detectable therapeutic effect on or in a mammal administered with the moiety.

The term "recombinant" when used with reference to a cell, or protein, nucleic acid, or vector, includes reference to a cell, protein, or nucleic acid, or vector, that has been modified by the introduction of a heterologous nucleic acid, the alteration of a native nucleic acid to a form not native to that cell, or that the cell is derived from a cell so modified. Thus, for example, recombinant cells express genes and proteins that are not found within the native (non-recombinant) forms of the cell or express native genes that are otherwise abnormally expressed, under expressed or not expressed at all.

An "expression vector" is a nucleic acid construct, generated recombinantly or synthetically, with a series of specific nucleic acid elements which permit transcription of a particular nucleic acid in a host cell. The expression vector can be part of a plasmid, virus, or nucleic acid fragment. Typically, the expression vector includes a nucleic acid to be transcribed operably linked to a promoter.

Genetic knockout of hormone sensitive lipase (HSL) in mice has implicated the presence of other intracellular triacylglycerol (TAG) lipases mediating TAG hydrolysis in adipocytes. Sequence database searches for proteins containing calcium-independent phospholipase $A_2$ (iPLA$_2$) nucleotide (G/AxGxxG) and lipase (GxSxG) consensus motifs identified a novel subfamily of three putative iPLA$_2$ family members designated iPLA$_2$epsilon, iPLA$_2$zeta, and iPLA$_2$eta (adiponutrin, TTS-2.2, and GS2, respectively) of previously unknown catalytic function. Herein, we describe the cloning, heterologous expression, and affinity purification of the three human isoforms of this iPLA$_2$ subfamily in Sf9 cells and demonstrate that each possesses abundant TAG lipase activity.

Moreover, iPLA$_2$epsilon, iPLA$_2$zeta, and iPLA$_2$eta also possesses acylglycerol transacylase activity utilizing mono-olein as an acyl donor which, in the presence of mono-olein or diolein acceptors, results in the synthesis of diolein and tri-olein, respectively. (E)-6-(bromomethylene)-3-(1-naphthalenyl)-2Htetrahydropyran-2-one (BEL), a mechanism-based suicide substrate inhibitor of all known iPLA$_2$s, inhibits the triglyceride lipase activity of each of the three isoforms similarly (IC$_{50}$=0.1-0.5 microM). Quantitative PCR revealed dramatically increased expression of iPLA$_2$epsilon and iPLA$_2$zeta transcripts in differentiating 3T3-L1 adipocytes and identified the presence of all three iPLA$_2$ isoforms in human SW872 liposarcoma cells. Collectively, these results identify three novel TAG lipases/acylglycerol transacylases that likely participate in TAG hydrolysis and the acyl-CoA independent transacylation of acylglycerols, thereby facilitating energy mobilization and storage in adipocytes.

Obesity and its associated clinical sequelae (e.g. type 2 diabetes, atherosclerosis, and hypertension) represent the major and most rapidly expanding health epidemic in industrialized nations (1-4). Obesity results from an abnormal increase in white adipose tissue mass, primarily in the form of triglycerides, and, in humans, is thought to be caused by a complex array of genetic, environmental and hormonal factors (1,4). Under conditions of obesity, serum non-esterified fatty acids are elevated, contributing to the accumulation of triglycerides in non-adipose tissues (e.g. hepatic, myocardial, and pancreatic) and to the development of the type 2 metabolic syndrome (5). The combined effects of excess cellular triglycerides, fatty acyl-CoAs, and free fatty acids are believed to be primary mediators of the lipotoxic effects of obesity which include decreased insulin sensitivity, increased oxidative stress, reduced metabolic capacity, and increased rates of apoptosis in multiple organ systems (5-8).

Triacylglycerol/fatty acid recycling is an important mechanism by which adipocytes modulate fatty acyl flux in response to changing metabolic conditions (9,10). The TAG metabolic cycle encompasses both de novo triacylglycerol synthesis, which is thought to be mediated primarily through the concerted activities of glycolytic/glyceroneogenic enzymes, acyl-CoA dependent acyltransferases, and phosphatidic acid phosphatases (10-12), and TAG hydrolysis catalyzed by triacylglycerol lipases. Hormone sensitive lipase (HSL) was the first intracellular lipase to be purified and cloned (13), having since been extensively characterized in terms of its substrate selectivity and mechanisms of regulation (14,15). Results from these studies have emphasized the role of this enzyme in meeting increased systemic demand for free fatty acids through its activation by phosphorylation by protein kinase A (16-18), the exbracellular signal-regulated kinase pathway (19) and/or by interactions with various proteins partners (14,15). Genetic knockout of HSL in mice has revealed that HSL catalyzes the rate determining step in the hydrolysis of adipose tissue diacylglycerol (DAG) since DAG, but not TAG, accumulates in these animals (20). Furthermore, TAG is hydrolyzed less efficiently than DAG by HSL in in vitro assays (16) and measurement of TAG lipase activity in adipose tissue of HSL knockout mice demonstrates the existence of other as yet unknown TAG lipase(s) (20-23).

Although the biosynthesis of triglycerides is believed to be mediated primarily by an array of acyl-CoA-dependent enzymes in pathways utilizing either glycerol phosphate, dihydroxyacetone phosphate, or monoacylglycerol as initial acyl acceptors, the relative contribution of acyl-CoA independent transacylases utilizing mono- and diacylglycerols as acyl donors/acceptors in the synthesis of cellular TAG is largely unknown. Intestinal enterocytes contain an sn-1,2(2,3)-diacylglycerol transacylase which has been suggested to be important for the acyl-CoA independent transacylation of monoacylglycerol and diacylglycerol leading to the production of triacylglycerol for incorporation into chylomicrons (24,25). However, despite the apparent importance of acylglycerol transacylation in intestinal lipid transport and non-HSL TAG lipases in adipocyte lipid homeostasis, the molecular identities of the polypeptides catalyzing these reactions is currently unknown.

In the process of searching for novel calcium-independent phospholipases $A_2$ by protein sequence homology searches for candidate enzymes containing the $iPLA_2$ dual signature nucleotide (G/AxGxxG) and active site lipase (GxSxG) motifs, we identified a subfamily of putative $iPLA_2$ enzymes (previously named adiponutrin, TTS-2.2, and GS2) of previously unknown catalytic function which each contain an N-terminal patatin ($iPLA_2$alpha) homology domain as determined by protein family analysis (FIG. 1). One of these proteins, adiponutrin, has received much attention as an adipocyte specific protein which is downregulated by either fasting (26) or treatment with thiazolodinediones (27) and is acutely upregulated by re-feeding a high carbohydrate (26, 28) or high protein diet (29). Moreover, mouse adiponutrin mRNA is dramatically up-regulated during 3T3-L1 adipocyte differentiation (26) and TTS-2.2 has been shown to be associated with lipid droplets in CHO K2 cells (30).

In this application, we describe the cloning, heterolgous expression, and affinity purification of human $iPLA_2$epsilon (adiponutrin), $iPLA_2$zeta (TTS-2.2), and $iPLA_2$eta (GS2) in Sf9 cells. Furthermore, we demonstrate that the expressed recombinant enzymes hydrolyze triolein and are able to transfer the donor acyl moiety of mono-olein to mono-olein or diolein acceptors to form diolein or triolein, respectively. Expression of $iPLA_2$zeta message is markedly upregulated during 3T3-L1 differentiation and parallels the dramatic induction of $iPLA_2$epsilon expression in this cell line. In addition, all three $iPLA_2$ mRNAs are present in human liposarcoma cells. Collectively, these results identify a novel class of triglyceride lipaseltransacylase enzymes which likely participate in adipocyte triglyceride fatty acyl liberation, recycling, and lipid homeostasis.

Exemplary embodiments are described in the following examples. It is intended that the specification, together with the examples, be considered exemplary only.

EXAMPLES

Materials—Grace's insect medium and Bac-to-Bac baculoviral system reagents were obtained from Invitrogen. Restriction enzymes were purchased from Roche. Nucleotide sequencing was performed by the Nucleic Acid Chemistry Laboratory at Washington University. 1-palmitoyl-2-[1-$^{14}$C]-oleoyl-sn-glycerol-3-phosphocholine, and [1-$^{14}$C]-oleoyl-glycerol were purchased from American Radiolabeled Chemicals. [9,10-$^3$H(N)]-triolein was obtained from Perkin Elmer and was re-purified before use utilizing a Vydac C18 Pharmaceutical HPLC column equilibrated with acetonitrile/dichloromethane (55:45) as the mobile phase. BEL was obtained from Cayman Chemical. Most other reagents were purchased from Fisher Scientific or Sigma.

Cloning of Human $iPLA_2$epsilon (Adiponutrin), $iPLA_2$zeta (TTS-2.21), and $iPLA_2$eta (GS2)—Human adipocyte Marathon-Ready cDNA (Clontech) was used as a template for PCR to obtain full-length CDNA for $iPLA_2$epsilon. PCR primers were designed to introduce a 5' Kozak sequence, a C-terminal 6xHis tag (SEQ ID NO: 29) at the 3'-end of the $iPLA_2$ coding sequence and to incorporate EcoR1 and Sall restriction sites for subcloning into the baculoviral expression vector pFASTBacI. Full-length human $iPLA_2$zeta (TTS-2.2) and $iPLA_2$eta (GS2) were amplified by PCR (with primers to introduce 5' Kozak sequences) from ATCC IMAGE clones 4875483 and 4717901, respectively and subcloned into pcDNAV5HisB. The insert including the in-frame 3' (His)$_6$ (SEQ ID NO: 29) coding sequence was then excised from this vector utilizing BamH1 and Pmel restriction sites for ligation into the baculoviral expression vector pFASTBacI. After sequencing the insert and flanking sequences on both strands of the $iPLA^2$-pFASTBacI constructs to ensure the sequence integrity of the construct, a bacrnid construct was prepared using the Bac-to-Bac Baculovirus Expression System protocol (Invitrogen) for subsequent Cellfectin-mediated transfection of Sf9 cells in 35 mm plates to produce infectious recombinant baculovirus. Amplified recombinant baculovirus was then used to infect a spinner culture of Sf9 cells for 72 h and the supernatant was collected as a high titer viral stock.

Expression of Human $iPLA_2$epsilon(His)$_6$ (6xHis tag disclosed as SEQ ID NO: 29), $iPLA_2$zeta(His)$_6$ (6xHis tag disclosed as SEQ ID NO: 29) and $iPLA_2$eta(His)$_6$ (6xHis tag disclosed as SEQ ID NO: 29) in Sf9 cells and Subcellular Fractionation-Sf9 cells (100 ml culture volume) at a density of approximately $1 \times 10^6$ cells/ml were infected with either control baculovirus or recombinant baculovirus encoding human $iPLA_2$epsilon(His)$_6$ (6xHis tag disclosed as SEQ ID NO: 29), $iPLA_2$zeta(His)$_6$ (6xHis tag disclosed as SEQ ID NO: 29) and $iPLA_2$eta(His)$_6$ (6xHis tag disclosed as SEQ ID NO: 29) at an multiplicity of infection of approximately 1. Forty-eight hours post-infection, cells were harvested by centrifugation (900 rpm×10 mm), washed once in Grace's insect medium without serum, re-pelleted, and resuspended in 10 ml lysis buffer (25 mM sodium phosphate, pH 7.8 containing 20% glycerol and 2 mM 2-mercaptoethanol). Cells were lysed by sonication (30×1 s bursts at 40% power) and centrifuged at 100,000×g for 1 h to separate cytosolic and membrane fractions. Cellular membranes were resuspended in a volume of lysis buffer equivalent to the volume of the cytosol fraction.

$Co^{2+}$-Affinity Column Chromatography of $iPLA_2$epsilon (His)$_6$ (6xHis tag disclosed as SEQ ID NO: 29), $iPLA_2$zeta (His)$_6$ (6xHis tag disclosed as SEQ ID NO: 29) and $iPLA_2$eta (His)$_6$ (6xHis tag disclosed as SEQ ID NO: 29). The cytosolic fraction (30 ml obtained from 300 ml of cultured Sf9 cells) containing recombinant human $iPLA_2$epsilon(His)$_6$ (6xHis tag disclosed as SEQ ID NO: 29), $iPLA_2$zeta(His)$_6$ (6xHis tag disclosed as SEQ ID NO: 29) or $iPLA_2$eta(His)$_6$ (6xHis tag disclosed as SEQ ID NO: 29) was mixed by inversion with 3 ml of TALON-$Co^{2+}$ resin for 1 h at 4° C. The resin-cytosol suspension was then poured into an empty Pharrnacia column (1.5×10 cm) and washed with 10 column volumes of lysis buffer containing 500 mM NaCl (Buffer A). Recombinant iPLA$_2$ His-tagged proteins were eluted utilizing a gradient of imidazole (250 mM final concentration) in 50 ml of Buffer A. Fractions were collected and assayed for phospholipase A$_2$ and triolein lipase activity as described below.

Assay for Calcium-Independent Phospholipase A$_2$ Activity—Sample fractions were incubated in 100 mM Tris-HCl, pH 7.2 containing 4 mM EGTA (200 microliters final volume) for 5 min at 37° C. in the presence of 1-palmitoyl-2-[1-$^{14}$C]-oleoyl-sn-glycero-3-phosphocholine introduced by ethanolic injection. Reactions were terminated by addition of 100 microliters of butanol and extraction of the radiolabeled product and remaining substrate into the butanol layer by vigorous vortexing. Samples were spotted on LK6 Silica Gel 60 Å TLC plates, overlaid with oleic acid standard, dried, and developed in petroleum ether/ethyl ether/acetic acid (70:30:1). The region of the plate corresponding to the oleic acid standard (visualized by iodine staining) was scraped into scintillation vials and quantified by liquid scintillation spectrometry.

Assay for Triolein Lipase Activity—Sample fractions were incubated in 85 mM potassium phosphate, pH 7.0 containing 2 mM EDTA and 2 mM DTT for 15 min at 37° C. in the presence of a suspension of 100 microM [9,10-$^3$H(N)]-triolein (100 microCi/micromol) in 25 microM egg yolk lecithin, and 100 microM sodium taurocholate. In some reactions, BEL was added at the indicated concentrations and incubated with enzyme at room temperature for 3 min prior to the addition of radiolabeled substrate. After extraction of radiolabeled reaction products and remaining substrate into butanol, samples were spotted on TLC plates, overlaid with oleic acid standard, dried, and developed in chloroforml-methanol/NH$_4$OH (65:25:5). The region of the plate corresponding to the oleic acid standard (visualized by iodine staining) was scraped into scintillation vials and quantified by liquid scintillation spectrometry.

Assay for Acylglycerol Transacylase Activity—Highly purified $CO^{2+}$-TALON affinity chromatographic fractions containing iPLA$_2$epsilon(His)$_6$ (6xHis tag disclosed as SEQ ID NO: 29), iPLA$_2$zeta(His)$_6$ (6xHis tag disclosed as SEQ ID NO: 29) or iPLA$_2$eta(His)$_6$ (6xHis tag disclosed as SEQ ID NO: 29) (40 microliters) were incubated in 85 mM potassium phosphate, pH 7.0 (200 microliters final volume) for 15 mm at 37° C. in the presence of 10 microM [1-$^{14}$-C]-mono-olein (acyl donor), 25 microM acyl acceptor (mono-olein or diolein), 25 microM egg yolk lecithin, and 25 microM sodium taurocholate. After extraction of radiolabeled reaction products and remaining substrate into butanol, samples were spotted on TLC plates, overlaid with trileiddiolein standards, dried, and developed in petroleum ether/ethyl ether/acetic acid (75:25:1). The regions of the plate corresponding to either the diolein, triolein, and fatty acid standards (visualized by iodine staining) were scraped into scintillation vials and quantified by liquid scintillation spectrometry.

Quantitative PCR of iPLA$_2$epsilon, iPLA$_2$zeta and iPLA$_2$eta. Message in Differentiating 3T3-1 Adipocytes and SW872 Human Liposacrcoma Cells—3T3-L1 pre-adipocytes were cultured and differentiated as previously described (31). Human SW872 liposarcoma cells were cultured as previously described (32). 3T3-E1 cells at day 0 through day 6 of differentiation (2 day intervals) or SW872 cells were washed twice with ice-cold phosphate buffered saline and RNA was prepared following the RNeasy (Qiagen) protocol as described by the manufacturer. RNA (0.1-2 micrograms) was reverse transcribed using MultiScribe reverse transcriptase (TaqMan Gold RT-PCR kit, Applied Biosystems) by incubation for 10 min at 25° C. followed by 30 min at 48° C. and a final step of 5 min at 95° C. 20 ng of the resultant cDNA was used for each quantitative polymerase chain reaction. Primer/probe sets for quantitative PCR were designed using Primer Express software from PE Biosystems. Probes were 5' labeled with reporter dye FAM (6-carboxylfluorescein), and 3' labeled with quenching dye, TAMRA (6-carboxytetramethylrhodamine). Human iPLA$_2$epsilon forward (5'-GGCAAAATAGGCATCTCTCTT-ACC-3'; SEQ ID NO: 14) and reverse (5'-GGAGGGATAAGGCCACTGTAGA-3'; SEQ ID NO: 15) primers were paired with probe (5'-AACAT-ACCAAGGCATCCACGACTTCGTC-3'; SEQ ID NO: 16). Human iPLA$_2$zeta forward (5'-ACTGCACGCGGTCAC-CTT-3'; SEQ ID NO: 17) and reverse (5'-CACGAGGTC-CATGAGGATCTC-3'; SEQ ID NO: 18) primers were paired with probe (5'-TGTGCAGTCT-CCCTCTCGGCCG-TATAAT-3'; SEQ ID NO: 19). Human iPLA$_2$eta forward (5'-GCACAGAAAATGAGGATTATTAAAGG-3'; SEQ ID NO: 20) and reverse (5'-CGCTGCAAATGATAGGT-TGATG-3'; SEQ ID NO: 21) primers were paired with probe (5'-TGCTTCATTCTAGCTGTAGCACTGCGAGCAAC-3'; SEQ ID NO: 22). Mouse iPLA$_2$epsilon forward (5'-ACTG-CACGCGGTCACCTT-3'; SEQ ID NO: 23) and reverse (5'-CACGAGGTCCATGAGGATCTC-3'; SEQ ID NO: 24) primers were paired with probe (5'-TGTGCAGTCTC-CCTCTCGGCCGTATAAT-3'; SEQ ID NO: 25). Mouse iPLA$_2$zeta forward (5'-GCCACAGCGCTGGTCACT-3'; SEQ ID NO: 26) and reverse (5'-CCTCCTTGGACACCT-CAATAATG-3'; SEQ ID NO: 27) primers were paired with probe (5'-CCTGCCTGGGTGAAGCAGGTGC-3'; SEQ ID NO: 28). Quantitative PCR was carried out using TaqMan PCR reagents (Applied Biosystems) as recommended by the manufacturer with GAPDH primers and probe as an internal standard. Each PCR amplification was performed in triplicate for 2 min at 50° C., 10 min at 95° C., followed by 40 cycles of 15 s at 95° C. and 1 min at 60° C.

Other Methods—Proteins were separated by SDS-PAGE according to the method of Laemmli (33). For Western analyses, the separated proteins in SDS-PAGE gels were transferred to polyvinylidene difluoride membranes and subsequently probed with a mouse monoclonal anti-His$_6$ antibody (BD Biosciences) in conjunction with an anti-mouse IgG-horseradish peroxidase conjugate. Protein concentrations were determined by the Bradford protein assay (Bio-Rad) using bovine serum albumin as standard.

Results

Figure 3:
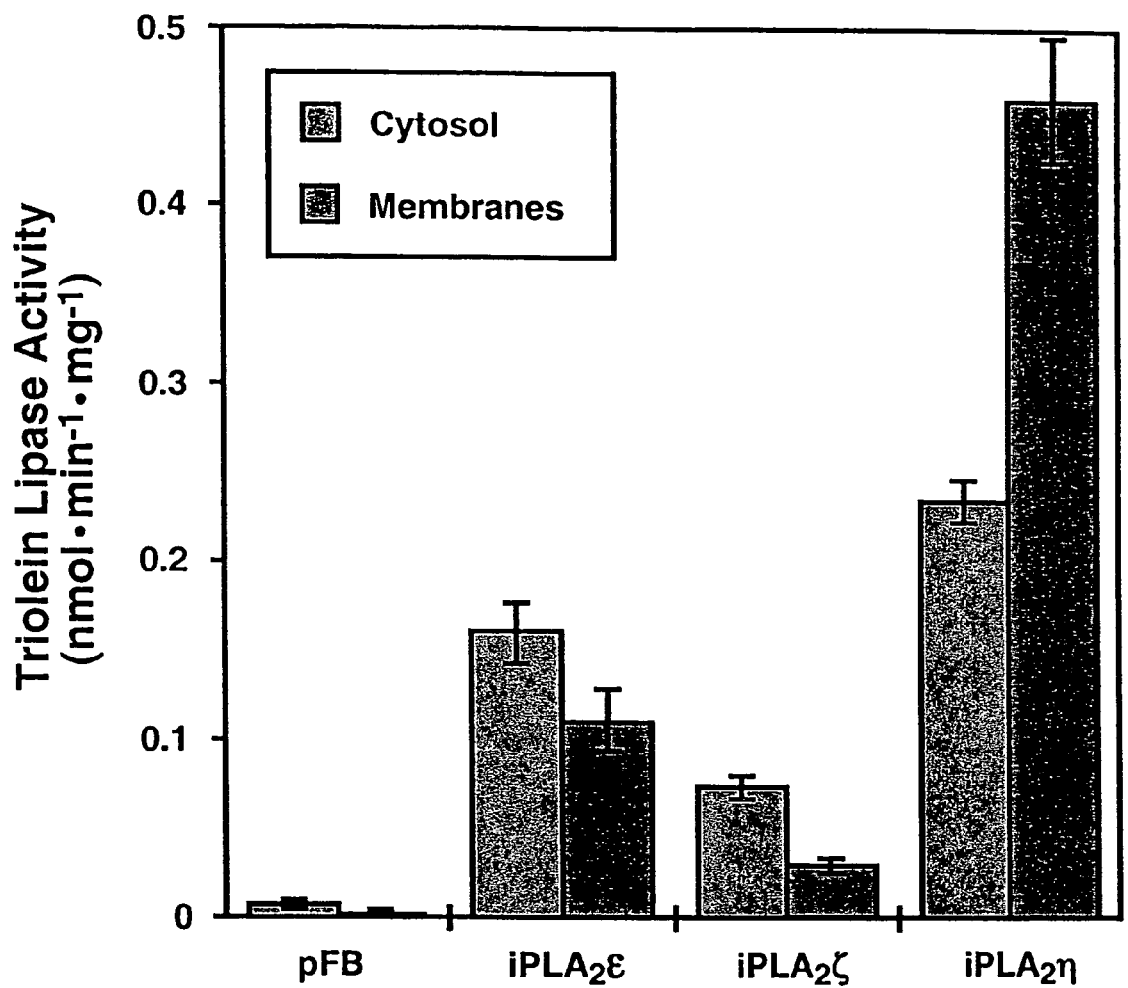
FIG. 3 depicts Triolein Lipase Activity of Sf9 Subcellular Fractions Containing Recombinant Human iPLA$_2$epsilon (His)$_6$ (6xHis tag disclosed as SEQ ID NO: 29), iPLA$_2$zeta (His)$_6$ (6xHis tag disclosed as SEQ ID NO: 29), and iPLA$_2$eta (His)$_6$ (6xHis tag disclosed as SEQ ID NO: 29).

Searches of the protein sequence database for novel iPLA$_2$ family members possessing both nucleotide (G/AxGxxG) and lipase (GxSxG) consensus motifs identified a group of three human proteins (adiponutrin, TTS-2.2, and GS2) which contained patatin (iPLA$_2$alpha) homology domains (FIG. 1). On the basis of their similarity to iPLA$_2$alpha, we designated adiponutrin, TTS-2.2, and GS2 as iPLA$_2$epsilon, iPLA$_2$zeta, and iPLA$_2$eta, respectively. To determine if the presence of the dual signature nucleotide and lipase motifs of human iPLA$_2$epsilon, iPLA$_2$zeta, and iPLA$_2$eta proteins correctly identified novel lipase family members, we heterologously expressed each of the three C-terminal His$_6$-tagged proteins (6xHis tag disclosed as SEQ ID NO: 29) individually in an Sf9 cell baculovirus expression system. Western analysis of Sf9 cells infected with baculoviruses encoding human either iPLA$_2$epsilon(His)$_6$ (6xHis tag disclosed as SEQ ID NO: 29), iPLA$_2$zeta(His)$_6$ (6xHis tag disclosed as SEQ ID NO: 29), or iPLA$_2$eta(His)$_6$ (6xHis tag disclosed as SEQ ID NO: 29 proteins revealed the presence of 53, 58, and 28 kDa (respectively) immunoreactive bands, corresponding to their predicted molecular weights, utilizing an anti-His$_6$ (6xHis tag disclosed as SEQ ID NO: 29) monoclonal antibody (FIG. 2). In contrast, these immunoreactive bands were not present in Sf9 cells infected with wild-type empty vector (pFB) baculovirus, Subcellular fractionation of the infected Sf9 cells demonstrated that the majority (70-90%) of the expressed iPLA$_2$epsilon(His)$_6$ (6xHis tag disclosed as SEQ ID NO: 29, iPLA$_2$zeta(His)$_6$ (6xHis tag disclosed as SEQ ID NO: 29), and iPLA$_2$eta(His)$_6$ (6xHis tag disclosed as SEQ ID NO: 29) proteins were associated with the membrane fraction (FIG. 3). The presence of apparently soluble forms of each of the proteins in the Sf9 cell cytosolic fraction simplified purification procedures (described below) since high concentrations of detergents utilized for solubilization are known to inhibit other iPLA$_2$ family members. Differences in the expression levels of iPLA$_2$epsilon, iPLA$_2$zeta, and iPLA$_2$eta could arise from multiple factors including altered rates of transcription, translation and/or differences in mRNA or protein stability.

As potential members of the iPLA$_2$ family of enzymes, iPLA$_2$epsilon(His)$_6$ (6xHis tag disclosed as SEQ ID NO: 29), iPLA$_2$zeta(His)$_6$ (6xHis tag disclosed as SEQ ID NO: 29, and iPLA$_2$eta(His)$_6$ (6xHis tag disclosed as SEQ ID NO: 29), expressed in Sf9 cells were initially assayed for iPLA$_2$ activity utilizing 1-palmitoyl-2-[1-$^{14}$C]-oleoyl-sn-glycerol-3-phosphocholine as substrate. Results from these experiments indicated that the cytosol and membrane fractions containing iPLA$_2$epsilon(His)$_6$ (6xHis tag disclosed as SEQ ID NO: 29) possessed modest calcium-independent PLA$_2$ activity (20-50 pmol·min$^{-1}$·mg protein$^{-1}$) relative to pFastBac control Sf9 subcellular fractions (data not shown). However, similar assays with iPLA$_2$zeta(His)$_6$ (6xHis tag disclosed as SEQ ID NO: 29), and iPLA$_2$eta(His)$_6$ (6xHis tag disclosed as SEQ ID NO: 29) did not yield detectable amounts of [1-$^{14}$C]-oleic acid released from 1-palmitoly-2-[1-$^{14}$C]-oleoyl-sn-glycerol-3-phosphocholine in comparison to control reactions. Inclusion of Ca$^{2+}$ and/or ATP (a known stabilizer and activator of iPLA$_2$β activity) did not measurably increase iPLA$_2$ activity relative to control samples. Subsequent experiments with affinity purified iPLA$_2$epsilon(His)$_6$ (6xHis tag disclosed as SEQ ID NO: 29), iPLA$_2$zeta(His)$_6$ (6xHis tag disclosed as SEQ ID NO: 29), and iPLA$_2$eta(His)$_6$ (6xHis tag disclosed as SEQ ID NO: 29) with 1-palmitoyl-2-[1-$^{14}$C]-linoleoyl-sn-glycerol-3-phosphocholine or 1-palmitoyl-2-[1-$^{14}$C]-arachidonyl-sn-glycerol-3-phosphocholine revealed phospholipase A$_2$ activity from 67 to 134 pmol·min$^{-1}$·mg protein $^{-1}$ (see below for details).

Since the founding member of the iPLA$_2$ family, patatin (iPLA$_2$alpha), hydrolyzes both phospho-and neutral lipid substrates (34,35) and is able to catalyze transesterification reactions (36), we believe that iPLA$_2$epsilon, iPLA$_2$zeta and iPLA$_2$eta might possess neutral lipid lipase and/or transacylase activity. Moreover, the similar positional location of the nucleotide and lipase motifs near the N-terminus (FIG. 1) and the induced expression of adiponutrin (iPLA$_2$epsilon) in either differentiating 3T3-L1 adipocytes (26) or rat adipose tissue following meal feeding (28,29) further suggested that triacylglycerol was a potential substrate for this polypeptide. To address this possibility, each of the cytosol and membrane fractions containing iPLA$_2$epsilon(His)$_6$ (6xHis tag disclosed as SEQ ID NO: 29), iPLA$_2$zeta(His)$_6$ (6xHis tag disclosed as SEQ ID NO: 29), and iPLA$_2$eta(His)$_6$ (6xHis tag disclosed as SEQ ID NO: 29) were incubated in the presence of a sonicated suspension of phosphatidylcholine, sodium taurocholate, and [$^3$H]-triolein at 37° C. for 15 min. Robust hydrolysis of [$^3$H]-triolein, as determined by the release of [$^3$H]-oleic acid, was observed in cytosolic and membrane fractions containing either iPLA$_2$epsilon, iPLA$_2$zeta, and iPLA$_2$eta isoforms in comparison to pFB control fractions which exhibited very low triolein lipase activity (FIG. 3). The iPLA$_2$epsilon (His)$_6$ (6xHis tag disclosed as SEQ ID NO: 29), and iPLA$_2$zeta(His)$_6$ (6xHis tag disclosed as SEQ ID NO: 29) cytosolic fractions possessed greater triolein lipase activity in comparison to their membrane counterparts which was surprising considering that the majority of protein mass was present in the membrane fraction as determined by Western analysis (FIG. 2). This difference in activity may reflect the presence of a membrane-associate inhibitor, substrate dilution, or more likely that a large percentage of the membrane associated iPLA$_2$epsilon(His)$_6$ (6xHis tag disclosed as SEQ ID NO: 29), and iPLA$_2$zeta(His)$_6$ (6xHis tag disclosed as SEQ ID NO: 29) is unable to effectively interact with the triolein substrate in this in vitro prepared emulsion. In contrast, the triolein lipase activities of the iPLA$_2$eta(His)$_6$ (6xHis tag disclosed as SEQ ID NO: 29) cytosolic and membrane fractions were more proportionate to the relative amount of immunoreactive protein in each fraction (FIGS. 2 and 3). Assuming similar degrees of immunoreactivity of the monoclonal His$_6$ (SEQ ID NO: 29) antibody toward the His-tagged proteins iPLA$_2$eta(His)$_6$ (6xHis tag disclosed as SEQ ID NO: 29) possesses approximately 5-10 fold greater triolein lipase measured specific activity relative to iPLA$_2$epsilon(His)$_6$ (6xHis tag disclosed as SEQ ID NO: 29), and iPLA$_2$zeta(His)$_6$ (6xHis tag disclosed as SEQ ID NO: 29) under the conditions employed (FIGS. 2 and 3). In addition, a large number of factors could contribute to different specific activities in vivo, including differential substrate presentation, subcellular localization, post-translational modifications, and protein-protein interactions.

Figure 4B:
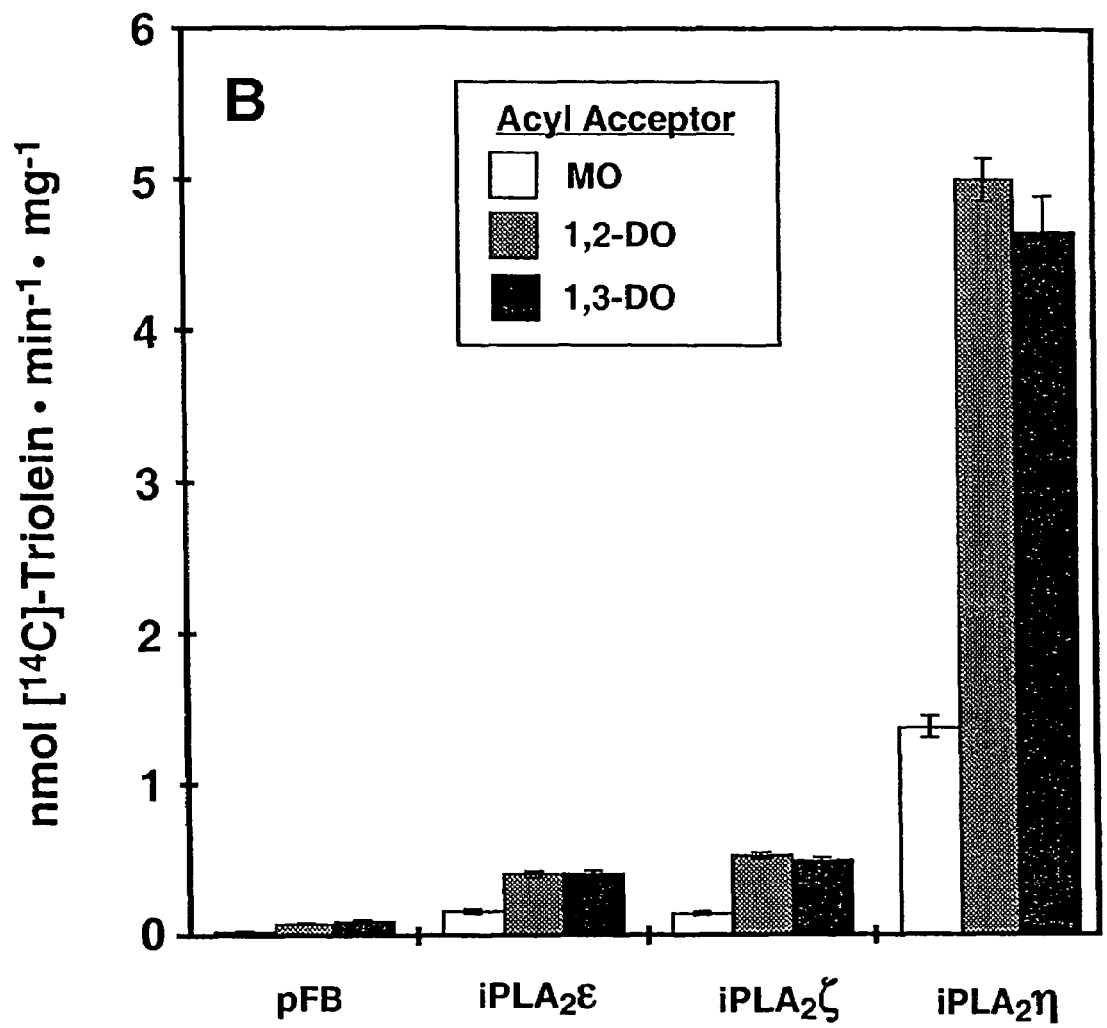
FIG. 4 depicts Affinity purified Human iPLA$_2$epsilon (His)$_6$ (6xHis tag disclosed as SEQ ID NO: 29), iPLA$_2$zeta (His)$_6$ (6xHis tag disclosed as SEQ ID NO: 29), and iPLA$_2$eta (His)$_6$ (6xHis tag disclosed as SEQ ID NO: 29) Catalyze Transacylation of Mono-olein to Form Diolein and Triolein.

Since patatin can catalyze ATP and acyl-CoA-independent transacylation reactions (34-36), we considered the possibility the iPLA$_2$epsilon, iPLA$_2$zeta, and iPLA$_2$eta may be involved in the cycling of acyl equivalents between triacylglycerol/diacylglycerol/monoacylglycerol pools. Accordingly, we sought to determine if the three members of this iPLA$_2$ subfamily could catalyze the transfer of the oleoly moiety from monoolein (donor) to a mono-olein or diolein acceptor to form diolein or triolein, respectively. To this end, we affinity purified each His-tagged iPLA$_2$ isoform utilizing co$^{2+}$ TALON affinity chromatography. The triolein lipase specific activities within peak fractions following elution of iPLA$_2$epsilon(His)$_6$ (6xHis tag disclosed as SEQ ID NO: 29), iPLA$_2$zeta(His)$_6$ (6xHis tag disclosed as SEQ ID NO: 29), and iPLA$_2$eta(His)$_6$ (6xHis tag disclosed as SEQ ID NO: 29) from the co$^{2+}$-charged TALON column were 8, 9 and 52 nmol oleic acid·min$^{-1}$·mg$^{-1}$ protein, respectively, under the conditions employed, representing an approximate 50 to 100-fold purification from the crude cytosol. Incubation of each of the affinity purified iPLA$_2$ His-tagged family members with [1-$^{14}$C]-mono-olein demonstrated the synthesis of radiolabeled diolein (FIG. 4A) which was not observed with pFB control column fractions. Consistent with the lipase activity measurements, affinity purified iPLA$_2$eta(His)$_6$ (6xHis tag disclosed as SEQ ID NO: 29) displayed approximately 10-fold greater transacylation specific activity than iPLA$_2$epsilon(His)$_6$ (6xHis tag disclosed as SEQ ID NO: 29), and iPLA$_2$zeta(His)$_6$ (6xHis tag disclosed as SEQ ID NO: 29) (FIGS. 4A and 4B). Remarkably, [$^{14}$C]-triolein was observed as product in these incubations (FIG. 4B) indicating that iPLA$_2$epsilon, iPLA$_2$zeta, and iPLA$_2$eta were each capable of catalyzing sequential transacylation reaction to form triolein (MOG+MOG→DOG+glycerol and MOG+DOG→TOG+ glycerol). Addition of exogenous 1,2- or 1,3 diolein as acyl acceptor increased the amount of [$^{14}$C]-triolein formed utilizing [1-$^{14}$C]-mono-olein as acyl donor in the presence of iPLA$_2$epsilon, iPLA$_2$zeta, and iPLA$_2$eta substantiating each transacylation reaction independently (FIG. 4B). Under the conditions examined, no detectable reference for either 1,2-diolein or 1,3-diolein as acyl acceptor for iPLA$_2$-catalyzed triolein synthesis were observed.

Although Sf9 cell cytosolic and membrane fractions containing iPLA$_2$zeta(His)$_6$ (6xHis tag disclosed as SEQ ID NO: 29), and iPLA$_2$eta(His)$_6$ (6xHis tag disclosed as SEQ ID NO: 29) did not display measurable iPLA$_2$ activity (above control samples) utilizing 1-palmitoyl-2-[1-$^{14}$C]-oleoyl-sn-glycerol-3-phosphocholine as substrate, we measure the PLA$_2$ activity of the affinity purified proteins with several different phospholipids substrates including those with polyunsaturated fatty acids at the sn-2 position. Incubation of iPLA$_2$epsilon (His)$_6$ (6xHis tag disclosed as SEQ ID NO: 29), iPLA$_2$zeta (His)$_6$ (6xHis tag disclosed as SEQ ID NO: 29), and iPLA$_2$eta (His)$_6$ (6xHis tag disclosed as SEQ ID NO: 29) with 1-palmitoyl-2-[1-$^{14}$C]-linoleoyl-sn-glycerol-3-phosphocholine or 1-palmitoly-2-[1-$^{14}$C]-arachidonly-sn-glycerol-3-phosphocholine for 30 min resulted in hydrolysis at rates of 57±3, 57±19, and 77±23 pmol linoleic acid·min$^{-1}$·mg protein$^{-1}$ or 100±4, 119±6 and 134±42 pmol arachidonic acid·min$^{31\ 1}$·mg protein$^{-1}$, respectively. We specifically point out that these results do not preclude the possibility that these iPLA$_2$ isoforms have greater phospholipase A$_2$ activity in vivo or in vitro with other phospholipid substrates, protein partners, or under different assay conditions.

Figure 5:
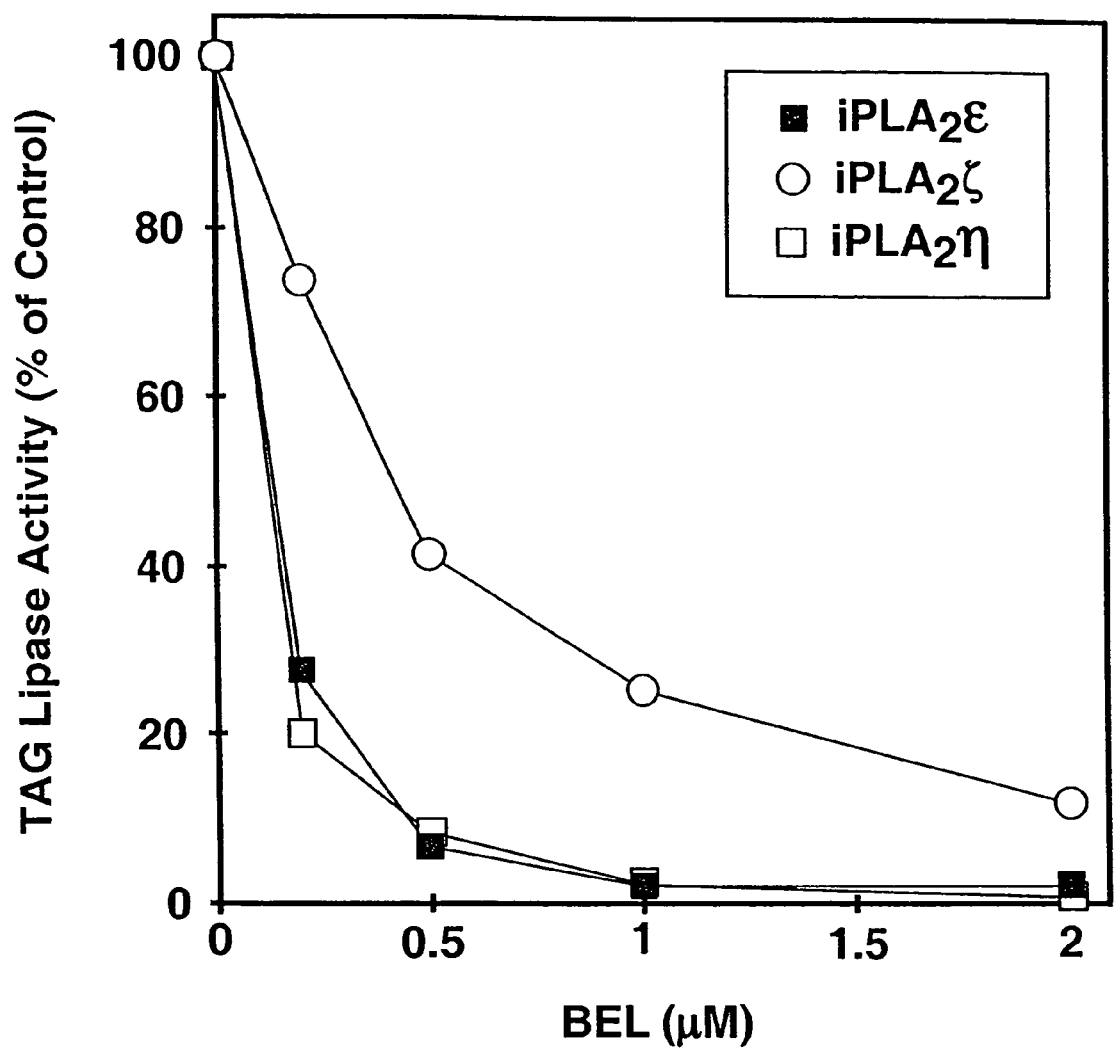
FIG. 5 depicts Inhibition of Recombinant Human iPLA$_2$epsilon(His)$_6$ (6xHis tag disclosed as SEQ ID NO: 29), iPLA$_2$zeta(His)$_6$ (6xHis tag disclosed as SEQ ID NO: 29), and iPLA$_2$eta(His)$_6$ (6xHis tag disclosed as SEQ ID NO: 29) Triolein Lipase Activity by (E)-6-(bromomethylene)-3-(1-naphthalenyl)-2H-tetrahydropyran-2-one (BEL).

The mechanism-based inhibitor (E)-6-(bromomethylene)-3-(1-naphthalenyl)-2H-tetrahydropyran-2-one (BEL) has been previously demonstrated to inhibit iPLA$_2$beta and iPLA$_2$gamma activity at sub to low micromolar concentrations (37-39). To determine whether the three new iPLA$_2$ family members were inhibitable by BEL, each enzyme was pre-incubated with 0.1-2 microM BEL or ethanol vehicle alone prior to measuring triolein lipase activity (FIG. 5). Remarkably, BEL is a highly potent inhibitor for iPLA$_2$epsilon (IC$_{50}$≈0.1 microM), iPLA$_2$zeta (IC$_{50}$≈0.5 microM), and iPLA$_2$eta (IC$_{50}$≈0.1 microM) (FIG. 5). Thus, iPLA$_2$epsilon, iPLA$_2$zeta, and iPLA$_2$eta are likely inhibited by BEL by a similar mechanism to that of iPLA$_2$beta and iPLA$_2$gamma. Considering the hydrophobic nature of the acyl-glycerol substrates of iPLA$_2$epsilon, iPLA$_2$zeta, and iPLA$_2$eta identified herein, it is not surprising that BEL would have access to the active sites of these enzymes.

Figure 6A:
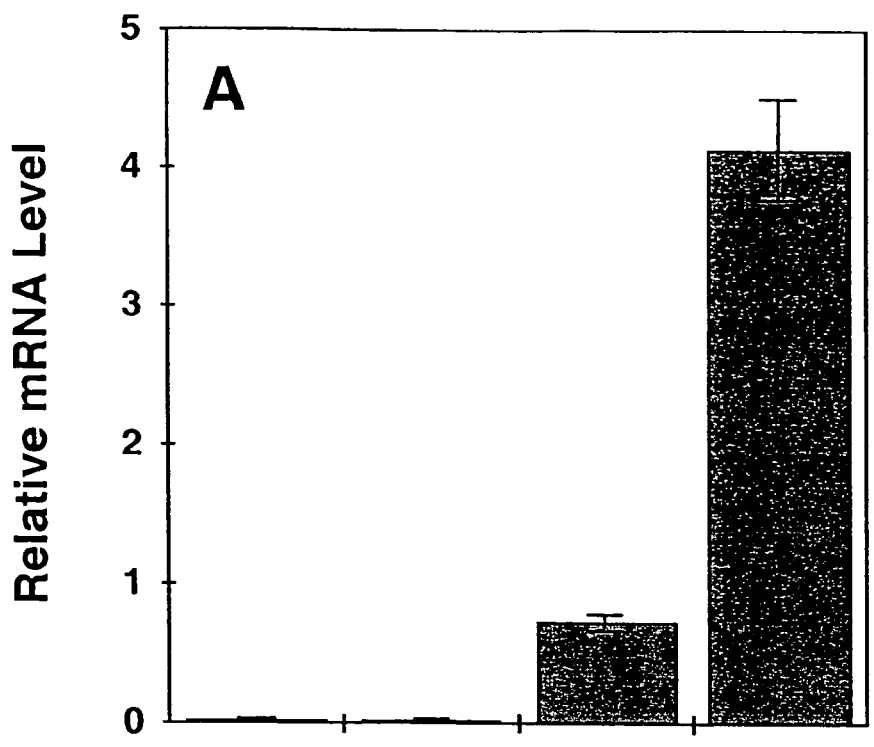
FIG. 6 depicts Quantitative PCR of iPLA$_2$epsilon and iPLA$_2$zeta Message in Mouse 3T3-L1 Preadipocytes and iPLA$_2$epsilon, iPLA$_2$zeta, and iPLA$_2$eta Message in Human SW872 Lipsarcoma Cells.
Figure 6:
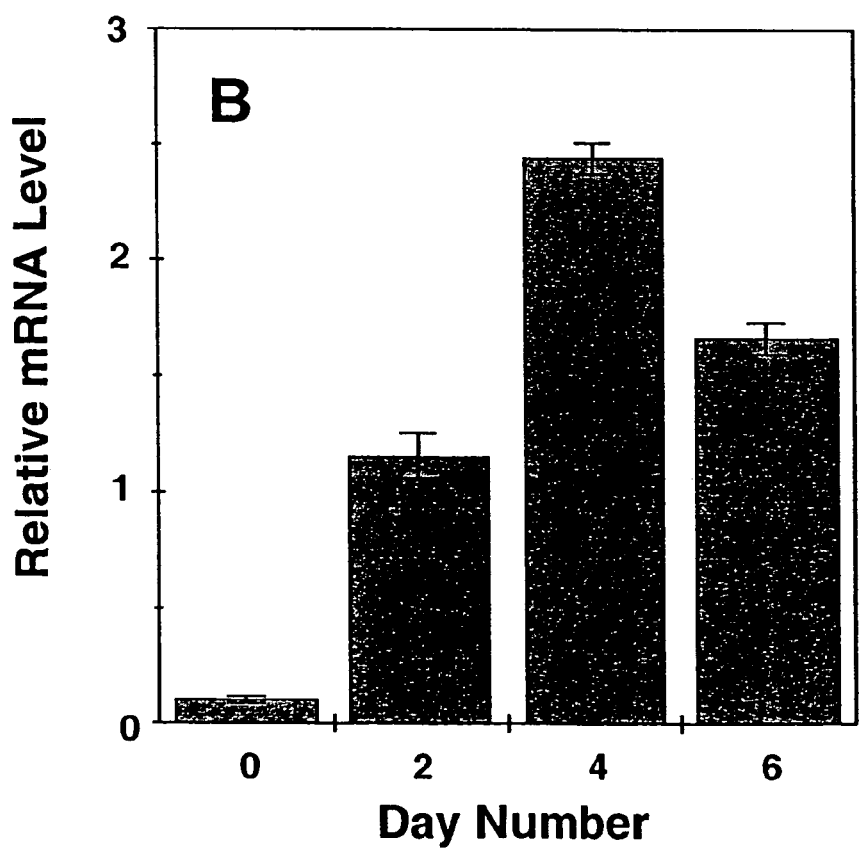
Figure 6C:
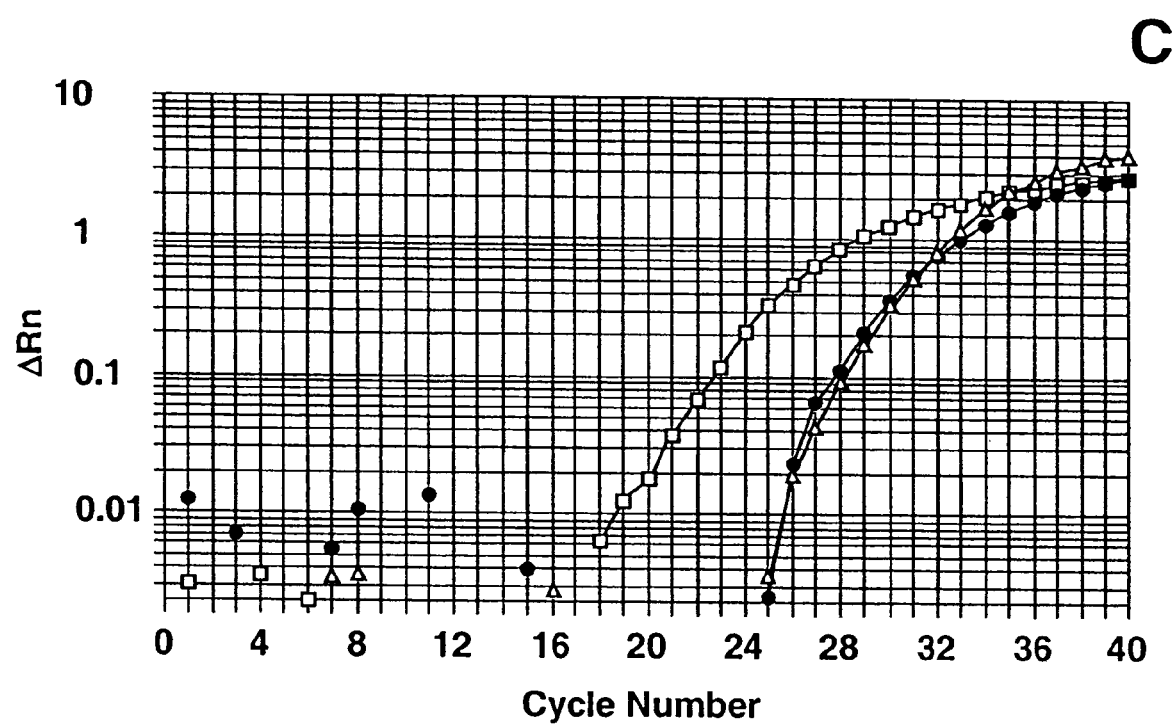
Figure 9:
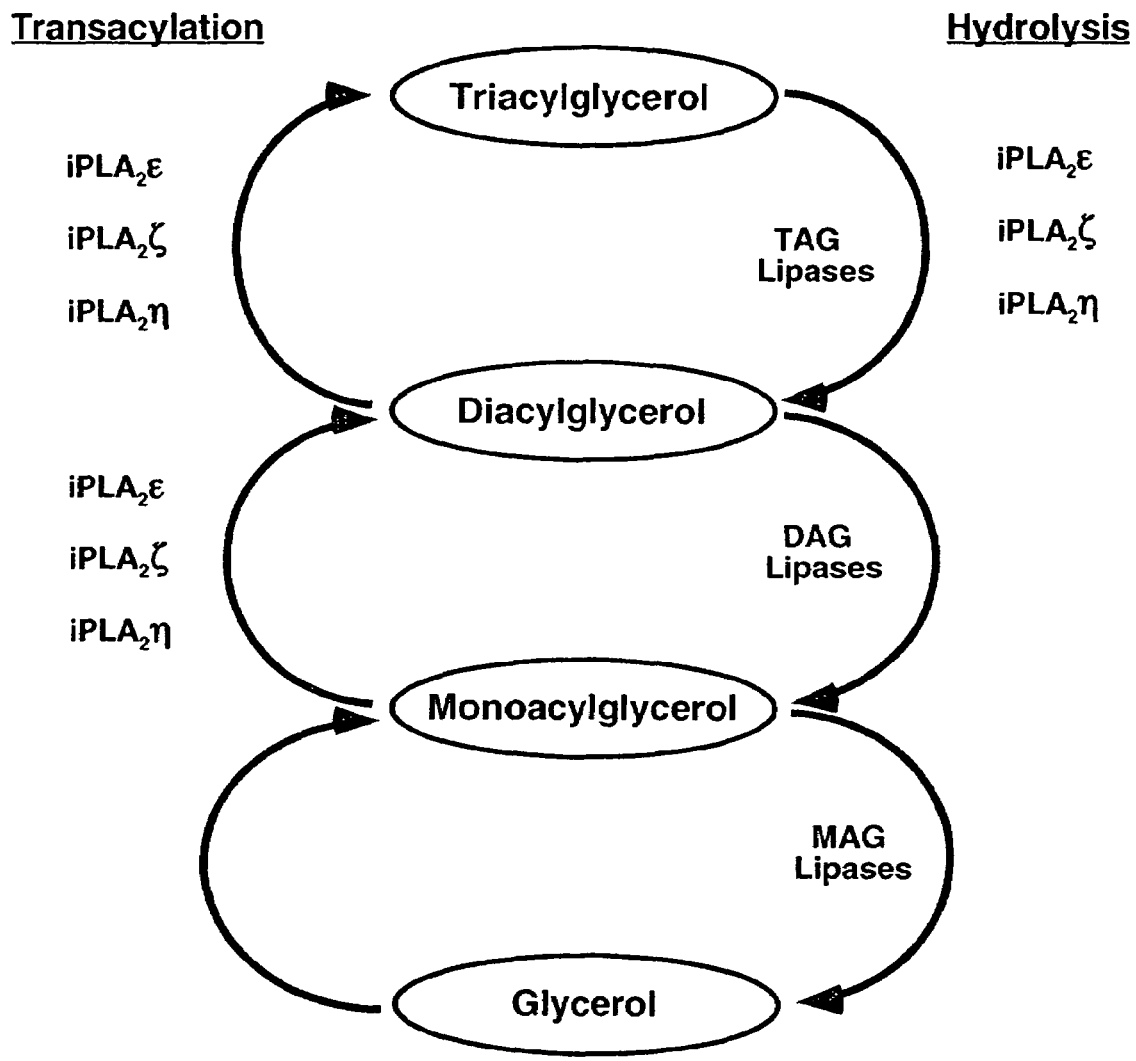
FIG. 9 shows Schematic Diagram of Adipocyte Acyl-CoA-Independent Triglyceride Cycling in a living human. The inventors have discovered that acyl-equivalents are stored in the adipocyte primarily in the form of triglycerides which can be synthesized by iPLA$_2$epsilon (adiponutrin), iPLA$_2$zeta and iPLA$_2$eta through an acyl-CoA independent transacylation mechanism which transfers fatty acyl moieties from monoacylglycerol (MAG) or diacylglycerol (DAG) acyl-donors to MAG and DAG acyl-acceptor intermediates to form triacylglycerols (TAG) and that, alternatively, hydrolysis of a single TAG fatty acyl moiety is catalyzed by iPLA$_2$epsilon, iPLA$_2$zeta, iPLA$_2$eta to form DAG which can then be further degraded to MAG and glycerol by either iPLA$_2$epsilon, iPLA$_2$zeta, iPLA$_2$eta or other intracellular lipases (e.g. hormone sensitive lipase (HSL)). Thus these enzymes contribute substantially to triglyceride homeostasis in the adipocyte.

To further examine the potential roles of iPLA$_2$epsilon, iPLA$_2$zeta, and iPLA$_2$eta in adipocyte biology, we determined the mRNA levels of each isoform in both human SW872 liposarcoma cells and differentiating 3T3-L1 adipocytes. Previous Northern analyses have demonstrated the dramatic upregulation of adiponutrin (iPLA$_2$epsilon) mRNA during 3T3-L1 adipocyte differentiation (26). Consistent with prior work, quantitative PCR utilizing primers for mouse iPLA$_2$epsilon revealed a marked increase in message by day 6 (FIG. 6A). Similarly, quantitative PCR analysis of mouse iPLA$_2$zeta in differentiating 3T3-L1 adipocytes demonstrated a 10-fold increase in message by day 6 (FIG. 6B). Since the mouse genome does not contain an obvious iPLA$_2$eta paralog, we were not able to determine the expression levels of this isoform in 3T3-L1 cells. Human SW872 liposarcoma cells have been previously utilized in the study of lipoprotein receptor-mediated cholesterol ester homeostasis (32, 40, 41). Quantitative PCR utilizing primers for iPLA$_2$epsilon, iPLA$_2$zeta, and iPLA$_2$eta demonstrated high levels of expression for all three iPLA$_2$ isofoms in this cell line (FIG. 6C).

Discussion

Progress in understanding adipocyte higlyceride homeostasis has been hindered by the difficulty in determining the diversity and chemical identities of non-HSL TAG lipases present in adipocytes (20, 22, 23). In this application, we describe the cloning, heterologous expression, and affinity purification of three novel human iPLA$_2$ family members (epsilon, zeta, and eta) and demonstrate that each possesses robust triglyceride lipase activity. Furthermore, iPLA$_2$epsilon, iPLA$_2$zeta, and iPLA$_2$eta each catalyze transacylation of a mono-olein donor to a diolein acceptor to produce TAG, thus representing a previously unrecognized acyl-CoA independent pathway for triglyceride biosynthesis in adipocytes. Importantly, iPLA$_2$epsilon (adiponutrin) expression has been previously identified as adipocyte-specific (26) and iPLA$_2$zeta (TTS-2.2) protein has been demonstrated to be enriched in CHO K2 cell liposomes (30). Herein, we demonstrate that both iPLA$_2$epsilon (adiponutrin) and iPLA$_2$zeta (TTS-2.2) transcripts are induced several-fold during 3T3-L1 preadipocyte differentiation and that mRNA encoding all three (iPLA$_2$epsilon, iPLA$_2$zeta, and iPLA$_2$eta) are present in SW872 human liposarcoma cells.

Immunohistochemical analysis of 3T3-L1 and CHO cells expressing recombinant mouse adiponutrin (iPLA$_2$epsilon) revealed that the protein was present at the periphery of the plasma membrane in punctuate granular structures and not surrounding the lipid droplets in these cells (26). However, the chemical function of the polypeptide was unknown making determination of its biologic role difficult. Furthermore, subcellular fractionation of these cells demonstrated that adiponutrin was localized predominantly to the membrane fraction and was predicted to be an integral membrane protein (26). Proteomic studies identified TTS-2.2 (iPLA$_2$zeta) as a component of CHO K2 lipid droplets likely involved in lipid metabolism (30). Subcellular fractionation of human iPLA$_2$epsilon, iPLA$_2$zeta, and iPLA$_2$eta in Sf9 cells revealed that the majority of each of these iPLA$_2$ isoforms is membrane-associated which is not unexpected given the hydrophobic nature of their lipid substrates.

Mouse adiponutrin was first identified by differential hybridization as a mRNA species that was strongly induced during differentiation of 3T3-L1 cells into adipocytes (26). Furthermore, adiponutrin mRNA was demonstrated to be exclusively expressed in adipose tissue (both white and brown), was dramatically increased after feeding (relative to the fasted state where it is virtually absent), and is inappropriately upregulated in genetic models of obesity (26,28). Subsequent studies have shown that expression of adiponutrin mRNA is rapidly induced in rats fed high sucrose (28) or high protein diets (29), but not a diet high in saturated or unsaturated fatty acids (29). Although the significance of the dietinduced regulation of adiponutrin is not known with certainty at present, the acutely coordinated responses of adiponutrin mRNA to feeding and fasting make it likely that adiponutrin participates in TAG recycling in the adipocyte.

In an aspect, the invention provides for the first time an isolated novel and purified and characterized phospholipases A$_2$, referred to herein as calcium-independent lipase A$_2$zeta (iPLA$_2$zeta) having SEQ ID NO: 2 (See FIG. 1) and nucleic acid sequence SEQ ID NO: 4 (See FIG. 7), and calcium-independent lipase A$_2$eta (iPLA$_2$eta) having SEQ ID NO: 3 (See FIG. 1) and nucleic acid sequence SEQ ID NO: 5 (See FIG. 8). For the first time herein, these novel enzymes has been isolated and characterized and is involved in the catalysis, synthesis and hydrolysis of lipids in a living mammalian cell. Moreover, these enzymes, iPLA$_2$zeta, and iPLA$_2$eta, through the process of transesterification can catalyze the net anabolic synthesis of triglycerides through a variety of metabolic precursors (e.g. monoacylglycerol, diacylglycerol and acyl CoA).

In one embodiment, the invention is directed to an isolated nucleic acid molecule comprising a set of iPLA$_2$zeta polynucleotides. In an aspect of this embodiment, the iPLA$_2$zeta polynucleotides (SEQ. ID. NO: 4) encode and express an iPLA$_2$zeta polypeptide (SEQ. ID. NO. 2).

In one embodiment, the invention is directed to an isolated nucleic acid molecule comprising a set of iPLA$_2$eta polynucleotides. In an aspect of this embodiment, the iPLA$_2$eta polynucleotides (SEQ. ID. NO: 5) encode and express an iPLA$_2$eta polypeptide (SEQ. ID. NO: 3).

In one aspect, an isolated and characterized human gene (iPLA$_2$zeta) comprises a polynucleotide having a sequence shown in SEQ. ID. NO: 4 (See FIG. 7).

In one aspect, an isolated and characterized human gene (iPLA$_2$eta) comprises a polynucleotide having a sequence shown in SEQ. ID. NO: 5 (See FIG. 8).

In an aspect, an isolated and characterized human protein (iPLA$_2$zeta) comprises a polypeptide having a sequence shown in SEQ. ID. NO: 2 (See FIG. 1).

In an aspect, an isolated and characterized human protein (iPLA$_2$eta) comprises a polypeptide having a sequence shown in SEQ. ID, NO: 3 (See FIG. 1).

In an aspect, a method of treating a living mammal to reduce obesity, comprises administering an effective amount iPLA$_2$epsilon, iPLA$_2$zeta, and/or iPLA$_2$eta inhibitor thereto or an agent which changes the lipase to transacylase ratio.

In an aspect, a genetically engineered expression vector comprises a gene or part of the sequence of a human gene comprising a polynucleotide (iPLA$_2$zeta) having a sequence shown in SEQ. ID. NO: 4 (FIG. 7). In an aspect, the gene encodes a protein comprising a polypeptide having a sequence shown in SEQ. ID. NO: 2 (FIG. 1). In an aspect, the gene is operatively linked to a capable viable promoter element.

In an aspect, a genetically engineered expression vector comprises a gene or part of the sequence of a human gene comprising a polynucleotide (iPLA$_2$eta) having a sequence shown in SEQ. ID. NO: 5 (FIG. 8). In an aspect, the gene encodes a protein comprising a polypeptide having a sequence shown in SEQ. ID. NO: 3 (FIG. 1). In an aspect, the gene is operatively linked to a capable viable promoter element.

In another aspect, a method of medically treating a mammal comprises administering an anti-obesity (drug or pharmaceutical) in therapeutically effective amounts as an inhibitor to the mammal.

In another aspect, a method of medically treating a living mammal comprises administering a therapeutically effective amount of a compound (drug or pharmaceutical) which inhibits iPLA$_2$epsilon, iPLA$_2$zeta, and/or iPLA$_2$eta expression to the mammal or results in a different isoform expression or different enzymatic activity or post-translational modification.

In another aspect, a method of medically treating a living mammal comprises administering a therapeutically effective amount of a compound (drug or pharmaceutical) which enhances iPLA$_2$epsilon, iPLA$_2$zeta, and/or iPLA$_2$eta expression to the mammal or results in a different isoform expression or different enzymatic activity or post-translational modification.

In another aspect, a method of treating obesity, comprising administering an agent which changes the transacylase to lipase activity ratio in a metabolic setting. In an aspect, the metabolic setting is an animal or animal model.

In an aspect, a pharmaceutical composition is provided comprising a compound which effectively inhibits or counteracts iPLA$_2$epsilon, iPLA$_2$zeta, and/or iPLA$_2$eta expression, hydrolytic activity, phospholipase A$_2$ activity, or transesterification activity in a living mammal.

In an aspect, a pharmaceutical kit comprises a container housing a compound which inhibits iPLA$_2$epsilon, iPLA$_2$zeta, and/or iPLA$_2$eta expression, hydrolytic activity, phospholipase A$_2$ activity, or transesterification activity.

In an aspect, a pharmaceutical kit comprises a container housing a compound which enhances iPLA$_2$epsilon, iPLA$_2$zeta, and/or iPLA$_2$eta expression, hydrolytic activity, phospholipase A$_2$ activity, or transesterification activity.

In another embodiment, the present invention is directed to a method of modulating fatty acid utilization in a patient. In an aspect, the patient is a living human patient. In this aspect, the method comprises increasing or decreasing iPLA$_2$epsilon, iPLA$_2$zeta, and/or iPLA$_2$eta activity in the patient. Patients in need of such treatment include those patients suffering from one of diabetes and/or obesity. Preferably, this method comprises administering to the patient a substance (compound) in an effective amount which blocks or inhibits expression of iPLA$_2$epsilon, iPLA$_2$zeta, and/or iPLA$_2$eta mass or activity.

In another embodiment, the present invention is directed to a method of modulating fatty acid utilization in a patient. In an aspect, the patient is a living human patient. In this aspect, the method comprises increasing or decreasing iPLA$_2$epsilon, iPLA$_2$zeta, and/or iPLA$_2$eta activity in the patient. Patients in need of such treatment include those patients suffering from one of diabetes and/or obesity. Preferably, this method comprises administering to the patient a substance (compound) in an effective amount which enhances expression of iPLA$_2$epsilon, iPLA$_2$zeta, and/or iPLA$_2$eta mass or activity.

In an aspect a method of identifying an agent which changes the ratio of transacylase to lipase activity in a living mammal by administering a compound to a mammal and determining if the transacylase to lipase activity ratio was changed by lipid analysis and if the ratio was changed then determining that the drug is an anti-obesity drug.

In an aspect, the invention comprises a method for ameliorating at least one symptom of a symptomatology comprising obesity and clinical manifestation of type 2 metabolic syndrome in a living human which comprises treating a human cell expressing iPLA$_2$epsilon, iPLA$_2$zeta, and/or iPLA$_2$eta in a pharmacologically effective manner with a pharmacologically effective amount of an iPLA$_2$epsilon, iPLA$_2$zeta, and/or iPLA$_2$eta expression or enzymatic inhibitor.

A method of treating at least one of an overweight and obese disorders, the method comprises administering to a subject (in need of such treatment) a therapeutically effective amount of composition comprising an inhibitor of human iPLA$_2$epsilon, iPLA$_2$zeta, and/or iPLA$_2$eta.

In an aspect, a method of identifying an anti-obesity drug which comprises administering a drug to an animal and determining if there has been any change in iPLA$_2$epsilon, iPLA$_2$zeta, and/or iPLA$_2$eta expression, hydrolytic activity, phospholipase A$_2$ activity, transesterification activity, or metabolic futile cycling and if so determining that the drug is an anti-obesity drug.

A method of practicing medicine which comprises administering a therapeutic amount of a drug to a patient at risk for obesity or being obese, the drug being an inhibitor of human iPLA$_2$epsilon, iPLA$_2$zeta, and/or iPLA$_2$eta.

A method of providing therapy to a patient in need thereof which comprises administering a drug to a patient at risk for obesity, the drug being an inhibitor of the expressing of human iPLA$_2$epsilon, iPLA$_2$zeta, and/or iPLA$_2$eta.

A method of providing therapy to a patient in need thereof which comprises administering a drug to a patient at risk for obesity, the drug being an activator of the expressing of human iPLA$_2$epsilon, iPLA$_2$zeta, and/or iPLA$_2$eta.

A method for treating a diabetic which comprises administering a drug in an effective amount to modulate iPLA$_2$epsilon, iPLA$_2$zeta, and/or iPLA$_2$eta expression whereby the insulin requirement of the patient is decreased.

A method of treating diabetes which comprises administering a drug in an effective amount to modulate iPLA$_2$epsilon, iPLA$_2$zeta, and/or iPLA$_2$eta expression whereby the insulin requirement of the patient is decreased.

In an aspect, the present discovery encompasses genetically engineered cells capable of identifying substances which modulate iPLA$_2$zeta expression in a living cell. In an aspect, such cells comprise a promoter operably linked to iPLA$_2$zeta gene and a reporter gene. This reporter gene preferably encodes an enzyme capable of being detected by at least one of a suitable radiometric, fluorometric or luminometric assay such as, for example, a reporter sequence encoding a luciferase. In an aspect, the promoter sequence is a baculovirus promoter sequence and the cells are Sf9 cells.

In an aspect, the present discovery encompasses genetically engineered cells capable of identifying substances which modulate iPLA$_2$eta expression in a living cell. In an aspect, such cells comprise a promoter operably linked to iPLA$_2$eta gene and a reporter gene. This reporter gene preferably encodes an enzyme capable of being detected by at least one of a suitable radiometric, fluorometric or luminometric assay such as, for example, a reporter sequence encoding a luciferase. In an aspect, the promoter sequence is a baculovirus promoter sequence and the cells are Sf9 cells.

In an aspect, as an example of its utility, the invention comprises a method for prioritizing the therapeutic capability of drugs putative efficacy against obesity, comprising administering drugs to a living animal system which is actively expressing iPLA$_2$zeta, measuring any modulation of the iPLA$_2$zeta expression by a TAG or FFA's/glycerol analysis of an effect and determining if the modulation was an increase or a decrease or no change in iPLA$_2$zeta expression level. If the modulation is determined to be a decrease then determining that the drug was effective in inhibiting iPLA$_2$zeta, a value is assigned to that modulation and is thereafter compared to the modulation of other drugs. In an aspect, a prioritization can be set up by comprising the magnitudes of the various respective modulations and a hierarchy of drugs can be established. From this, it is possible to establish a priority of work on the drugs.

In an aspect, as an example of its utility, the invention comprises a method for prioritizing the therapeutic capability of drugs putative efficacy against obesity, comprising administering drugs to a living animal system which is actively expressing iPLA$_2$eta, measuring any modulation of the iPLA$_2$eta expression by a TAG or FFA's/glycerol analysis of an effect and determining if the modulation was an increase or a decrease or no change in iPLA$_2$eta expression level. If the modulation is determined to be a decrease then determining that the drug was effective in inhibiting iPLA$_2$eta, a value is assigned to that modulation and is thereafter compared to the modulation of other drugs. In an aspect, a prioritization can be set up by comprising the magnitudes of the various respective modulations and a hierarchy of drugs can be established. From this, it is possible to establish a priority of work on the drugs.

As an example of its utility, the present invention includes a method and research tool for identifying substances which modulate iPLA$_2$zeta expression. In an aspect, the screening method and research tool comprises a screening method contacting a candidate substance with cells capably expressing iPLA$_2$zeta or a fragment thereof, and measuring the expression of iPLA$_2$zeta or a fragment thereof by the cells by an analysis of an effluent for the TAG content.

As an example of its utility, the present invention includes a method and research tool for identifying substances which modulate iPLA$_2$eta expression. In an aspect, the screening method and research tool comprises a screening method contacting a candidate substance with cells capably expressing iPLA$_2$eta or a fragment thereof, and measuring the expression of iPLA$_2$eta or a fragment thereof by the cells by an analysis of an effluent for the TAG content.

Traditionally, futile cycling has been envisaged as a mechanism to facilitate the rapid response of biochemical pathways to external perturbations. Thus, TAG futile cycling may enable the rapid and immediate response to changing metabolic conditions. Triglyceride futile cycling provides a continuously mobile pool of fatty acids so that the residence time of any given fatty acid on the glycerol backbone is time-limited, thereby reflecting the recent metabolic and dietary history of that cell. Furthermore, the presence of enzymes which can potentially alter their relative anabolic (transacylation) vs. catabolic (lipase) activities provides a potential mechanism to rapidly switch cellular metabolic balance horn energy storage to mobilization. In this regard, the upregulation of adiponutrin during feeding suggests that it may serve an anabolic function facilitating the flow of fatty acids into TAG through acylglycerol transacylation (thereby effectively decreasing systemic fatty acid release) or alternatively, adiponutrin may prevent excessive TAG accumulation in the adipocyte.

In the terminal step of acyl-CoA dependent triacylglycerol synthesis, diacylglycerol is acylated by one of two acyl-CoA: diacylgiycerol acyltransferases (DGATs) to produce TAG. While mice lacking acyl-CoA:diacylglycerol acyltransferase-1 (DGAT-1) have been demonstrated to have essentially normal adipose tissue and circulating TAG levels (42, 43), DGAT-2 knockout mice have dramatically reduced tissue and serum triglyceride levels (severe lipopenia) which is lethal within 24 hours after birth (44). Clearly, these results illustrate the importance of DGAT-2 catalyzed TAG synthesis in post-natal survival. To our knowledge, acyl-CoA independent TAG synthesis in adipocytes has not been previously documented, which may be due in part to the presence of high monoacylglycerol and diacylglycerol lipase (HSL) activities present in in vitro assay systems. Rat intestinal enterocytes contain a 50-52 kDa acyl-CoA independent sn-1,2(2,3)-diacylglycerol transacylase of unknown primary sequence which utilizes diolein or mono-olein acyl donors for transacylation of diolein or mono-olein acyl acceptors to form triolein (24). Since no amino acid sequence data was published on the identity of this partially purified protein, it is unknown whether this protein was adiponutrin, TTS-2.2, or another protein entirely. Although heparin-releasable hepatic lipase has been shown to catalyze acyl transfer from the 1(3)-position of neutral glycerides to various lipid acceptors, to our knowledge, iPLA$_2$epsilon, iPLA$_2$zeta, and iPLA$_2$eta represent the first intracellular mammalian acylglycerol transacylases to be identified at the molecular level.

GS2 (termed "gene sequence 2") was originally cloned in 1994 as the second gene present within a CpG island-rich contig of the distal short arm of human X chromosome (45). Located midway between the steroid sulfatase (STS) and Kallman syndrome (KALI) loci, the GS2 gene is comprised of 7 exons which are distributed over 26 kb (45). GS2 mRNA transcripts of varying size are highly expressed in liver, brain, and skeletal muscle with lower amounts present in lung, placenta, kidney, and pancreas (45). Expression levels of GS2 mRNA in adipose tissue have not been examined to our knowledge. Deletion of GS2 appears to be non-lethal, although the precise phenotype is not clear since patients with X-linked ichthyosis who have the deleted GS2 (iPLA$_2$eta) in addition to the steroid sulfatase gene (STS) are indistinguishable from those with mutations within the STS gene alone at the current level of discrimination (46).

The metabolic pathways which contribute to the elevated levels of circulating non-esterified fatty acids in obese individuals are unclear. Clinically, high serum free fatty acid levels are treated by administration of thiazolidinediones (TZDs) which mediate their effects through PPARgarnma. One mechanism through which TZDs are believed to decrease serum non-esterified fatty acids is through the induction of glycerol kinase (9) and phosphoenolpyruvate carboxykinase (47) which provide glycerol-3-phosphate for re-esterification of fatty acyl equivalents (TAG synthesis) in the adipocyte. Clearly, the potential significance of the relative triglyceride lipase activities of iPLA$_2$epsilon, iPLA$_2$zeta, and iPLA$_2$eta in comparison to their transacylase activities in contributing to serum free fatty acid levels in individuals with metabolic syndrome X and type 2 diabetes is of great interest. Although in vitro activity measurements demonstrate that the TAG lipase activities of each iPLA$_2$ isoform are greater than their respective transacylase activities, past-translational modifications (e.g. phosphorylation), protein-protein interactions, and/or specific lipid droplet microenvironments may alter the transacylasellipase activity ratios of iPLA$_2$epsilon, iPLA$_2$zeta, and iPLA$_2$eta in vivo. Intriguingly, treatment of differentiating 3T3-L1 adipocytes with troglitazone down-regulates adiponutrin (iPLA$_2$epsilon) mRNA levels (27). Thus, the up-regulation of adiponutrin, which has been observed to occur in obese rats (26), may contribute to either the high basal levels of circulating non-esterified fatty acids (due to TAG lipase activity) or to adipocyte hypertrophy (due to acylglycerol transacylation) observed in obese individuals.

We have identified three novel human triacylglycerol lipases/transacylases which are related to the iPLA$_2$ family of enzymes by virtue of their dual signature nucleotide binding and lipase consensus motifs. Moreover, iPLA$_2$zeta (TTS-2.2), like iPLA$_2$epsilon (adiponutrin) (26), is upregulated during 3T3-L1 adipocyte differentiation and all three of the novel iPLA$_2$ isoforms are present in a human liposarcoma cell line. Collectively, these results provide a new foundation to increase understanding of triglyceride homeostasis in adipocytes. Of particular interest will be studies identifying the effects of altering iPLA$_2$epsilon, iPLA$_2$zeta, and iPLA$_2$eta expression levels and determination of the diversity of biologically relevant isofomms and their specific effects on cellular lipid homeostasis. Multiple mechanisms controlling iPLA$_2$epsilon, iPLA$_2$zeta, and iPLA$_2$eta protein mass (via transcription and/or translation) and lipase/transacylase activity (via post-translational modification and/or protein-protein interactions) likely contribute to the regulation of the anabolic and catabolic fluxes of acyl equivalents in adipocytes.

In another aspect of this invention, a method of medically treating a living mammal comprises administering to a living mammal or to a cell thereof a therapeutically effective amount of a compound (drug or pharmaceutical) which inhibits iPLA$_2$epsilon, iPLA$_2$zeta, and/or iPLA$_2$eta expression to the mammal or result in a different isoform expression or different enzymatic activity or posttranslational modification.

Compounds shown to inhibit iPLA$_2$epsilon, iPLA$_2$zeta, and/or iPLA$_2$eta can be utilized as diagnostics, therapeutics, and as research reagents and provided in kits. They can be utilized in pharmaceutical compositions by adding an effective amount of an oligonucleotide of the invention to a suitable pharmaceutically acceptable diluent or carrier. They further can be used for treating organisms having a disease characterized by the undesired production of a protein. The organism can be contacted with an oligonucleotide of the invention having a sequence that is capable of specifically hybridizing with a strand of target nucleic acid that codes for the undesirable protein.

The formulation of therapeutic compositions and their subsequent administration is believed to be within the skill of those in the art. In general, for therapeutics, a patient in need of such therapy is administered an oligomer in accordance with the invention, commonly in a pharmaceutically acceptable carrier, depending on the age of the patient and the severity of the disease state being treated. Further, the treatment may be a single dose or may be a regimen that may last for a period of time which will vary depending upon the nature of the particular disease, its severity and the overall condition of the patient, and may extend from once daily to once every 20 years. Following treatment, the patient is monitored for changes in his/her condition and for alleviation of the symptoms of the disease state. The dosage of the oligomer may either be increased in the event the patient does not respond significantly to current dosage levels, or the dose may be decreased if an alleviation of the symptoms of the disease state is observed, or if the disease state has been ablated.

Following successful treatment, it may be desirable to have the patient undergo maintenance therapy to prevent the recurrence of the disease state, wherein the oligomer is administered in maintenance doses, ranging from 0.01 microgram to 100 g per kg of body weight, once or more daily, to once every several years.

The pharmaceutical compositions of the present invention may be effectively administered in a number of ways to mammals depending upon whether local or systemic treatment is desired and upon the area to be treated. Administration may be topical (including ophthalmic, vaginal, rectal, intranasal, transdermal), oral or parenteral. Parenteral administration includes intravenous drip, subcutaneous, intraperitoneal or intramuscular injection, or intrathecal or intraventricular administration.

Formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable. Coated condoms, gloves and the like may also be useful.

Compositions for oral administration include powders or granules, suspensions or solutions in water or non-aqueous media, capsules, sachets or tablets. Thickeners, flavoring agents, diluents, emulsifiers, dispersing aids or binders may be desirable.

Compositions for intrathecal or intraventricular administration may include sterile aqueous solutions which may also contain buffers, diluents and other suitable additives.

Formulations for parenteral administration may include sterile aqeous solutions which may also contain buffers, diluents and other suitable additives.

Key Words: Adiponutrin, TTS-2.2, GS2, Lipase, Transacylase, Phospholipase A$_2$, Triacylglycerol.

Abbreviations
BEL—(E)-6-(bromomethyl ene)-3-(1-naphthalenyl)-2H-tetrahydropyran-$_2$-one.
iPLA$_2$—Calcium-independent phospholipase A$_2$.
DAG—Diacylglycerol.
DOG—Diolein.
DGAT—Acyl:CoA:diacylglycerol acyltransferase.
GS2—Gene sequence 2.
MAG—Monoacylglycerol.
MOG—Mono-olein.
TAG—Triacylglycerol.
TOG—Triolein.
TTS-2.2—Transport secretion protein-2.2.

KEY OF SYMBOLS

α=alpha
β=beta
γ=gamma
Δ=delta
ε=epsilon
ζ=zeta
η=eta
μ=micro

REFERENCES

1. Kopelman, P. G. (2000) Nature 404,635-643.
2. Mokdad, A. H., Bowman, B. A., Ford, E. S., Vinicor, F., Marks, J. S., and Koplan, J. P. (2001) Jama 286, 1195-1200.
3. James, P. T., Leach, R., Kalamara, E., and Shayeghi, M. (2001) Obes Res 9 Suppl 4,228S-233S.
4. Pi-Sunyer, F. X. (2002) Obes Res 10 Suppl 2,97S-104S.
5. Boden, G., and Shulman, G. I. (2002) Eur J Clin Invest 32 Suppl 3, 14-23.
6. McGarry, J. D., and Dobbins, R. L. (1999) Diabetologia 42, 128-138
7. Unger, R, H., and Orci, L. (2001) Faseb J15, 312-321.
8. Schaffer, J. E. (2003) Curr Opin Lipidol 14, 281-287.
9. Guan, H. P., Li, Y., Jensen, M. V., Newgard, C. B., Steppan, C. M., and Lazar, M. A. (2002) Nat Med 8, 1122-1128
10. Reshef, L., Olswang, Y., Cassuto, H., Blum, B., Croniger, C. M., Kalhan, S. C., Tilghrnan, S. M., and Hanson, R. W. (2003) J Biol Chem 278, 30413-30416.
11. Lehner, R., and Kuksis, A. (1996) Prog Lipid Res 35, 169-201.
12. Coleman, R. A., and Lee, D. P. (2004) Prog Lipid Res 43, 134-176.
13. Holm, C., Kirchgessner, T. G., Svenson, K. L., Fredrikson, G., Nilsson, S., Miller, C. G., Shively, J. E., Heinunann, C., Sparkes, R. S., Mohandas, T., and et al. (1988) Science 241, 1503-1506.
14. Yeaman, S. J. (2004) Biochem J379, 11-22.
15. Kraemer, F. B., and Shen, W. J. (2002) J Lipid Res 43, 1585-1594.
16. Fredrikson, G., Stralfors, P., Nilsson, N. O., and Belfrage, P. (1 98 1) J Biol Chem 256,6311-6320.
17. Shen, W. J., Patel, S., Natu, V., and Kraemer, F. B. (1998) Biochemisdtry 37,8973-8979.
18. Anthonsen, M, W., Ronnstrand, L., Wemstedt, C., Degeman, E., and Holm, C. (1998) J Biol Chem 273, 215-221.
19. Greenberg, A. S., Shen, W. J., Muliro, K, Patel, S., Souza, S. C., Roth, R. A., and Kraemer, F. B. (2001) J Biol Chem 276,45456-45461.
20. Haernmerle, G., Zirnmemann, R., Hayn, M., Theussl, C., Waeg, G., Wagner, E., Sattler, W., Magin, T. M., Wagner, E. F., and Zechner, R. (2002) J Biol Chem 277,4806-4815.
21. Osuga, J., Ishibashi, S., Oka, T., Yagyu, H., Tozawa, R., Fujimoto, A., Shionoiri, F., Yahagi, N., Kraemer, F. B, Tsutsumi, O., and Yamada, N. (2000) Proc Natl Acad Sci USA 97, 787-792.
22. Wang, S. P., Laurin, N., Himms-Hagen, J., Rudnidci, M. A., Levy, E., Robert, M. F., Pan, L., Oligny, L., and Mitchell, G. A. (2001) Obes Res 9, 119-128.
23. Okazaki, H., Osuga, J., Tamura, Y., Yahagi, N., Tomita, S., Shionoiri, F., Iizuka, Y., Ohashi, K., Harada, K., Kimura, S., Gotoda, T., Shimano, H., Yarnada, N., and Ishibashi, S. (2002) Diabetes 51, 3368-3375.
24. Lehner, R., and Kuksis, A. (1993) J Biol Chem 268, 8781-8786.
25. Buhman, K. K., Smith, S. J., Stone, S. J., Repa, J. J., Wong, J. S., Knapp, F. F., Jr., Burri, B. J., Hamilton, R. L., Abumrad, N. A., and Farese, R. V., Jr. (2002) J Biol Chem 277, 25474-25479.
26. Baulande, S., Lasnier, F., Lucas, M., and Pairault, J. (2001) J Biol Chem 276, 33336-33344.
27. Poison, D., and Thompson, M, (2003) Horm Metab Res 35, 508-510.
28. Polson, D. A., and Thompson, M. P. (2003) Biochem Biophys Res Commun 301, 261-266.
29. Poison, D. A., and Thompson, M. P. (2004) J Nutr Biochem 15, 242-246.
30. Liu, P., Ying, Y., Zhao, Y., Mundy, D. I., Zhu, M, and Anderson, R. G. (2004) J Biol Chem 279, 3787-3792.
31. Frost, S. C., and Lane, M. D. (1985) J Biol Chem 260, 2646-2652.
32. Izem, L., and Morton, R. E. (2001) J Biol Chem 276, 26534-26541.
33. Laemmli, U. K. (1970) Nature 227, 680-685.
34. Gailiard, T. (1971) Biochem J 121,3 79-390.
35. Andrews, D. L., Beames, B., Summers, M. D., and Park, W. D. (1988) Biochem J252, 199-206.
36. Pinsirodom, P., and Parkin, K. L. (2000) J Agric Food Chem 48, 155-160.
37. Hazen, S. L., Zupan, L. A., Weiss, R. H., Getman, D. P., and Gross, R. W. (1991) J Biol Chem 266, 7227-7232.
38. Zupan, L. A., Weiss, R. H., Hazen, S. L., Parnas, B. L., Aston, K. W., Lemon, P. J., Getman, D. P., and Gross, R. W. (1993) J Med Chem 36, 95-100.
39. Mancuso, D. J., Jenkins, C. M., and Gross, R. W. (2000) J Biol Chem 275, 9937-9945.
40. Gauthier, A., Vassiliou, G., Benoist, F., and McPherson, R. (2003) J Biol Chem 278, 11945-11953.
41. Vassiliou, G., Benoist, F., Lau, P., Kavaslar, G. N., and McPherson, R. (2001) J Biol Chem 276, 48823-48830.
42. Smith, S. J., Cases, S., Jensen, D. R., Chen, H. C., Sande, E., Tow, B., Sanan, D. A., Raber, J., Eckel, R. H., and Farese, R. V., Jr. (2000) Nat Genet 25, 87-90
43. Chen, H. C., Smith, S. J., Ladha, Z, Jensen, D. R, Ferreira, L. D., Pulawa, L, K, McGuire, J. G., Pitas, R. E., Eckel, R. H., and Farese, R. V., Jr. (2002) J Clin Invest 109, 1049-1055.
44. Stone, S. J., Myers, H. M., Watkins, S. Ma, Brown, B. E., Feingold, K. R., Elias, P. M., and Farese, R. V., Jr. (2004) J Biol Chem 279, 11767-11776.
45. Lee, W. C., Salido, E., and Yen, P. H. (1994) Genomics 22, 372-376.
46. Shapiro, L. J., Yen, P., Pomerantz, D., Martin, E., Rolewic, L., and Mohandas, T. (1989) Proc Natl Acad Sci USA 86, 8477-8481.

47. Tordjman, J., Chauvet, G., Quette, J., Beale, E. G., Forest, C., and Antoine, B. (2003) *J Bid Chem* 278, 18785-18790.

48. Corpet, F. (1988) Nucleic Acids Res 16, 10881-10890.

Elia, M., Zed, C., Neale, G., and Livesey, G. (1987) *Metabolism* 36, 251-255

Van Harmelen, V., Reynisdottir, S., Cianflone, K., Degerman, E., Hoffstedt, J., Nilsell, K., Sniderman, A., and Arner, P. (1999) *J Biol Chem* 274, 18243-18251

Jensen, M. D., Ekberg, K., and Landau, B. R. (2001) *Am J Physiol Endocrinol Metab* 281, E789-793

Gibbons, G. F., Islam, K., and Pease, R. J. (2000) *Biochim Biophys Acta* 1483, 37-57

Raclot, T. (2003) *Prog Lipid Res* 42, 257-288

Tang, J., Kriz, R. W., Wolfman, N., Shaffer, M., Seehra, J., and Jones, S. S. (1997) *J Biol Chem* 272, 8567-8575 van Tienhoven, M., Atkins, J., Li, Y., and Glynn, P. (2002) *J Biol Chem* 277, 20942-20948

Waite, M., and Sisson, P. (1973) *J Biol Chem* 248, 7985-7992

Hulsmann, W. C., Oerlemans, M. C., and Jansen, H. (1980) *Biochim Biophys Acta* 618, 364-369

Glorian, M., Duplus, E., Beale, E. G., Scott, D. K., Granner, D. K., and Forest, C. (2001) *Biochimie* 83, 933-943

While the discovery has been described in terms of various specific embodiments, those skilled in the art will recognize that the discovery can be practiced with modification within the spirit and scope of the discovery.

---

What is claimed is:

1. A method of identifying an anti-obesity or anti-diabetic drug, the method comprising
   administering a drug to an animal;
   determining if there has been any change in expression of iPLA$_2$epsilon, iPLA$_2$zeta, iPLA$_2$eta, or combinations thereof by analysis of lipids; and
   determining if the drug is an anti-obesity drug or an anti-diabetic drug.

2. A method in accordance with claim 1 wherein the animal is a living human.

3. A method in accordance with claim 1 wherein the iPLA$_2$epsilon, iPLA$_2$zeta, or iPLA$_2$eta is membrane-associated.

4. A method in accordance with claim 1 wherein the iPLA$_2$epsilon, iPLA$_2$zeta, or iPLA$_2$eta is expressed in adipocytes or human liposarcoma cells.

5. A method in accordance with claim 1 wherein the change in the expression of iPLA$_2$epsilon, iPLA$_2$zeta, or iPLA$_2$eta is determined by measuring a change in a lipase to transacylase activity ratio.

6. A method in accordance with claim 1 wherein the change in the expression of iPLA$_2$epsilon, iPLA$_2$zeta, or iPLA$_2$eta is determined by measuring a change in the levels of mRNA encoding iPLA$_2$epsilon, iPLA$_2$zeta, or iPLA$_2$eta in adipocytes or human liposarcoma cells.

7. A method in accordance with claim 1 wherein the change in the expression of iPLA$_2$epsilon, iPLA$_2$zeta, or iPLA$_2$eta is determined by measuring a change in the degree of diolein synthesis from a mono-olein acyl donor in the presence of a mono-olein acceptor.

8. A method in accordance with claim 1 wherein the change in the expression of iPLA$_2$epsilon, iPLA$_2$zeta, or iPLA$_2$eta is determined by measuring a change in the degree of triolein synthesis from a mono-olein acyl donor in the presence of a diolein acceptor.

9. A method in accordance with claim 1 wherein the change in the expression of iPLA$_2$epsilon, iPLA$_2$zeta, or iPLA$_2$eta is determined by measuring a change in triolein lipase activity.

10. A method in accordance with claim 1 wherein the method further comprises determining if the change is an increase or a decrease in the expression of iPLA$_2$epsilon, iPLA$_2$zeta, or iPLA$_2$eta.

11. A method in accordance with claim 10 wherein the change in the expression of iPLA$_2$epsilon, iPLA$_2$zeta, or iPLA$_2$eta is a decrease.

* * * * *

SEQUENCE LISTING

<160> NUMBER OF SEQ ID NOS: 30

<210> SEQ ID NO 1
<211> LENGTH: 487
<212> TYPE: PRT
<213> ORGANISM: Homo sapiens

<400> SEQUENCE: 1

```
Met Tyr Asp Ala Glu Arg Gly Trp Ser Leu Ser Phe Ala Gly Cys Gly
 1               5                  10                  15

Phe Leu Gly Phe Tyr His Val Gly Ala Thr Arg Cys Leu Ser Glu His
            20                  25                  30

Ala Pro His Leu Leu Arg Asp Ala Arg Met Leu Phe Gly Ala Ser Ala
        35                  40                  45

Gly Ala Leu His Cys Val Gly Val Leu Ser Gly Ile Pro Leu Glu Gln
    50                  55                  60

Thr Leu Gln Val Leu Ser Asp Leu Val Arg Lys Ala Arg Ser Arg Asn
65                  70                  75                  80

Ile Gly Ile Phe His Pro Ser Phe Asn Leu Ser Lys Phe Leu Arg Gln
                85                  90                  95

Gly Leu Cys Lys Cys Leu Pro Ala Asn Val His Gln Leu Ile Ser Gly
            100                 105                 110

Lys Ile Gly Ile Ser Leu Thr Arg Val Ser Asp Gly Glu Asn Val Leu
        115                 120                 125

Val Ser Asp Phe Arg Ser Lys Asp Glu Val Val Asp Ala Leu Val Cys
    130                 135                 140

Ser Cys Phe Ile Pro Phe Tyr Ser Gly Leu Ile Pro Pro Ser Phe Arg
145                 150                 155                 160

Gly Val Arg Tyr Val Asp Gly Gly Val Ser Asp Asn Val Pro Phe Ile
                165                 170                 175

Asp Ala Lys Thr Thr Ile Thr Val Ser Pro Phe Tyr Gly Glu Tyr Asp
            180                 185                 190

Ile Cys Pro Lys Val Lys Ser Thr Asn Phe Leu His Val Asp Ile Thr
        195                 200                 205

Lys Leu Ser Leu Arg Leu Cys Thr Gly Asn Leu Tyr Leu Leu Ser Arg
    210                 215                 220

Ala Phe Val Pro Pro Asp Leu Lys Val Leu Gly Glu Ile Cys Leu Arg
225                 230                 235                 240

Gly Tyr Leu Asp Ala Phe Arg Phe Leu Glu Glu Lys Gly Ile Cys Asn
                245                 250                 255
```

```
Arg Pro Gln Pro Gly Leu Lys Ser Ser Glu Gly Met Asp Pro Glu
            260                 265                 270

Val Ala Met Pro Ser Trp Ala Asn Met Ser Leu Asp Ser Pro Glu
            275                 280                 285

Ser Ala Ala Leu Ala Val Arg Leu Glu Gly Asp Glu Leu Leu Asp His
            290                 295                 300

Leu Arg Leu Ser Ile Leu Pro Trp Asp Glu Ser Ile Leu Asp Thr Leu
305                 310                 315                 320

Ser Pro Arg Leu Ala Thr Ala Leu Ser Glu Glu Met Lys Asp Lys Gly
            325                 330                 335

Gly Tyr Met Ser Lys Ile Cys Asn Leu Leu Pro Ile Arg Ile Met Ser
            340                 345                 350

Tyr Val Met Leu Pro Cys Thr Leu Pro Val Glu Ser Ala Ile Ala Ile
            355                 360                 365

Val Gln Arg Leu Val Thr Trp Leu Pro Asp Met Pro Asp Asp Val Leu
            370                 375                 380

Trp Leu Gln Trp Val Thr Ser Gln Val Phe Thr Arg Val Leu Met Cys
385                 390                 395                 400

Leu Leu Pro Ala Ser Arg Ser Gln Met Pro Val Ser Ser Gln Gln Ala
            405                 410                 415

Ser Pro Cys Thr Pro Glu Gln Asp Trp Pro Cys Trp Thr Pro Cys Ser
            420                 425                 430

Pro Glu Gly Cys Pro Ala Glu Thr Lys Ala Glu Ala Thr Pro Arg Ser
            435                 440                 445

Ile Leu Arg Ser Ser Leu Asn Phe Phe Leu Gly Asn Lys Val Pro Ala
450                 455                 460

Gly Ala Glu Gly Leu Ser Thr Phe Pro Ser Phe Ser Leu Glu Lys Ser
465                 470                 475                 480

Leu His His His His His His
            485

<210> SEQ ID NO 2
<211> LENGTH: 510
<212> TYPE: PRT
<213> ORGANISM: Homo sapiens

<400> SEQUENCE: 2

Met Phe Pro Arg Glu Lys Thr Trp Asn Ile Ser Phe Ala Gly Cys Gly
1               5                   10                  15

Phe Leu Gly Val Tyr Tyr Val Gly Val Ala Ser Cys Leu Arg Glu His
            20                  25                  30

Ala Pro Phe Leu Val Ala Asn Ala Thr His Ile Tyr Gly Ala Ser Ala
        35                  40                  45

Gly Ala Leu Thr Ala Thr Ala Leu Val Thr Gly Val Cys Leu Gly Glu
    50                  55                  60

Ala Gly Ala Lys Phe Ile Glu Val Ser Lys Glu Ala Arg Lys Arg Phe
65                  70                  75                  80

Leu Gly Pro Leu His Pro Ser Phe Asn Leu Val Lys Ile Ile Arg Ser
            85                  90                  95

Phe Leu Leu Lys Val Leu Pro Ala Asp Ser His Glu His Ala Ser Gly
            100                 105                 110

Arg Leu Gly Ile Ser Leu Thr Arg Val Ser Asp Gly Glu Asn Val Ile
        115                 120                 125

Ile Ser His Phe Asn Ser Lys Asp Glu Leu Ile Gln Ala Asn Val Cys
130                 135                 140
```

```
Ser Gly Phe Ile Pro Val Tyr Cys Gly Leu Ile Pro Ser Leu Gln
145                 150                 155                 160

Gly Val Arg Tyr Val Asp Gly Ile Ser Asp Asn Leu Pro Leu Tyr
            165                 170                 175

Glu Leu Lys Asn Thr Ile Thr Val Ser Pro Phe Ser Gly Glu Ser Asp
                180                 185                 190

Ile Cys Pro Gln Asp Ser Ser Thr Asn Ile His Glu Leu Arg Val Thr
                195                 200                 205

Asn Thr Ser Ile Gln Phe Asn Leu Arg Asn Leu Tyr Arg Leu Ser Lys
210                 215                 220

Ala Leu Phe Pro Pro Glu Pro Leu Val Leu Arg Glu Met Cys Lys Gln
225                 230                 235                 240

Gly Tyr Arg Asp Gly Leu Arg Phe Leu Gln Arg Asn Gly Leu Leu Asn
            245                 250                 255

Arg Pro Asn Pro Leu Leu Ala Leu Pro Pro Ala Arg Pro His Gly Pro
            260                 265                 270

Glu Asp Lys Asp Gln Ala Val Glu Ser Ala Gln Ala Glu Asp Tyr Ser
            275                 280                 285

Gln Leu Pro Gly Glu Asp His Ile Leu Glu His Leu Pro Ala Arg Leu
290                 295                 300

Asn Glu Ala Leu Leu Glu Ala Cys Val Glu Pro Thr Asp Leu Leu Thr
305                 310                 315                 320

Thr Leu Ser Asn Met Leu Pro Val Arg Leu Ala Thr Ala Met Met Val
                325                 330                 335

Pro Tyr Thr Leu Pro Leu Glu Ser Ala Leu Ser Phe Thr Ile Arg Leu
            340                 345                 350

Leu Glu Trp Leu Pro Asp Val Pro Glu Asp Ile Arg Trp Met Lys Glu
            355                 360                 365

Gln Thr Gly Ser Ile Cys Gln Tyr Leu Val Met Arg Ala Lys Arg Lys
            370                 375                 380

Leu Gly Arg His Leu Pro Ser Arg Leu Pro Glu Gln Val Glu Leu Arg
385                 390                 395                 400

Arg Val Gln Ser Leu Pro Ser Val Pro Leu Ser Cys Ala Ala Tyr Arg
                405                 410                 415

Glu Ala Leu Pro Gly Trp Met Arg Asn Asn Leu Ser Leu Gly Asp Ala
            420                 425                 430

Leu Ala Lys Trp Glu Glu Cys Gln Arg Gln Leu Leu Leu Gly Leu Phe
            435                 440                 445

Cys Thr Asn Val Ala Phe Pro Pro Glu Ala Leu Arg Met Arg Ala Pro
450                 455                 460

Ala Asp Pro Ala Pro Ala Asp Pro Ala Ser Pro Gln His Gln
465                 470                 475                 480

Pro Ala Gly Pro Ala Pro Leu Leu Ser Thr Pro Ala Pro Glu Ala Arg
            485                 490                 495

Pro Val Ile Gly Ala Leu Gly Leu His His His His His
            500                 505                 510

<210> SEQ ID NO 3
<211> LENGTH: 267
<212> TYPE: PRT
<213> ORGANISM: Homo sapiens

<400> SEQUENCE: 3

Met Lys His Ile Asn Leu Ser Phe Ala Ala Cys Gly Phe Leu Gly Ile
```

```
                1               5              10              15
              Tyr His Leu Gly Ala Ala Ser Ala Leu Cys Arg His Gly Lys Lys Leu
                              20                  25                  30

Val Lys Asp Val Lys Ala Phe Ala Gly Ala Ser Ala Gly Phe Thr Ser
                          35                  40                  45

Leu Val Ala Ser Val Leu Leu Thr Ala Pro Glu Lys Ile Glu Glu Cys
                      50                  55                  60

Asn Gln Phe Thr Tyr Lys Phe Ala Glu Glu Ile Arg Arg Gln Ser Phe
               65                  70                  75                  80

Gly Ala Val Thr Pro Gly Tyr Asp Phe Met Ala Arg Leu Arg Ser Gly
                                  85                  90                  95

Met Glu Ser Ile Leu Pro Pro Ser Ala His Phe Thr Glu Leu Ala Gln
                             100                 105                 110

Asn Arg Leu His Val Ser Ile Thr Asn Ala Lys Thr Arg Glu Asn His
                         115                 120                 125

Leu Val Ser Thr Phe Ser Ser Arg Glu Asp Leu Ile Lys Val Leu Leu
                     130                 135                 140

Ala Ser Ser Phe Val Pro Ile Tyr Ala Gly Leu Lys Leu Val Glu Tyr
              145                 150                 155                 160

Lys Gly Gln Lys Trp Val Asp Phe Thr Gly Leu Thr Asn Ala Leu
                                 165                 170                 175

Pro Ile Leu Pro Val Gly Arg Thr Val Thr Ile Ser Pro Phe Ser Gly
                             180                 185                 190

Arg Leu Asp Ile Ser Pro Gln Asp Lys Gly Gln Leu Asp Leu Tyr Val
                         195                 200                 205

Asn Ile Ala Lys Gln Asp Ile Met Leu Ser Leu Ala Asn Leu Val Arg
                     210                 215                 220

Leu Asn Gln Ala Phe Thr Leu Phe Pro Pro Ser Lys Arg Lys Met Glu
              225                 230                 235                 240

Ser Leu Tyr Gln Cys Gly Phe Asp Asp Thr Val Lys Phe Leu Leu Lys
                                 245                 250                 255

Glu Asn Trp Phe Glu His His His His His His
                             260                 265

<210> SEQ ID NO 4
<211> LENGTH: 1515
<212> TYPE: DNA
<213> ORGANISM: Homo sapiens
<220> FEATURE:
<221> NAME/KEY: CDS
<222> LOCATION: (1)..(1512)

<400> SEQUENCE: 4 atg ttt ccc cgc gag aag acg tgg aac atc tcg ttc gcg ggc tgc ggc        48
Met Phe Pro Arg Glu Lys Thr Trp Asn Ile Ser Phe Ala Gly Cys Gly
 1               5                  10                  15 ttc ctc ggc gtc tac tac gtc ggc gtg gcc tcc tgc ctc cgc gag cac        96
Phe Leu Gly Val Tyr Tyr Val Gly Val Ala Ser Cys Leu Arg Glu His
                 20                  25                  30 gcg ccc ttc ctg gtg gcc aac gcc acg cac atc tac ggc gcc tcg gcc       144
Ala Pro Phe Leu Val Ala Asn Ala Thr His Ile Tyr Gly Ala Ser Ala
             35                  40                  45 ggg gcg ctc acg gcc acg gcg ctg gtc acc ggg gtc tgc ctg ggt gag       192
Gly Ala Leu Thr Ala Thr Ala Leu Val Thr Gly Val Cys Leu Gly Glu
         50                  55                  60 gct ggt gcc aag ttc att gag gta tct aaa gag gcc cgg aag cgg ttc       240
Ala Gly Ala Lys Phe Ile Glu Val Ser Lys Glu Ala Arg Lys Arg Phe
```

-continued

```
                65                  70                  75                  80
ctg ggc ccc ctg cac ccc tcc ttc aac ctg gta aag atc atc cgc agt         288
Leu Gly Pro Leu His Pro Ser Phe Asn Leu Val Lys Ile Ile Arg Ser
                    85                  90                  95 ttc ctg ctg aag gtc ctg cct gct gat agc cat gag cat gcc agt ggg         336
Phe Leu Leu Lys Val Leu Pro Ala Asp Ser His Glu His Ala Ser Gly
            100                 105                 110 cgc ctg ggc atc tcc ctg acc cgc gtg tca gac ggc gag aat gtc att         384
Arg Leu Gly Ile Ser Leu Thr Arg Val Ser Asp Gly Glu Asn Val Ile
        115                 120                 125 ata tcc cac ttc aac tcc aag gac gag ctc atc cag gcc aat gtc tgc         432
Ile Ser His Phe Asn Ser Lys Asp Glu Leu Ile Gln Ala Asn Val Cys
    130                 135                 140 agc ggt ttc atc ccc gtg tac tgt ggg ctc atc cct ccc tcc ctc cag         480
Ser Gly Phe Ile Pro Val Tyr Cys Gly Leu Ile Pro Pro Ser Leu Gln
145                 150                 155                 160 ggg gtg cgc tac gtg gat ggt ggc att tca gac aac ctg cca ctc tat         528
Gly Val Arg Tyr Val Asp Gly Gly Ile Ser Asp Asn Leu Pro Leu Tyr
                    165                 170                 175 gag ctt aag aac acc atc aca gtg tcc ccc ttc tcg ggc gag agt gac         576
Glu Leu Lys Asn Thr Ile Thr Val Ser Pro Phe Ser Gly Glu Ser Asp
            180                 185                 190 atc tgt ccg cag gac agc tcc acc aac atc cac gag ctg cgg gtc acc         624
Ile Cys Pro Gln Asp Ser Ser Thr Asn Ile His Glu Leu Arg Val Thr
        195                 200                 205 aac acc agc atc cag ttc aac ctg cgc aac ctc tac cgc ctc tcc aag         672
Asn Thr Ser Ile Gln Phe Asn Leu Arg Asn Leu Tyr Arg Leu Ser Lys
    210                 215                 220 gcc ctc ttc ccg ccg gag ccc ctg gtg ctg cga gag atg tgc aag cag         720
Ala Leu Phe Pro Pro Glu Pro Leu Val Leu Arg Glu Met Cys Lys Gln
225                 230                 235                 240 gga tac cgg gat ggc ctg cgc ttt ctg cag cgg aac ggc ctc ctg aac         768
Gly Tyr Arg Asp Gly Leu Arg Phe Leu Gln Arg Asn Gly Leu Leu Asn
                    245                 250                 255 cgg ccc aac ccc ttg ctg gcg ttg ccc ccc gcc cgc ccc cac ggc cca         816
Arg Pro Asn Pro Leu Leu Ala Leu Pro Pro Ala Arg Pro His Gly Pro
            260                 265                 270 gag gac aag gac cag gca gtg gag agc gcc caa gcg gag gat tac tcg         864
Glu Asp Lys Asp Gln Ala Val Glu Ser Ala Gln Ala Glu Asp Tyr Ser
        275                 280                 285 cag ctg ccc gga gaa gat cac atc ctg gag cac ctg ccc gcc cgg ctc         912
Gln Leu Pro Gly Glu Asp His Ile Leu Glu His Leu Pro Ala Arg Leu
    290                 295                 300 aat gag gcc ctg ctg gag gcc tgc gtg gag ccc acg gac ctg ctg acc         960
Asn Glu Ala Leu Leu Glu Ala Cys Val Glu Pro Thr Asp Leu Leu Thr
305                 310                 315                 320 acc ctc tcc aac atg ctg cct gtg cgt ctg gcc acg gcc atg atg gtg        1008
Thr Leu Ser Asn Met Leu Pro Val Arg Leu Ala Thr Ala Met Met Val
                    325                 330                 335 ccc tac acg ctg ccg ctg gag agc gct ctg tcc ttc acc atc cgc ttg        1056
Pro Tyr Thr Leu Pro Leu Glu Ser Ala Leu Ser Phe Thr Ile Arg Leu
            340                 345                 350 ctg gag tgg ctg ccc gac gtt ccc gag gac atc cgg tgg atg aag gag        1104
Leu Glu Trp Leu Pro Asp Val Pro Glu Asp Ile Arg Trp Met Lys Glu
        355                 360                 365 cag acg ggc agc atc tgc cag tac ctg gtg atg cgc gcc aag agg aag        1152
Gln Thr Gly Ser Ile Cys Gln Tyr Leu Val Met Arg Ala Lys Arg Lys
    370                 375                 380 ctg ggc agg cac ctg ccc tcc agg ctg ccg gag cag gtg gag ctg cgc        1200
```

-continued

```
Leu Gly Arg His Leu Pro Ser Arg Leu Pro Glu Gln Val Glu Leu Arg
385                 390                 395                 400 cgc gtc cag tcg ctg ccg tcc gtg ccg ctg tcc tgc gcc gcc tac aga      1248
Arg Val Gln Ser Leu Pro Ser Val Pro Leu Ser Cys Ala Ala Tyr Arg
                405                 410                 415 gag gca ctg ccc ggc tgg atg cgc aac aac ctc tcg ctg ggg gac gcg      1296
Glu Ala Leu Pro Gly Trp Met Arg Asn Asn Leu Ser Leu Gly Asp Ala
            420                 425                 430 ctg gcc aag tgg gag gag tgc cag cgc cag ctg ctg ctc ggc ctc ttc      1344
Leu Ala Lys Trp Glu Glu Cys Gln Arg Gln Leu Leu Leu Gly Leu Phe
        435                 440                 445 tgc acc aac gtg gcc ttc ccg ccc gaa gct ctg cgc atg cgc gca ccc      1392
Cys Thr Asn Val Ala Phe Pro Pro Glu Ala Leu Arg Met Arg Ala Pro
    450                 455                 460 gcc gac ccg gct ccc gcc ccg gcg gac cca gca tcc ccg cag cac cag      1440
Ala Asp Pro Ala Pro Ala Pro Ala Asp Pro Ala Ser Pro Gln His Gln
465                 470                 475                 480 ccg gcc ggg cct gcc ccc ttg ctg agc acc cct gct ccc gag gcc cgg      1488
Pro Ala Gly Pro Ala Pro Leu Leu Ser Thr Pro Ala Pro Glu Ala Arg
                485                 490                 495 ccc gtg atc ggg gcc ctg ggg ctg tga                                   1515
Pro Val Ile Gly Ala Leu Gly Leu
                500

<210> SEQ ID NO 5
<211> LENGTH: 762
<212> TYPE: DNA
<213> ORGANISM: Homo sapiens
<220> FEATURE:
<221> NAME/KEY: CDS
<222> LOCATION: (1)..(759)

<400> SEQUENCE: 5 atg aag cac atc aac cta tca ttt gca gcg tgt gga ttt ctg gca att       48
Met Lys His Ile Asn Leu Ser Phe Ala Ala Cys Gly Phe Leu Gly Ile
1               5                   10                  15 tac cac ttg ggg gca gca tct gca ctt tgc aga cat ggc aaa aaa ctt       96
Tyr His Leu Gly Ala Ala Ser Ala Leu Cys Arg His Gly Lys Lys Leu
            20                  25                  30 gtg aag gat gtc aaa gcc ttc gct ggg gcg tct gcg gga tcg ttg gtt      144
Val Lys Asp Val Lys Ala Phe Ala Gly Ala Ser Ala Gly Ser Leu Val
        35                  40                  45 gct tct gtt ctg cta aca gca cca gaa aaa ata gag gaa tgt aac caa      192
Ala Ser Val Leu Leu Thr Ala Pro Glu Lys Ile Glu Glu Cys Asn Gln
    50                  55                  60 ttt acc tac aag ttt gcc gaa gaa atc aga agg cag tct ttc ggg gca      240
Phe Thr Tyr Lys Phe Ala Glu Glu Ile Arg Arg Gln Ser Phe Gly Ala
65                  70                  75                  80 gta acg ccc ggt tat gac ttc atg gcc cga cta aga agt ggg atg gag      288
Val Thr Pro Gly Tyr Asp Phe Met Ala Arg Leu Arg Ser Gly Met Glu
                85                  90                  95 tcg att ctt cct ccc agc gct cac gag ctg gcc cag aac cga ctg cac      336
Ser Ile Leu Pro Pro Ser Ala His Glu Leu Ala Gln Asn Arg Leu His
            100                 105                 110 gta tcc atc acc aac gcc aaa acc aga gaa aat cac tta gtc tcc act      384
Val Ser Ile Thr Asn Ala Lys Thr Arg Glu Asn His Leu Val Ser Thr
        115                 120                 125 ttt tcc tcc agg gag gac ctc att aag gtc ctc cta gcc agc agt ttt      432
Phe Ser Ser Arg Glu Asp Leu Ile Lys Val Leu Leu Ala Ser Ser Phe
    130                 135                 140 gtg ccc att tat gca gga ctg aag cta gtg gaa tac aaa ggg cag aag      480
Val Pro Ile Tyr Ala Gly Leu Lys Leu Val Glu Tyr Lys Gly Gln Lys
```

```
Val Pro Ile Tyr Ala Gly Leu Lys Leu Val Glu Tyr Lys Gly Gln Lys
145                 150                 155                 160 tgg gtg gac gga ggc ctc acc aac gct ctt ccc atc ctg ccc gtc ggc    528
Trp Val Asp Gly Gly Leu Thr Asn Ala Leu Pro Ile Leu Pro Val Gly
                165                 170                 175 cgg aca gta acc atc tcc ccc ttc agt gga cga ctg gac atc tcc ccg    576
Arg Thr Val Thr Ile Ser Pro Phe Ser Gly Arg Leu Asp Ile Ser Pro
            180                 185                 190 cag gac aaa ggg cag cta gat ctg tat gtt aat atc gcc aag cag gat    624
Gln Asp Lys Gly Gln Leu Asp Leu Tyr Val Asn Ile Ala Lys Gln Asp
        195                 200                 205 atc atg ttg tcc ctg gca aac ctg gtg aga ctc aac caa gcc ctt ttt    672
Ile Met Leu Ser Leu Ala Asn Leu Val Arg Leu Asn Gln Ala Leu Phe
    210                 215                 220 ccc cca agc aag agg aaa atg gaa tct ttg tat cag tgt ggt ttt gat    720
Pro Pro Ser Lys Arg Lys Met Glu Ser Leu Tyr Gln Cys Gly Phe Asp
225                 230                 235                 240 gac act gtt aag ttt tta ctt aaa gaa aat tgg ttt gaa taa            762
Asp Thr Val Lys Phe Leu Leu Lys Glu Asn Trp Phe Glu
                245                 250
```

<210> SEQ ID NO 6
<211> LENGTH: 504
<212> TYPE: PRT
<213> ORGANISM: Homo sapiens

<400> SEQUENCE: 6

```
Met Phe Pro Arg Glu Lys Thr Trp Asn Ile Ser Phe Ala Gly Cys Gly
 1               5                  10                  15

Phe Leu Gly Val Tyr Tyr Val Gly Val Ala Ser Cys Leu Arg Glu His
                20                  25                  30

Ala Pro Phe Leu Val Ala Asn Ala Thr His Ile Tyr Gly Ala Ser Ala
            35                  40                  45

Gly Ala Leu Thr Ala Thr Ala Leu Val Thr Gly Val Cys Leu Gly Glu
        50                  55                  60

Ala Gly Ala Lys Phe Ile Glu Val Ser Lys Glu Ala Arg Lys Arg Phe
65                  70                  75                  80

Leu Gly Pro Leu His Pro Ser Phe Asn Leu Val Lys Ile Ile Arg Ser
                85                  90                  95

Phe Leu Leu Lys Val Leu Pro Ala Asp Ser His Glu His Ala Ser Gly
                100                 105                 110

Arg Leu Gly Ile Ser Leu Thr Arg Val Ser Asp Gly Glu Asn Val Ile
            115                 120                 125

Ile Ser His Phe Asn Ser Lys Asp Glu Leu Ile Gln Ala Asn Val Cys
        130                 135                 140

Ser Gly Phe Ile Pro Val Tyr Cys Gly Leu Ile Pro Pro Ser Leu Gln
145                 150                 155                 160

Gly Val Arg Tyr Val Asp Gly Gly Ile Ser Asp Asn Leu Pro Leu Tyr
                165                 170                 175

Glu Leu Lys Asn Thr Ile Thr Val Ser Pro Phe Ser Gly Glu Ser Asp
                180                 185                 190

Ile Cys Pro Gln Asp Ser Ser Thr Asn Ile His Glu Leu Arg Val Thr
            195                 200                 205

Asn Thr Ser Ile Gln Phe Asn Leu Arg Asn Leu Tyr Arg Leu Ser Lys
        210                 215                 220

Ala Leu Phe Pro Pro Glu Pro Leu Val Leu Arg Glu Met Cys Lys Gln
225                 230                 235                 240
```

```
Gly Tyr Arg Asp Gly Leu Arg Phe Leu Gln Arg Asn Gly Leu Leu Asn
                245                 250                 255

Arg Pro Asn Pro Leu Leu Ala Leu Pro Pro Ala Arg Pro His Gly Pro
            260                 265                 270

Glu Asp Lys Asp Gln Ala Val Glu Ser Ala Gln Ala Glu Asp Tyr Ser
        275                 280                 285

Gln Leu Pro Gly Glu Asp His Ile Leu Glu His Leu Pro Ala Arg Leu
    290                 295                 300

Asn Glu Ala Leu Leu Glu Ala Cys Val Glu Pro Thr Asp Leu Leu Thr
305                 310                 315                 320

Thr Leu Ser Asn Met Leu Pro Val Arg Leu Ala Thr Ala Met Met Val
                325                 330                 335

Pro Tyr Thr Leu Pro Leu Glu Ser Ala Leu Ser Phe Thr Ile Arg Leu
            340                 345                 350

Leu Glu Trp Leu Pro Asp Val Pro Glu Asp Ile Arg Trp Met Lys Glu
        355                 360                 365

Gln Thr Gly Ser Ile Cys Gln Tyr Leu Val Met Arg Ala Lys Arg Lys
    370                 375                 380

Leu Gly Arg His Leu Pro Ser Arg Leu Pro Glu Gln Val Glu Leu Arg
385                 390                 395                 400

Arg Val Gln Ser Leu Pro Ser Val Pro Leu Ser Cys Ala Ala Tyr Arg
                405                 410                 415

Glu Ala Leu Pro Gly Trp Met Arg Asn Asn Leu Ser Leu Gly Asp Ala
            420                 425                 430

Leu Ala Lys Trp Glu Glu Cys Gln Arg Gln Leu Leu Leu Gly Leu Phe
        435                 440                 445

Cys Thr Asn Val Ala Phe Pro Pro Glu Ala Leu Arg Met Arg Ala Pro
    450                 455                 460

Ala Asp Pro Ala Pro Ala Pro Asp Pro Ala Ser Pro Gln His Gln
465                 470                 475                 480

Pro Ala Gly Pro Ala Pro Leu Leu Ser Thr Pro Ala Pro Glu Ala Arg
                485                 490                 495

Pro Val Ile Gly Ala Leu Gly Leu
            500

<210> SEQ ID NO 7
<211> LENGTH: 253
<212> TYPE: PRT
<213> ORGANISM: Homo sapiens

<400> SEQUENCE: 7

Met Lys His Ile Asn Leu Ser Phe Ala Ala Cys Gly Phe Leu Gly Ile
1               5                   10                  15

Tyr His Leu Gly Ala Ala Ser Ala Leu Cys Arg His Gly Lys Lys Leu
            20                  25                  30

Val Lys Asp Val Lys Ala Phe Ala Gly Ala Ser Ala Gly Ser Leu Val
        35                  40                  45

Ala Ser Val Leu Leu Thr Ala Pro Glu Lys Ile Glu Glu Cys Asn Gln
    50                  55                  60

Phe Thr Tyr Lys Phe Ala Glu Glu Ile Arg Arg Gln Ser Phe Gly Ala
65                  70                  75                  80

Val Thr Pro Gly Tyr Asp Phe Met Ala Arg Leu Arg Ser Gly Met Glu
                85                  90                  95

Ser Ile Leu Pro Pro Ser Ala His Glu Leu Ala Gln Asn Arg Leu His
```

```
                        100                 105                 110
        Val Ser Ile Thr Asn Ala Lys Thr Arg Glu Asn His Leu Val Ser Thr
            115                 120                 125

Phe Ser Ser Arg Glu Asp Leu Ile Lys Val Leu Leu Ala Ser Ser Phe
        130                 135                 140

Val Pro Ile Tyr Ala Gly Leu Lys Leu Val Glu Tyr Lys Gly Gln Lys
        145                 150                 155                 160

Trp Val Asp Gly Gly Leu Thr Asn Ala Leu Pro Ile Leu Pro Val Gly
                        165                 170                 175

Arg Thr Val Thr Ile Ser Pro Phe Ser Gly Arg Leu Asp Ile Ser Pro
                    180                 185                 190

Gln Asp Lys Gly Gln Leu Asp Leu Tyr Val Asn Ile Ala Lys Gln Asp
                195                 200                 205

Ile Met Leu Ser Leu Ala Asn Leu Val Arg Leu Asn Gln Ala Leu Phe
            210                 215                 220

Pro Pro Ser Lys Arg Lys Met Glu Ser Leu Tyr Gln Cys Gly Phe Asp
        225                 230                 235                 240

Asp Thr Val Lys Phe Leu Leu Lys Glu Asn Trp Phe Glu
                        245                 250

<210> SEQ ID NO 8
<211> LENGTH: 1446
<212> TYPE: DNA
<213> ORGANISM: Homo sapiens
<220> FEATURE:
<221> NAME/KEY: CDS
<222> LOCATION: (1)..(1443)

<400> SEQUENCE: 8 atg tac gac gca gag cgc ggc tgg agc ttg tcc ttc gcg ggc tgc ggc      48
Met Tyr Asp Ala Glu Arg Gly Trp Ser Leu Ser Phe Ala Gly Cys Gly
1               5                   10                  15 ttc ctg ggc ttc tac cac gtc ggg gcg acc cgc tgc ctg agc gag cac      96
Phe Leu Gly Phe Tyr His Val Gly Ala Thr Arg Cys Leu Ser Glu His
            20                  25                  30 gcc ccg cac ctc ctc cgc gac gcg cgc atg ttg ttc ggc gct tcg gcc     144
Ala Pro His Leu Leu Arg Asp Ala Arg Met Leu Phe Gly Ala Ser Ala
        35                  40                  45 ggg gcg ttg cac tgc gtc ggc gtc ctc tcc ggt atc ccg ctg gag cag     192
Gly Ala Leu His Cys Val Gly Val Leu Ser Gly Ile Pro Leu Glu Gln
    50                  55                  60 act ctg cag gtc ctc tca gat ctt gtg cgg aag gcc agg agt cgg aac     240
Thr Leu Gln Val Leu Ser Asp Leu Val Arg Lys Ala Arg Ser Arg Asn
65                  70                  75                  80 att ggc atc ttc cat cca tcc ttc aac tta agc aag ttc ctc cga cag     288
Ile Gly Ile Phe His Pro Ser Phe Asn Leu Ser Lys Phe Leu Arg Gln
                85                  90                  95 ggt ctc tgc aaa tgc ctc ccg gcc aat gtc cac cag ctc atc tcc ggc     336
Gly Leu Cys Lys Cys Leu Pro Ala Asn Val His Gln Leu Ile Ser Gly
            100                 105                 110 aaa ata ggc atc tct ctt acc aga gtg tct gat ggg gaa aac gtt ctg     384
Lys Ile Gly Ile Ser Leu Thr Arg Val Ser Asp Gly Glu Asn Val Leu
        115                 120                 125 gtg tct gac ttt cgg tcc aaa gac gaa gtc gtg gat gcc ttg gta tgt     432
Val Ser Asp Phe Arg Ser Lys Asp Glu Val Val Asp Ala Leu Val Cys
    130                 135                 140 tcc tgc ttc atc ccc ttc tac agt ggc ctt atc cct cct tcc ttc aga     480
Ser Cys Phe Ile Pro Phe Tyr Ser Gly Leu Ile Pro Pro Ser Phe Arg
145                 150                 155                 160
```

|     |     |     |     |     |     |     |     |     |     |     |     |     |     |     |     |      |
| --- | --- | --- | --- | --- | --- | --- | --- | --- | --- | --- | --- | --- | --- | --- | --- | ---  |
| ggc | gtg | cga | tat | gtg | gat | gga | gga | gtg | agt | gac | aac | gta | ccc | ttc | att |  528 |
| Gly | Val | Arg | Tyr | Val | Asp | Gly | Gly | Val | Ser | Asp | Asn | Val | Pro | Phe | Ile |      |
|     |     |     | 165 |     |     |     | 170 |     |     |     |     | 175 |     |     |     |      |
| gat | gcc | aaa | aca | acc | atc | acc | gtg | tcc | ccc | ttc | tat | ggg | gag | tac | gac |  576 |
| Asp | Ala | Lys | Thr | Thr | Ile | Thr | Val | Ser | Pro | Phe | Tyr | Gly | Glu | Tyr | Asp |      |
|     |     |     | 180 |     |     |     | 185 |     |     |     |     | 190 |     |     |     |      |
| atc | tgc | cct | aaa | gtc | aag | tcc | acg | aac | ttt | ctt | cat | gtg | gac | atc | acc |  624 |
| Ile | Cys | Pro | Lys | Val | Lys | Ser | Thr | Asn | Phe | Leu | His | Val | Asp | Ile | Thr |      |
|     |     | 195 |     |     |     | 200 |     |     |     |     | 205 |     |     |     |     |      |
| aag | ctc | agt | cta | cgc | ctc | tgc | aca | ggg | aac | ctc | tac | ctt | ctc | tcg | aga |  672 |
| Lys | Leu | Ser | Leu | Arg | Leu | Cys | Thr | Gly | Asn | Leu | Tyr | Leu | Leu | Ser | Arg |      |
|     | 210 |     |     |     |     | 215 |     |     |     |     | 220 |     |     |     |     |      |
| gct | ttt | gtc | ccc | ccg | gat | ctc | aag | gtg | ctg | gga | gag | ata | tgc | ctt | cga |  720 |
| Ala | Phe | Val | Pro | Pro | Asp | Leu | Lys | Val | Leu | Gly | Glu | Ile | Cys | Leu | Arg |      |
| 225 |     |     |     | 230 |     |     |     |     | 235 |     |     |     |     | 240 |     |      |
| gga | tat | ttg | gat | gca | ttc | agg | ttc | ttg | gaa | gag | aag | ggc | atc | tgc | aac |  768 |
| Gly | Tyr | Leu | Asp | Ala | Phe | Arg | Phe | Leu | Glu | Glu | Lys | Gly | Ile | Cys | Asn |      |
|     |     |     |     | 245 |     |     |     |     | 250 |     |     |     |     | 255 |     |      |
| agg | ccc | cag | cca | ggc | ctg | aag | tca | tcc | tca | gaa | ggg | atg | gat | cct | gag |  816 |
| Arg | Pro | Gln | Pro | Gly | Leu | Lys | Ser | Ser | Ser | Glu | Gly | Met | Asp | Pro | Glu |      |
|     |     |     | 260 |     |     |     |     | 265 |     |     |     |     | 270 |     |     |      |
| gtc | gcc | atg | ccc | agc | tgg | gca | aac | atg | agt | ctg | gat | tct | tcc | ccg | gag |  864 |
| Val | Ala | Met | Pro | Ser | Trp | Ala | Asn | Met | Ser | Leu | Asp | Ser | Ser | Pro | Glu |      |
|     |     | 275 |     |     |     |     | 280 |     |     |     |     | 285 |     |     |     |      |
| tcg | gct | gcc | ttg | gct | gtg | agg | ctg | gag | gga | gat | gag | ctg | cta | gac | cac |  912 |
| Ser | Ala | Ala | Leu | Ala | Val | Arg | Leu | Glu | Gly | Asp | Glu | Leu | Leu | Asp | His |      |
|     | 290 |     |     |     |     | 295 |     |     |     |     | 300 |     |     |     |     |      |
| ctg | cgt | ctc | agc | atc | ctg | ccc | tgg | gat | gag | agc | atc | ctg | gac | acc | ctc |  960 |
| Leu | Arg | Leu | Ser | Ile | Leu | Pro | Trp | Asp | Glu | Ser | Ile | Leu | Asp | Thr | Leu |      |
| 305 |     |     |     | 310 |     |     |     |     | 315 |     |     |     |     | 320 |     |      |
| tcg | ccc | agg | ctc | gct | aca | gca | ctg | agt | gaa | gaa | atg | aaa | gac | aaa | ggt | 1008 |
| Ser | Pro | Arg | Leu | Ala | Thr | Ala | Leu | Ser | Glu | Glu | Met | Lys | Asp | Lys | Gly |      |
|     |     |     |     | 325 |     |     |     |     | 330 |     |     |     |     | 335 |     |      |
| gga | tac | atg | agc | aag | att | tgc | aac | ttg | cta | ccc | att | agg | ata | atg | tct | 1056 |
| Gly | Tyr | Met | Ser | Lys | Ile | Cys | Asn | Leu | Leu | Pro | Ile | Arg | Ile | Met | Ser |      |
|     |     |     | 340 |     |     |     |     | 345 |     |     |     |     | 350 |     |     |      |
| tat | gta | atg | ctg | ccc | tgt | acc | ctg | cct | gtg | gaa | tct | gcc | att | gcg | att | 1104 |
| Tyr | Val | Met | Leu | Pro | Cys | Thr | Leu | Pro | Val | Glu | Ser | Ala | Ile | Ala | Ile |      |
|     |     | 355 |     |     |     |     | 360 |     |     |     |     | 365 |     |     |     |      |
| gtc | cag | aga | ctg | gtg | aca | tgg | ctt | cca | gat | atg | ccc | gac | gat | gtc | ctg | 1152 |
| Val | Gln | Arg | Leu | Val | Thr | Trp | Leu | Pro | Asp | Met | Pro | Asp | Asp | Val | Leu |      |
|     | 370 |     |     |     |     | 375 |     |     |     |     | 380 |     |     |     |     |      |
| tgg | ttg | cag | tgg | gtg | acc | tca | cag | gtg | ttc | act | cga | gtg | ctg | atg | tgt | 1200 |
| Trp | Leu | Gln | Trp | Val | Thr | Ser | Gln | Val | Phe | Thr | Arg | Val | Leu | Met | Cys |      |
| 385 |     |     |     |     | 390 |     |     |     |     | 395 |     |     |     |     | 400 |      |
| ctg | ctc | ccc | gcc | tcc | agg | tcc | caa | atg | cca | gtg | agc | agc | caa | cag | gcc | 1248 |
| Leu | Leu | Pro | Ala | Ser | Arg | Ser | Gln | Met | Pro | Val | Ser | Ser | Gln | Gln | Ala |      |
|     |     |     |     | 405 |     |     |     |     | 410 |     |     |     |     | 415 |     |      |
| tcc | cca | tgc | aca | cct | gag | cag | gac | tgg | ccc | tgc | tgg | act | ccc | tgc | tcc | 1296 |
| Ser | Pro | Cys | Thr | Pro | Glu | Gln | Asp | Trp | Pro | Cys | Trp | Thr | Pro | Cys | Ser |      |
|     |     |     | 420 |     |     |     |     | 425 |     |     |     |     | 430 |     |     |      |
| ccc | gag | ggc | tgt | cca | gca | gag | acc | aaa | gca | gag | gcc | acc | ccg | cgg | tcc | 1344 |
| Pro | Glu | Gly | Cys | Pro | Ala | Glu | Thr | Lys | Ala | Glu | Ala | Thr | Pro | Arg | Ser |      |
|     |     | 435 |     |     |     |     | 440 |     |     |     |     | 445 |     |     |     |      |
| atc | ctc | agg | tcc | agc | ctg | aac | ttc | ttc | ttg | ggc | aat | aaa | gta | cct | gct | 1392 |
| Ile | Leu | Arg | Ser | Ser | Leu | Asn | Phe | Phe | Leu | Gly | Asn | Lys | Val | Pro | Ala |      |
|     | 450 |     |     |     |     | 455 |     |     |     |     | 460 |     |     |     |     |      |
| ggt | gct | gag | ggg | ctc | tcc | acc | ttt | ccc | agt | ttt | tca | cta | gag | aag | agt | 1440 |
| Gly | Ala | Glu | Gly | Leu | Ser | Thr | Phe | Pro | Ser | Phe | Ser | Leu | Glu | Lys | Ser |      |

```
                465                 470                 475                 480 ctg tga                                                                              1446
Leu <210> SEQ ID NO 9
<211> LENGTH: 481
<212> TYPE: PRT
<213> ORGANISM: Homo sapiens

<400> SEQUENCE: 9

Met Tyr Asp Ala Glu Arg Gly Trp Ser Leu Ser Phe Ala Gly Cys Gly
  1               5                  10                  15

Phe Leu Gly Phe Tyr His Val Gly Ala Thr Arg Cys Leu Ser Glu His
                 20                  25                  30

Ala Pro His Leu Leu Arg Asp Ala Arg Met Leu Phe Gly Ala Ser Ala
             35                  40                  45

Gly Ala Leu His Cys Val Gly Val Leu Ser Gly Ile Pro Leu Glu Gln
         50                  55                  60

Thr Leu Gln Val Leu Ser Asp Leu Val Arg Lys Ala Arg Ser Arg Asn
 65                  70                  75                  80

Ile Gly Ile Phe His Pro Ser Phe Asn Leu Ser Lys Phe Leu Arg Gln
                 85                  90                  95

Gly Leu Cys Lys Cys Leu Pro Ala Asn Val His Gln Leu Ile Ser Gly
            100                 105                 110

Lys Ile Gly Ile Ser Leu Thr Arg Val Ser Asp Gly Glu Asn Val Leu
        115                 120                 125

Val Ser Asp Phe Arg Ser Lys Asp Glu Val Val Asp Ala Leu Val Cys
130                 135                 140

Ser Cys Phe Ile Pro Phe Tyr Ser Gly Leu Ile Pro Pro Ser Phe Arg
145                 150                 155                 160

Gly Val Arg Tyr Val Asp Gly Gly Val Ser Asp Asn Val Pro Phe Ile
                165                 170                 175

Asp Ala Lys Thr Thr Ile Thr Val Ser Pro Phe Tyr Gly Glu Tyr Asp
            180                 185                 190

Ile Cys Pro Lys Val Lys Ser Thr Asn Phe Leu His Val Asp Ile Thr
        195                 200                 205

Lys Leu Ser Leu Arg Leu Cys Thr Gly Asn Leu Tyr Leu Leu Ser Arg
    210                 215                 220

Ala Phe Val Pro Pro Asp Leu Lys Val Leu Gly Glu Ile Cys Leu Arg
225                 230                 235                 240

Gly Tyr Leu Asp Ala Phe Arg Phe Leu Glu Glu Lys Gly Ile Cys Asn
                245                 250                 255

Arg Pro Gln Pro Gly Leu Lys Ser Ser Ser Glu Gly Met Asp Pro Glu
            260                 265                 270

Val Ala Met Pro Ser Trp Ala Asn Met Ser Leu Asp Ser Ser Pro Glu
        275                 280                 285

Ser Ala Ala Leu Ala Val Arg Leu Glu Gly Asp Glu Leu Leu Asp His
    290                 295                 300

Leu Arg Leu Ser Ile Leu Pro Trp Asp Glu Ser Ile Leu Asp Thr Leu
305                 310                 315                 320

Ser Pro Arg Leu Ala Thr Ala Leu Ser Glu Glu Met Lys Asp Lys Gly
                325                 330                 335

Gly Tyr Met Ser Lys Ile Cys Asn Leu Leu Pro Ile Arg Ile Met Ser
            340                 345                 350
```

```
Tyr Val Met Leu Pro Cys Thr Leu Pro Val Glu Ser Ala Ile Ala Ile
        355                 360                 365

Val Gln Arg Leu Val Thr Trp Leu Pro Asp Met Pro Asp Asp Val Leu
    370                 375                 380

Trp Leu Gln Trp Val Thr Ser Gln Val Phe Thr Arg Val Leu Met Cys
385                 390                 395                 400

Leu Leu Pro Ala Ser Arg Ser Gln Met Pro Val Ser Ser Gln Gln Ala
                405                 410                 415

Ser Pro Cys Thr Pro Glu Gln Asp Trp Pro Cys Trp Thr Pro Cys Ser
            420                 425                 430

Pro Glu Gly Cys Pro Ala Glu Thr Lys Ala Glu Ala Thr Pro Arg Ser
        435                 440                 445

Ile Leu Arg Ser Ser Leu Asn Phe Phe Leu Gly Asn Lys Val Pro Ala
    450                 455                 460

Gly Ala Glu Gly Leu Ser Thr Phe Pro Ser Phe Ser Leu Glu Lys Ser
465                 470                 475                 480

Leu

<210> SEQ ID NO 10
<211> LENGTH: 1446
<212> TYPE: DNA
<213> ORGANISM: Homo sapiens
<220> FEATURE:
<221> NAME/KEY: CDS
<222> LOCATION: (1)..(1443)

<400> SEQUENCE: 10 atg tac gac gca gag cgc ggc tgg agc ttg tcc ttc gcg ggc tgc ggc      48
Met Tyr Asp Ala Glu Arg Gly Trp Ser Leu Ser Phe Ala Gly Cys Gly
1               5                   10                  15 ttc ctg ggc ttc tac cac gtc ggg gcg acc cgc tgc ctg agc gag cac      96
Phe Leu Gly Phe Tyr His Val Gly Ala Thr Arg Cys Leu Ser Glu His
                20                  25                  30 gcc ccg cac ctc ctc cgc gac gcg cgc atg ttg ttc ggc gct tcg gcc     144
Ala Pro His Leu Leu Arg Asp Ala Arg Met Leu Phe Gly Ala Ser Ala
            35                  40                  45 ggg gcg ttg cac tgc gtc ggc gtc ctc tcc ggt atc ccg ctg gag cag     192
Gly Ala Leu His Cys Val Gly Val Leu Ser Gly Ile Pro Leu Glu Gln
        50                  55                  60 act ctg cag gtc ctc tca gat ctt gtg cgg aag gcc agg agt cgg aac     240
Thr Leu Gln Val Leu Ser Asp Leu Val Arg Lys Ala Arg Ser Arg Asn
65                  70                  75                  80 att ggc atc ttc cat cca tcc ttc aac tta agc aag ttc ctc cga cag     288
Ile Gly Ile Phe His Pro Ser Phe Asn Leu Ser Lys Phe Leu Arg Gln
                85                  90                  95 ggt ctc tgc aaa tgc ctc ccg gcc aat gtc cac cag ctc atc tcc ggc     336
Gly Leu Cys Lys Cys Leu Pro Ala Asn Val His Gln Leu Ile Ser Gly
                100                 105                 110 aaa ata ggc atc tct ctt acc aga gtg tct gat ggg gaa aac gtt ctg     384
Lys Ile Gly Ile Ser Leu Thr Arg Val Ser Asp Gly Glu Asn Val Leu
            115                 120                 125 gtg tct gac ttt cgg tcc aaa gac gaa gtc gtg gat gcc ttg gta tgt     432
Val Ser Asp Phe Arg Ser Lys Asp Glu Val Val Asp Ala Leu Val Cys
        130                 135                 140 tcc tgc ttc atc ccc ttc tac agt ggc ctt atc cct cct tcc ttc aga     480
Ser Cys Phe Ile Pro Phe Tyr Ser Gly Leu Ile Pro Pro Ser Phe Arg
145                 150                 155                 160 ggc gtg cga tat gtg gat gga gga gtg agt gac aac gta ccc ttc att     528
Gly Val Arg Tyr Val Asp Gly Gly Val Ser Asp Asn Val Pro Phe Ile
```

-continued

```
                  165                 170                 175
gat gcc aaa aca acc atc acc gtg tcc ccc ttc tat ggg gag tac gac    576
Asp Ala Lys Thr Thr Ile Thr Val Ser Pro Phe Tyr Gly Glu Tyr Asp
            180                 185                 190 atc tgc cct aaa gtc aag tcc acg aac ttt ctt cat gtg gac atc acc    624
Ile Cys Pro Lys Val Lys Ser Thr Asn Phe Leu His Val Asp Ile Thr
        195                 200                 205 aag ctc agt cta cgc ctc tgc aca ggg aac ctc tac ctt ctc tcg aga    672
Lys Leu Ser Leu Arg Leu Cys Thr Gly Asn Leu Tyr Leu Leu Ser Arg
    210                 215                 220 gct ttt gtc ccc ccg gat ctc aag gtg ctg gga gag ata tgc ctt cga    720
Ala Phe Val Pro Pro Asp Leu Lys Val Leu Gly Glu Ile Cys Leu Arg
225                 230                 235                 240 gga tat ttg gat gca ttc agg ttc ttg gaa gag aag ggc atc tgc aac    768
Gly Tyr Leu Asp Ala Phe Arg Phe Leu Glu Glu Lys Gly Ile Cys Asn
                245                 250                 255 agg ccc cag cca ggc ctg aag tca tcc tca gaa ggg atg gat cct gag    816
Arg Pro Gln Pro Gly Leu Lys Ser Ser Ser Glu Gly Met Asp Pro Glu
            260                 265                 270 gtc gcc atg ccc agc tgg gca aac atg agt ctg gat tct tcc ccg gag    864
Val Ala Met Pro Ser Trp Ala Asn Met Ser Leu Asp Ser Ser Pro Glu
        275                 280                 285 tcg gct gcc ttg gct gtg agg ctg gag gga gat gag ctg cta gac cac    912
Ser Ala Ala Leu Ala Val Arg Leu Glu Gly Asp Glu Leu Leu Asp His
    290                 295                 300 ctg cgt ctc agc atc ctg ccc tgg gat gag agc atc ctg gac acc ctc    960
Leu Arg Leu Ser Ile Leu Pro Trp Asp Glu Ser Ile Leu Asp Thr Leu
305                 310                 315                 320 tcg ccc agg ctc gct aca gca ctg agt gaa gaa atg aaa gac aaa ggt   1008
Ser Pro Arg Leu Ala Thr Ala Leu Ser Glu Glu Met Lys Asp Lys Gly
                325                 330                 335 gga tac atg agc aag att tgc aac ttg cta ccc att agg ata atg tct   1056
Gly Tyr Met Ser Lys Ile Cys Asn Leu Leu Pro Ile Arg Ile Met Ser
            340                 345                 350 tat gta atg ctg ccc tgt acc ctg cct gtg gaa tct gcc att gcg att   1104
Tyr Val Met Leu Pro Cys Thr Leu Pro Val Glu Ser Ala Ile Ala Ile
        355                 360                 365 gtc cag aga ctg gtg aca tgg ctt cca gat atg ccc gac gat gtc ctg   1152
Val Gln Arg Leu Val Thr Trp Leu Pro Asp Met Pro Asp Asp Val Leu
    370                 375                 380 tgg ttg cag tgg gtg acc tca cag gtg ttc act cga gtg ctg atg tgt   1200
Trp Leu Gln Trp Val Thr Ser Gln Val Phe Thr Arg Val Leu Met Cys
385                 390                 395                 400 ctg ctc ccc gcc tcc agg tcc caa atg cca gtg agc agc caa cag gcc   1248
Leu Leu Pro Ala Ser Arg Ser Gln Met Pro Val Ser Ser Gln Gln Ala
                405                 410                 415 tcc cca tgc aca cct gag cag gac tgg ccc tgc tgg act ccc tgc tcc   1296
Ser Pro Cys Thr Pro Glu Gln Asp Trp Pro Cys Trp Thr Pro Cys Ser
            420                 425                 430 ccc aag ggc tgt cca gca gag acc aaa gca gag gcc acc ccg cgg tcc   1344
Pro Lys Gly Cys Pro Ala Glu Thr Lys Ala Glu Ala Thr Pro Arg Ser
        435                 440                 445 atc ctc agg tcc agc ctg aac ttc ttc ttg ggc aat aaa gta cct gct   1392
Ile Leu Arg Ser Ser Leu Asn Phe Phe Leu Gly Asn Lys Val Pro Ala
    450                 455                 460 ggt gct gag ggg ctc tcc acc ttt ccc agt ttt tca cta gag aag agt   1440
Gly Ala Glu Gly Leu Ser Thr Phe Pro Ser Phe Ser Leu Glu Lys Ser
465                 470                 475                 480 ctg tga                                                           1446
```

Leu

<210> SEQ ID NO 11
<211> LENGTH: 481
<212> TYPE: PRT
<213> ORGANISM: Homo sapiens

<400> SEQUENCE: 11

Met Tyr Asp Ala Glu Arg Gly Trp Ser Leu Ser Phe Ala Gly Cys Gly
 1               5                  10                  15

Phe Leu Gly Phe Tyr His Val Gly Ala Thr Arg Cys Leu Ser Glu His
            20                  25                  30

Ala Pro His Leu Leu Arg Asp Ala Arg Met Leu Phe Gly Ala Ser Ala
        35                  40                  45

Gly Ala Leu His Cys Val Gly Val Leu Ser Gly Ile Pro Leu Glu Gln
    50                  55                  60

Thr Leu Gln Val Leu Ser Asp Leu Val Arg Lys Ala Arg Ser Arg Asn
65                  70                  75                  80

Ile Gly Ile Phe His Pro Ser Phe Asn Leu Ser Lys Phe Leu Arg Gln
                85                  90                  95

Gly Leu Cys Lys Cys Leu Pro Ala Asn Val His Gln Leu Ile Ser Gly
            100                 105                 110

Lys Ile Gly Ile Ser Leu Thr Arg Val Ser Asp Gly Glu Asn Val Leu
        115                 120                 125

Val Ser Asp Phe Arg Ser Lys Asp Glu Val Val Asp Ala Leu Val Cys
    130                 135                 140

Ser Cys Phe Ile Pro Phe Tyr Ser Gly Leu Ile Pro Pro Ser Phe Arg
145                 150                 155                 160

Gly Val Arg Tyr Val Asp Gly Gly Val Ser Asp Asn Val Pro Phe Ile
                165                 170                 175

Asp Ala Lys Thr Thr Ile Thr Val Ser Pro Phe Tyr Gly Glu Tyr Asp
            180                 185                 190

Ile Cys Pro Lys Val Lys Ser Thr Asn Phe Leu His Val Asp Ile Thr
        195                 200                 205

Lys Leu Ser Leu Arg Leu Cys Thr Gly Asn Leu Tyr Leu Leu Ser Arg
    210                 215                 220

Ala Phe Val Pro Pro Asp Leu Lys Val Leu Gly Glu Ile Cys Leu Arg
225                 230                 235                 240

Gly Tyr Leu Asp Ala Phe Arg Phe Leu Glu Glu Lys Gly Ile Cys Asn
                245                 250                 255

Arg Pro Gln Pro Gly Leu Lys Ser Ser Glu Gly Met Asp Pro Glu
            260                 265                 270

Val Ala Met Pro Ser Trp Ala Asn Met Ser Leu Asp Ser Ser Pro Glu
        275                 280                 285

Ser Ala Ala Leu Ala Val Arg Leu Glu Gly Asp Glu Leu Leu Asp His
    290                 295                 300

Leu Arg Leu Ser Ile Leu Pro Trp Asp Glu Ser Ile Leu Asp Thr Leu
305                 310                 315                 320

Ser Pro Arg Leu Ala Thr Ala Leu Ser Glu Glu Met Lys Asp Lys Gly
                325                 330                 335

Gly Tyr Met Ser Lys Ile Cys Asn Leu Leu Pro Ile Arg Ile Met Ser
            340                 345                 350

Tyr Val Met Leu Pro Cys Thr Leu Pro Val Glu Ser Ala Ile Ala Ile
        355                 360                 365

-continued

```
Val Gln Arg Leu Val Thr Trp Leu Pro Asp Met Pro Asp Val Leu
    370                 375                 380
Trp Leu Gln Trp Val Thr Ser Gln Val Phe Thr Arg Val Leu Met Cys
385                 390                 395                 400
Leu Leu Pro Ala Ser Arg Ser Gln Met Pro Val Ser Ser Gln Gln Ala
                405                 410                 415
Ser Pro Cys Thr Pro Glu Gln Asp Trp Pro Cys Trp Thr Pro Cys Ser
            420                 425                 430
Pro Lys Gly Cys Pro Ala Glu Thr Lys Ala Glu Ala Thr Pro Arg Ser
        435                 440                 445
Ile Leu Arg Ser Ser Leu Asn Phe Phe Leu Gly Asn Lys Val Pro Ala
    450                 455                 460
Gly Ala Glu Gly Leu Ser Thr Phe Pro Ser Phe Ser Leu Glu Lys Ser
465                 470                 475                 480
Leu
```

<210> SEQ ID NO 12
<211> LENGTH: 6
<212> TYPE: PRT
<213> ORGANISM: Homo sapiens

<400> SEQUENCE: 12

```
Gly Cys Gly Phe Leu Gly
 1               5
```

<210> SEQ ID NO 13
<211> LENGTH: 5
<212> TYPE: PRT
<213> ORGANISM: Homo sapiens

<400> SEQUENCE: 13

```
Gly Ala Ser Ala Gly
 1               5
```

<210> SEQ ID NO 14
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
ggcaaaatag gcatctctct tacc                                          24

<210> SEQ ID NO 15
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
ggagggataa ggccactgta ga                                            22

<210> SEQ ID NO 16
<211> LENGTH: 28
<212> TYPE: DNA
<213> ORGANISM: Artificial Sequence
<220> FEATURE:
<223> OTHER INFORMATION: Description of Artificial Sequence: Synthetic
      probe

```
<400> SEQUENCE: 16
aacataccaa ggcatccacg acttcgtc                                        28

<210> SEQ ID NO 17
<211> LENGTH: 16
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
ccacggcgct ggtcac                                                     16

<210> SEQ ID NO 18
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
gcaggacctt cagcaggaaa c                                               21

<210> SEQ ID NO 19
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 19
tggcaccagc ctcacccagg cagac                                           25

<210> SEQ ID NO 20
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
gcacagaaaa tgaggattat taaagg                                          26

<210> SEQ ID NO 21
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
cgctgcaaat gataggttga tg                                              22

<210> SEQ ID NO 22
<211> LENGTH: 32
<212> TYPE: DNA
<213> ORGANISM: Artificial Sequence
<220> FEATURE:
<223> OTHER INFORMATION: Description of Artificial Sequence: Synthetic
      probe
```

```
<400> SEQUENCE: 22
tgcttcattc tagctgtagc actgcgagca ac                                    32

<210> SEQ ID NO 23
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
actgcacgcg gtcacctt                                                    18

<210> SEQ ID NO 24
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
cacgaggtcc atgaggatct c                                                21

<210> SEQ ID NO 25
<211> LENGTH: 28
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 25
tgtgcagtct ccctctcggc cgtataat                                         28

<210> SEQ ID NO 26
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
gccacagcgc tggtcact                                                    18

<210> SEQ ID NO 27
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
cctccttgga cacctcaata atg                                              23

<210> SEQ ID NO 28
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 28
```

```
cctgcctggg tgaagcaggt gc                                              22

<210> SEQ ID NO 29
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 29

His His His His His His
  1               5

<210> SEQ ID NO 30
<211> LENGTH: 12
<212> TYPE: PRT
<213> ORGANISM: Artificial Sequence
<220> FEATURE:
<223> OTHER INFORMATION: Description of Artificial Sequence: Synthetic
      His tag
<220> FEATURE:
<223> OTHER INFORMATION: This peptide may encompass 4-12 His residues

<400> SEQUENCE: 30

His His His His His His His His His His His His
  1               5                   10
```